US010659906B2

(12) United States Patent
Kim et al.

(10) Patent No.: US 10,659,906 B2
(45) Date of Patent: May 19, 2020

(54) AUDIO PARALLAX FOR VIRTUAL REALITY, AUGMENTED REALITY, AND MIXED REALITY

(71) Applicant: QUALCOMM Incorporated, San Diego, CA (US)

(72) Inventors: Moo Young Kim, San Diego, CA (US); Nils Günther Peters, San Diego, CA (US); Dipanjan Sen, San Diego, CA (US)

(73) Assignee: Qualcomm Incorporated, San Diego, CA (US)

( * ) Notice: Subject to any disclaimer, the term of this patent is extended or adjusted under 35 U.S.C. 154(b) by 10 days.

(21) Appl. No.: 15/868,656

(22) Filed: Jan. 11, 2018

(65) Prior Publication Data

US 2018/0206057 A1 Jul. 19, 2018

Related U.S. Application Data

(60) Provisional application No. 62/446,324, filed on Jan. 13, 2017.

(51) Int. Cl.
*A63F 13/30* (2014.01)
*A61B 6/00* (2006.01)
(Continued)

(52) U.S. Cl.
CPC ............ *H04S 7/304* (2013.01); *G10L 19/008* (2013.01); *H04R 5/033* (2013.01); *H04S 3/008* (2013.01);
(Continued)

(58) Field of Classification Search
CPC ....... H04S 7/304; H04S 7/306; G02B 17/017; H04R 5/033; G10L 19/00; A63F 13/30
(Continued)

(56) References Cited

U.S. PATENT DOCUMENTS 8,805,561 B2 8/2014 Wilcock et al.
2011/0200196 A1* 8/2011 Disch ........................ H04S 7/30 381/22

(Continued)

FOREIGN PATENT DOCUMENTS

WO 2017098949 A1 6/2017
WO 2018031123 A1 2/2018

OTHER PUBLICATIONS

Audio, "Call for Proposals for 3D Audio," International Organisation for Standardisation Organisation Internationale de Normalisation ISO/IEC JTC1/SC29/WG11 Coding of Moving Pictures and Audio, ISO/IEC PTC1/SC29/WG11/N13411, Geneva, CH, Jan. 2013, pp. 1-20.

(Continued)

*Primary Examiner* — Paul Kim
*Assistant Examiner* — Ubachukwu A Odunukwe
(74) *Attorney, Agent, or Firm* — Shumaker & Sieffert P.A.

(57) ABSTRACT

An example audio decoding device includes processing circuitry and a memory device coupled to the processing circuitry. The processing circuitry is configured to receive, in a bitstream, encoded representations of audio objects of a three-dimensional (3D) soundfield, to receive metadata associated with the bitstream, to obtain, from the received metadata, one or more transmission factors associated with one or more of the audio objects, and to apply the transmission factors to the one or more audio objects to obtain parallax-adjusted audio objects of the 3D soundfield. The memory device is configured to store at least a portion of the received bitstream, the received metadata, or the parallax-adjusted audio objects of the 3D soundfield.

30 Claims, 32 Drawing Sheets

(51) Int. Cl.
*G10L 19/00* (2013.01)
*H04S 3/00* (2006.01)
*H04S 7/00* (2006.01)
*G10L 19/008* (2013.01)
*H04R 5/033* (2006.01)

(52) U.S. Cl.
CPC ........... *H04S 7/306* (2013.01); *H04S 2400/01* (2013.01); *H04S 2400/03* (2013.01); *H04S 2400/11* (2013.01); *H04S 2400/13* (2013.01); *H04S 2420/01* (2013.01); *H04S 2420/03* (2013.01); *H04S 2420/11* (2013.01)

(58) Field of Classification Search
USPC .................... 381/22, 17; 348/14.08; 345/419
See application file for complete search history.

(56) References Cited

U.S. PATENT DOCUMENTS

| | | | |
|---|---|---|---|
| 2011/0249821 A1 | 10/2011 | Jaillet et al. | |
| 2011/0316967 A1 | 12/2011 | Etter | |
| 2012/0177204 A1* | 7/2012 | Hellmuth | G10L 19/008 381/22 |
| 2012/0206452 A1* | 8/2012 | Geisner | G02B 27/017 345/419 |
| 2014/0233917 A1 | 8/2014 | Xiang | |
| 2015/0055937 A1 | 2/2015 | Van Hoff et al. | |
| 2015/0070274 A1 | 3/2015 | Morozov | |
| 2015/0230040 A1 | 8/2015 | Squires et al. | |
| 2016/0124707 A1 | 5/2016 | Ermilov et al. | |
| 2016/0134988 A1* | 5/2016 | Gorzel | G10L 19/00 381/22 |
| 2016/0227340 A1 | 8/2016 | Peters et al. | |
| 2016/0241980 A1 | 8/2016 | Najaf-Zadeh et al. | |
| 2016/0269712 A1 | 9/2016 | Ostrover et al. | |
| 2016/0337630 A1 | 11/2016 | Raghoebardajal et al. | |
| 2016/0373640 A1 | 12/2016 | Van Hoff et al. | |
| 2017/0098453 A1 | 4/2017 | Wright et al. | |
| 2017/0318360 A1 | 11/2017 | Tran et al. | |
| 2017/0332186 A1 | 11/2017 | Riggs et al. | |
| 2018/0220251 A1 | 8/2018 | Brettle et al. | |
| 2018/0253275 A1 | 9/2018 | Helwani et al. | |
| 2018/0300940 A1 | 10/2018 | Sakthivel et al. | |
| 2019/0005986 A1 | 1/2019 | Peters et al. | |

OTHER PUBLICATIONS

"Information technology—High efficiency coding and media delivery in heterogeneous environments—Part 3: 3D Audio," ISO/IEC JTC 1/SC 29N, ISO/IEC 23008-3; 201*(E), Oct. 12, 2016, 797 pp.
Rébillat M., et al., "SMART-I2: Spatial Multi-users Audio-visual Real Time Interactive Interface, a broadcast application context," 3DTV Conference: The True Vision—Capture, Transmission and Display of 3D Video, May 2009, Postdam, Germany, pp. 1-4.
Response to Written Opinion dated Mar. 6, 2018, from International Application No. PCT/US2018/013526, filed on Sep. 12, 2018, 18 pp.
Second Written Opinion, dated Oct. 29, 2018, for International Application No. PCT/US2018/013526, 8 pp.
International Search Report and Written Opinion—PCT/US2018/013526—ISA/EPO—Mar. 6, 2018, 16 pp.
"Call for Proposals for 3D Audio," ISO/IEC JTC1/SC29/WG11/N13411, Jan. 2013, 20 pp.
"Information technology—High efficiency coding and media delivery in heterogeneous environments—Part 3: Part 3: 3D Audio, Amendment 3: MPEG-H 3D Audio Phase 2," ISO/IEC JTC 1/SC 29N, Jul. 25, 2015, 208 pp.
"Information technology—High efficiency coding and media delivery in heterogeneous environments—Part 3: 3D Audio," ISO/IEC JTC 1/SC 29N, Apr. 4, 2014, 337 pp.
"Information technology—High efficiency coding and media delivery in heterogeneous environments—Part 3: 3D Audio," ISO/IEC JTC 1/SC 29, Jul. 25, 2014, 433 pp.
"Information technology—High efficiency coding and media delivery in heterogeneous environments—Part 3: 3D audio," ISO/IEC JTC 1/SC 29, ISO/IEC DIS 23008-3, Jul. 25, 2014, 311 pp.
"Information technology—High efficiency coding and media delivery in heterogeneous environments—Part 3: 3D Audio," ISO/IEC JTC 1/SC 29, ISO/IEC 23008-3:201x(E), Oct. 12, 2016, 797 pp.
Herre et al., "MPEG-H 3D Audio—The New Standard for Coding of Immersive Spatial Audio," IEEE Journal of Selected Topics in Signal Processing, vol. 9, No. 5, Aug. 2015, pp. 770-779.
Hollerweger et al., "An Introduction to Higher Order Ambisonic," Oct. 2008, 13 pp.
Poletti, "Three-Dimensional Surround Sound Systems Based on Spherical Harmonics," J. Audio Eng. Soc., vol. 53, No. 11, Nov. 2005, pp. 1004-1025.
Schonefeld, "Spherical Harmonics," Jul. 1, 2005, Accessed online [Jul. 9, 2013] at URL:http://videoarch1.s-inf.de/~volker/prosem_paper.pdf., 25 pp.
Sen et al., "RM1-HOA Working Draft Text," MPEG Meeting; Jan. 13-17, 2014; San Jose, CA; (Motion Picture Expert Group or ISO/IEC JTC1/SC2/WG11), No. M31827, XP030060280, 83 pp.
Sen et al., "Technical Description of the Qualcomm's HOA Coding Technology for Phase II," ISO/IEC JTC/SC29/WG11 MPEG 2014/M34104, Jul. 2014, 4 pp.
Tingvall J., "Interior Design and Navigation in Virtual Reality," Information Coding, last updated Nov. 30, 2015, accessed from [http://liu.divaportal.org/smash/record.jsf?pid=diva2%3A8750948,dswid=6015], 88 pp.
Van Gelderen M., "The shift operators and translations of spherical harmonics," DEOS Progress Letter 1998.1:57-67, accessed on Jul. 11, 2017, 11 pp.
Lavalle S.M., et al., "Head Tracking for the Oculus Rift," Oculus VR, Inc., accessed on Aug. 17, 2017, 8 pp.
Peterson et al., "Virtual Reality, Augmented Reality, and Mixed Reality Definitions," EMA, version 1.0, Jul. 7, 2017,4 pp.
U.S. Appl. No. 15/672,058, filed by Nils Gunther Peters, filed Aug. 8, 2017.
U.S. Appl. No. 15/782,252, filed by Nils Gunther Peters, filed Oct. 12, 2017.
Porschmann C., et al.,"3-D Audio in Mobile Communication Devices: Methods for Mobile Head-Tracking," Journal of Virtual Reality and Broadcasting, 2007, vol. 4, No. 13, 14 pages.
Tylka J.G., et al., "Comparison of Techniques for Binaural Navigation of Higher-order Ambisonic Soundfields," AES Convention 139; Oct. 2015, AES, 60 East 42nd Street, Room 2520 New York 10165-2520, USA, Oct. 23, 2015, XP040672273, 13 pages.
International Preliminary Report on Patentability dated Mar. 11, 2019 from International Application No. PCT/US2018/013526, filed Sep. 12, 2018, 24 pages.

* cited by examiner

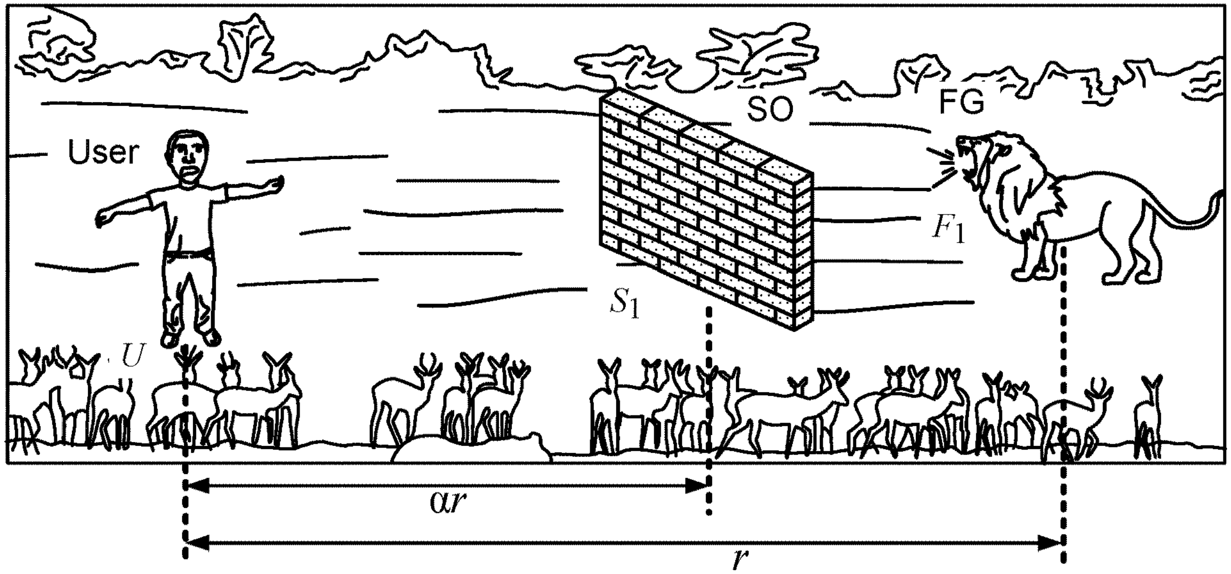

$$|U - F_1| \equiv r$$
$$|U - S_1| \equiv \alpha r \qquad \text{where } 0 \le \alpha \le 1$$
$$|S_1 - F_1| \equiv (1-\alpha)r$$

Frequency, FGs, BGs, SOs $$\rho_i \equiv \rho_i(f, F_1, \ldots, F_I, B_1, \ldots, B_J, S_1, \ldots, S_K)$$

In this example, there are two objects, $S_1$ and $F_1$.

FG sound is attenuated by SO as follows:

$$\rho_1 = w(f)(S_1)\left[-\frac{4x^2}{r^2} + \frac{4x}{r} + \beta\right]$$

Attenuation threshold where $x = \alpha r$ and $0 \le \alpha \le 1$

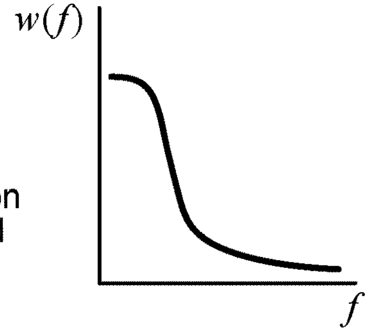

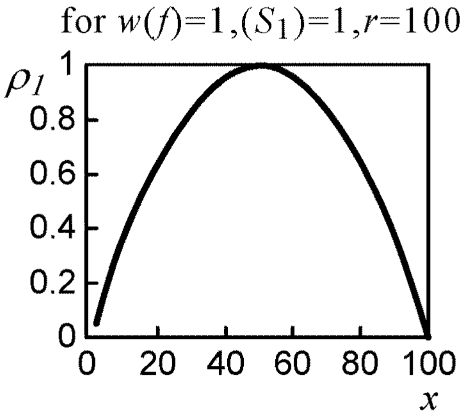

FIG. 11

AUDIO PARALLAX FOR VIRTUAL REALITY, AUGMENTED REALITY, AND MIXED REALITY

This application claims the benefit of U.S. Provisional Application No. 62/446,324 filed 13 Jan. 2017, the entire content of which is incorporated by reference herein.

TECHNICAL FIELD

The disclosure relates to the encoding and decoding of audio data and, more particularly, audio data coding techniques for virtual reality and augmented reality environments.

BACKGROUND

Various technologies have been developed that allow a person to sense and interact with a computer-generated environment, often through visual and sound effects provided to the person or persons by the devices providing the computer-generated environment. These computer-generated environments are sometimes referred to as "virtual reality" or "VR" environments. For example, a user may avail of a VR experience using one or more wearable devices, such as a headset. A VR headset may include various output components, such as a display screen that provides visual images to the user, and speakers that output sounds. In some examples, a VR headset may provide additional sensory effects, such as tactile sensations provided by way of movement or vibrations. In some examples, the computer-generated environment may provide audio effects to a user or users through speakers or other devices not necessarily worn by the user, but rather, where the user is positioned within audible range of the speakers. Similarly, head-mounted displays (HMDs) exist that allow a user to see the real world in front of the user (as the lenses are transparent) and to see graphic overlays (e.g., from projectors embedded in the HMD frame), as a form of "augmented reality" or "AR." Similarly, systems exist that allow a user to experience the real world with the addition to VR elements, as a form of "mixed reality" or "MR."

VR, MR, and AR systems may incorporate capabilities to render higher-order ambisonics (HOA) signals, which are often represented by a plurality of spherical harmonic coefficients (SHC) or other hierarchical elements. That is, the HOA signals that are rendered by a VR, MR, or AR system may represent a three dimensional (3D) soundfield. The HOA or SHC representation may represent the 3D soundfield in a manner that is independent of the local speaker geometry used to playback a multi-channel audio signal rendered from the SHC signal. The SHC signal may also facilitate backwards compatibility as the SHC signal may be rendered to well-known and highly adopted multi-channel formats, such as a 5.1 audio channel format or a 7.1 audio channel format. The SHC representation may therefore enable a better representation of a soundfield that also accommodates backward compatibility.

SUMMARY

In general, techniques are described by which audio decoding devices and audio encoding devices may leverage video data from a computer-generated environment's video feed, to provide a more accurate representation of the 3D soundfield associated with the computer-generated reality experience. Generally, the techniques of this disclosure may enable various systems to adjust audio objects in the HOA domain to generate a more accurate representation of the energies and directional components of the audio data upon rendering. As one example, the techniques may enable rendering the 3D soundfield to accommodate a six degree-of-freedom (6-DOR) capability of the computer-generated reality system. Moreover, the techniques of this disclosure enable the rendering devices to use data represented in the HOA domain to alter audio data based on characteristics of the video feed being provided for the computer-generated reality experience.

For instance, according to the techniques described herein, the audio rendering device of the computer-generated reality system may adjust foreground audio objects for parallax-related changes that stem from "silent objects" that may attenuate the foreground audio objects. As another example, the techniques of this disclosure may enable the audio rendering device of the computer-generated reality system to determine relative distances between the user and a particular foreground audio object. As another example, the techniques of this disclosure may enable the audio rendering device to apply transmission factors to render the 3D soundfield to provide a more accurate computer-generated reality experience to a user.

In one example, this disclosure is directed to an audio decoding device. The audio decoding device may include processing circuitry and a memory device coupled to the processing circuitry. The processing circuitry is configured to receive, in a bitstream, encoded representations of audio objects of a three-dimensional (3D) soundfield, to receive metadata associated with the bitstream, to obtain, from the received metadata, one or more transmission factors associated with one or more of the audio objects, and to apply the transmission factors to the one or more audio objects to obtain parallax-adjusted audio objects of the 3D soundfield. The memory device is configured to store at least a portion of the received bitstream, the received metadata, or the parallax-adjusted audio objects of the 3D soundfield.

In another example, this disclosure is directed to a method that includes receiving, in a bitstream, encoded representations of audio objects of a three-dimensional (3D) soundfield, and receiving metadata associated with the bitstream. The method may further include obtaining, from the received metadata, one or more transmission factors associated with one or more of the audio objects, and applying the transmission factors to the one or more audio objects to obtain parallax-adjusted audio objects of the 3D soundfield.

In another example, this disclosure is directed to an audio decoding apparatus. The audio decoding apparatus may include means for receiving, in a bitstream, encoded representations of audio objects of a three-dimensional (3D) soundfield, and means for receiving metadata associated with the bitstream. The audio decoding apparatus may further include means for obtaining, from the received metadata, one or more transmission factors associated with one or more of the audio objects, and means for applying the transmission factors to the one or more audio objects to obtain parallax-adjusted audio objects of the 3D soundfield.

In another example, this disclosure is directed to a non-transitory computer-readable storage medium encoded with instructions. The instructions, when executed, cause processing circuitry of an audio decoding device to receive, in a bitstream, encoded representations of audio objects of a three-dimensional (3D) soundfield, and to receive metadata associated with the bitstream. The instructions, when executed, further cause the processing circuitry of the audio decoding device to obtain, from the received metadata, one or more transmission factors associated with one or more of the audio objects, and to apply the transmission factors to the one or more audio objects to obtain parallax-adjusted audio objects of the 3D soundfield.

The details of one or more aspects of the techniques are set forth in the accompanying drawings and the description below. Other features, objects, and advantages of these techniques will be apparent from the description and drawings, and from the claims.

BRIEF DESCRIPTION OF DRAWINGS

FIG. 11 is a diagram illustrating aspects of transmission factor calculations that an audio encoding device may perform, in accordance with one or more techniques of this disclosure.

DETAILED DESCRIPTION

Figure 1:
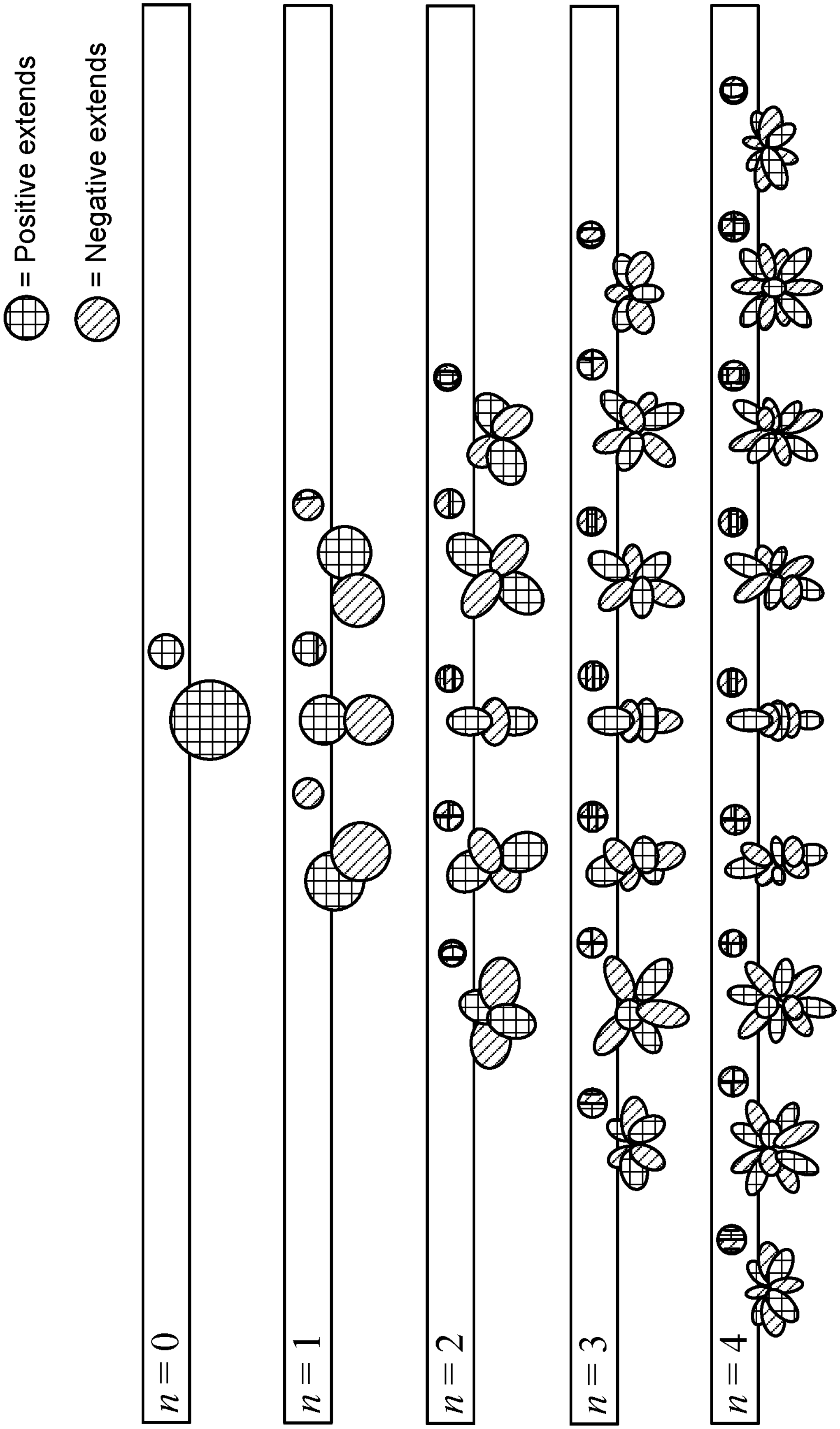
FIG. 1 is a diagram illustrating spherical harmonic basis functions from the zero order (n=0) to the fourth order (n=4).

In some aspects, this disclosure describes techniques by which audio decoding devices and audio encoding devices may leverage video data from a VR, MR, or AR video feed to provide a more accurate representation of the 3D soundfield associated with the VR/MR/AR experience. For instance, techniques of this disclosure may enable various systems to adjust audio objects in the HOA domain to generate a more accurate representation of the energies and directional components of the audio data upon rendering. As one example, the techniques may enable rendering the 3D soundfield to accommodate a six degree-of-freedom (6-DOR) capability of the VR system.

Moreover, the techniques of this disclosure enable the rendering devices to use HOA domain data to alter audio data based on characteristics of the video feed being provided for the VR experience. For instance, according to the techniques described herein, the audio rendering device of the VR system may adjust foreground audio objects for parallax-related changes that stem from "silent objects" that may attenuate the foreground audio objects. As another example, the techniques of this disclosure may enable the audio rendering device of the VR system to determine relative distances between the user and a particular foreground audio object.

Surround sound technology may be particularly suited to incorporation into VR systems. For instance, the immersive audio experience provided by surround sound technology complements the immersive video and sensory experience provided by other aspects of VR systems. Moreover, augmenting the energy of audio objects with directional characteristics as provided by ambisonics technology provides for a more realistic simulation by the VR environment. For instance, the combination of realistic placement of visual objects in combination with corresponding placement of audio objects via the surround sound speaker array may more accurately simulate the environment that is being replicated.

There are various 'surround-sound' channel-based formats in the market. They range, for example, from the 5.1 home theatre system (which has been the most successful in terms of making inroads into living rooms beyond stereo) to the 22.2 system developed by NHK (Nippon Hoso Kyokai or Japan Broadcasting Corporation). Content creators (e.g., Hollywood studios) would like to produce the soundtrack for a movie once, and not spend effort to remix it for each speaker configuration. A Moving Pictures Expert Group (MPEG) has released a standard allowing for soundfields to be represented using a hierarchical set of elements (e.g., Higher-Order Ambisonic—HOA—coefficients) that can be rendered to speaker feeds for most speaker configurations, including 5.1 and 22.2 configuration whether in location defined by various standards or in non-uniform locations.

MPEG released the standard as MPEG-H 3D Audio standard, formally entitled "Information technology—High efficiency coding and media delivery in heterogeneous environments—Part 3: 3D audio," set forth by ISO/IEC JTC 1/SC 29, with document identifier ISO/IEC DIS 23008-3, and dated Jul. 25, 2014. MPEG also released a second edition of the 3D Audio standard, entitled "Information technology—High efficiency coding and media delivery in heterogeneous environments—Part 3: 3D audio, set forth by ISO/IEC JTC 1/SC 29, with document identifier ISO/IEC 23008-3:201x(E), and dated Oct. 12, 2016. Reference to the "3D Audio standard" in this disclosure may refer to one or both of the above standards.

As noted above, one example of a hierarchical set of elements is a set of spherical harmonic coefficients (SHC). The following expression demonstrates a description or representation of a soundfield using SHC:

$$p_i(t, r_r, \theta_r, \varphi_r) = \sum_{\omega=0}^{\infty}\left[4\pi\sum_{n=0}^{\infty} j_n(kr_r)\sum_{m=-n}^{n} A_n^m(k)Y_n^m(\theta_r, \varphi_r)\right]e^{j\omega t},$$

The expression shows that the pressure $p_i$ at any point $\{r_r, \theta_r, \varphi_r\}$ of the soundfield, at time t, can be represented uniquely by the SHC, $A_n^m(k)$. Here, $$k = \frac{\omega}{c},$$

c is the speed of sound (~343 m/s), $\{r_r, \theta_r, \varphi_r\}$ is a point of reference (or observation point), $j_n(\cdot)$ is the spherical Bessel function of order n, and $Y_n^m(\theta_r, \varphi_r)$ are the spherical harmonic basis functions (which may also be referred to as a spherical basis function) of order n and suborder m. It can be recognized that the term in square brackets is a frequency-domain representation of the signal (i.e., $S(\omega, r_r, \theta_r, \varphi_r)$) which can be approximated by various time-frequency transformations, such as the discrete Fourier transform (DFT), the discrete cosine transform (DCT), or a wavelet transform. Other examples of hierarchical sets include sets of wavelet transform coefficients and other sets of coefficients of multiresolution basis functions.

FIG. 1 is a diagram illustrating spherical harmonic basis functions from the zero order (n=0) to the fourth order (n=4). As can be seen, for each order, there is an expansion of suborders m which are shown but not explicitly noted in the example of FIG. 1 for ease of illustration purposes.

The SHC $A_n^m(k)$ can either be physically acquired (e.g., recorded) by various microphone array configurations or, alternatively, they can be derived from channel-based or object-based descriptions of the soundfield. The SHC (which also may be referred to as higher order ambisonic—HOA—coefficients) represent scene-based audio, where the SHC may be input to an audio encoder to obtain encoded SHC that may promote more efficient transmission or storage. For example, a fourth-order representation involving $(1+4)^2$ (25, and hence fourth order) coefficients may be used.

As noted above, the SHC may be derived from a microphone recording using a microphone array. Various examples of how SHC may be derived from microphone arrays are described in Poletti, M., "Three-Dimensional Surround Sound Systems Based on Spherical Harmonics," J. Audio Eng. Soc., Vol. 53, No. 11, 2005 November, pp. 1004-1025.

To illustrate how the SHCs may be derived from an object-based description, consider the following equation. The coefficients $A_n^m(k)$ for the soundfield corresponding to an individual audio object may be expressed as:

$$A_n^m(k)=g(\omega)(-4\pi ik)h_n^{(2)}(kr_s)Y_n^{m*}(\theta_s,\varphi_s),$$

where i is $\sqrt{-1}$, $h_n^{(2)}(\cdot)$ is the spherical Hankel function (of the second kind) of order n, and $\{r_s, \theta_s, \varphi_s\}$ is the location of the object. Knowing the object source energy $g(\omega)$ as a function of frequency (e.g., using time-frequency analysis techniques, such as performing a fast Fourier transform on the PCM stream) allows us to convert each PCM object and the corresponding location into the SHC $A_n^m(k)$. Further, it can be shown (since the above is a linear and orthogonal decomposition) that the $A_n^m(k)$ coefficients for each object are additive. In this manner, a number of PCM objects can be represented by the $A_n^m(k)$ coefficients (e.g., as a sum of the coefficient vectors for the individual objects). Essentially, the coefficients contain information about the soundfield (the pressure as a function of 3D coordinates), and the above represents the transformation from individual objects to a representation of the overall soundfield, in the vicinity of the observation point $\{r_r, \theta_r, \varphi_r\}$. The remaining figures are described below in the context of SHC-based audio coding.

Figure 2A:
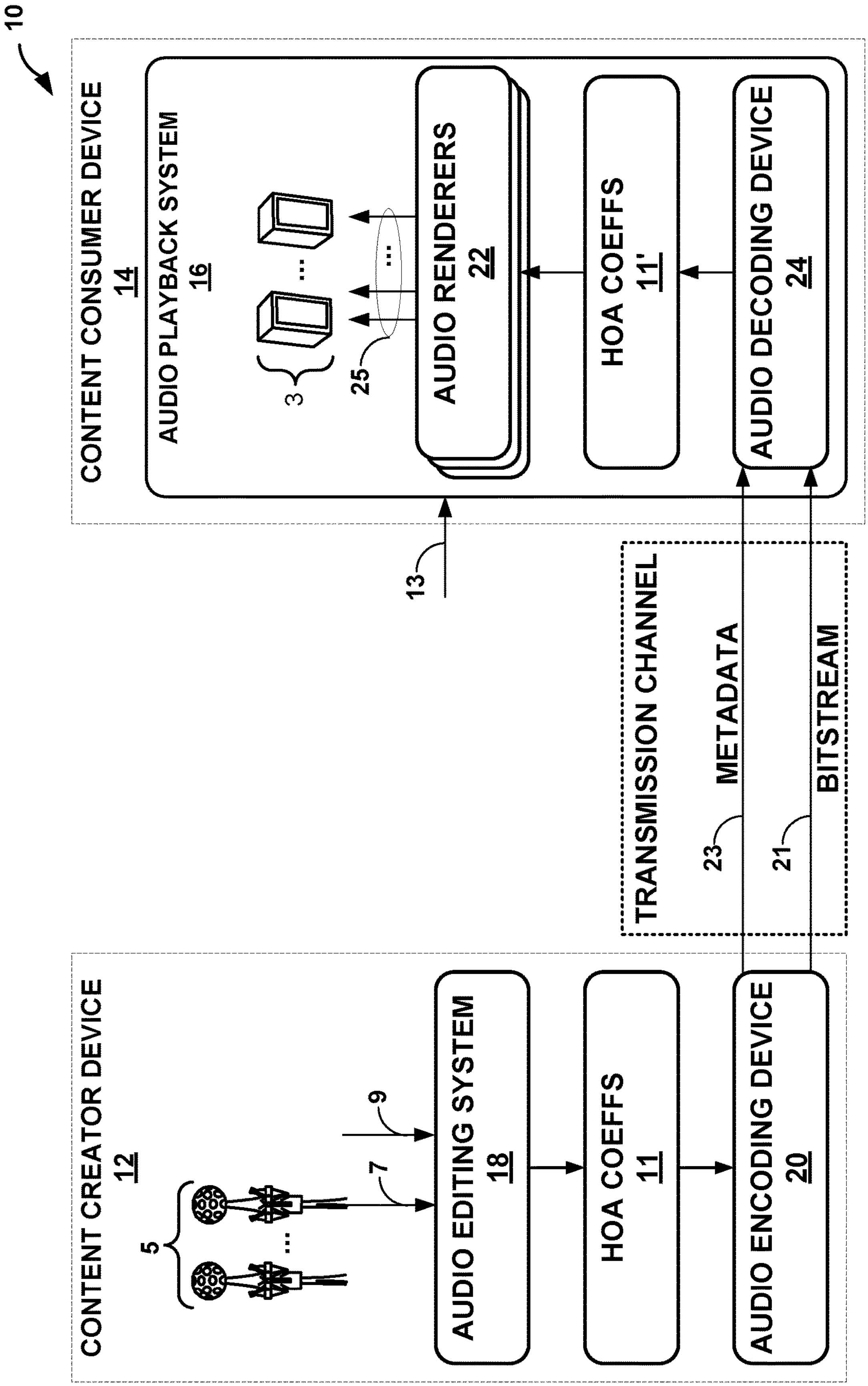
FIG. 2A is a diagram illustrating a system that may perform various aspects of the techniques described in this disclosure.

FIG. 2A is a diagram illustrating a system 10A that may perform various aspects of the techniques described in this disclosure. As shown in the example of FIG. 2A, the system 10A includes a content creator device 12 and a content consumer device 14. While described in the context of the content creator device 12 and the content consumer device 14, the techniques may be implemented in any context in which SHCs (which may also be referred to as HOA coefficients) or any other hierarchical representation of a soundfield are encoded to form a bitstream representative of the audio data. Moreover, the content creator device 12 may represent any form of computing device capable of implementing the techniques described in this disclosure, including a handset (or cellular phone), a tablet computer, a smart phone, or a desktop computer to provide a few examples. Likewise, the content consumer device 14 may represent any form of computing device capable of implementing the techniques described in this disclosure, including a handset (or cellular phone), a tablet computer, a smart phone, a set-top box, or a desktop computer to provide a few examples.

The content creator device 12 may be operated by a movie studio, game programmer, manufacturers of VR systems, or any other entity that may generate multi-channel audio content for consumption by operators of content consumer devices, such as the content consumer device 14. In some examples, the content creator device 12 may be operated by an individual user who would like to compress HOA coefficients 11. Often, the content creator device 12 generates audio content in conjunction with video content and/or content that can be expressed via tactile or haptic output. For instance, the content creator device 12 may include, be, or be part of a system that generates VR, MR, or AR environment data. The content consumer device 14 may be operated by an individual. The content consumer device 14 may include an audio playback system 16, which may refer to any form of audio playback system capable of rendering SHC for play back as multi-channel audio content.

For instance, the content consumer device 14 may include, be, or be part of a system that provides a VR, MR, or AR environment or experience to a user. As such, the content consumer device 14 may also include components for output of video data, for the output and input of tactile or haptic communications, etc. For ease of illustration purposes only, the content creator device 12 and the content consumer device 14 are illustrated in FIG. 2A using various audio-related components, although it will be appreciated that, in accordance with VR and AR technology, one or both devices may include additional components configured to process non-audio data (e.g., other sensory data), as well.

The content creator device 12 includes an audio editing system 18. The content creator device 12 obtain live recordings 7 in various formats (including directly as HOA coefficients) and audio objects 9, which the content creator device 12 may edit using audio editing system 18. Two or more microphones or microphone arrays (hereinafter, "microphones 5") may capture the live recordings 7. The content creator device 12 may, during the editing process, render HOA coefficients 11 from audio objects 9, listening to the rendered speaker feeds in an attempt to identify various aspects of the soundfield that require further editing. The content creator device 12 may then edit the HOA coefficients 11 (potentially indirectly through manipulation of different ones of the audio objects 9 from which the source HOA coefficients may be derived in the manner described above). The content creator device 12 may employ the audio editing system 18 to generate the HOA coefficients 11. The audio editing system 18 represents any system capable of editing audio data and outputting the audio data as one or more source spherical harmonic coefficients.

When the editing process is complete, the content creator device 12 may generate a bitstream 21 based on the HOA coefficients 11. That is, the content creator device 12 includes an audio encoding device 20 that represents a device configured to encode or otherwise compress HOA coefficients 11 in accordance with various aspects of the techniques described in this disclosure to generate the bitstream 21. The audio encoding device 20 may generate the bitstream 21 for transmission, as one example, across a transmission channel, which may be a wired or wireless channel, a data storage device, or the like. The bitstream 21 may represent an encoded version of the HOA coefficients 11 and may include a primary bitstream and another side bitstream, which may be referred to as side channel information. As shown in FIG. 2A, the audio encoding device 20 may also transmit metadata 23 over the transmission channel. In various examples, the audio encoding device 20 may generate the metadata 23 to include parallax-adjusting information with respect to the audio objects communicated via the bitstream 21. Although the metadata 23 is illustrated as being separate from the bitstream 21, the bitstream 21 may, in some examples, include the metadata 23.

According to techniques of this disclosure, the audio encoding device 20 may include, in the metadata 23, one or more of directional vector information, silent object information, and transmission factors for the HOA coefficients 11. For instance, the audio encoding device 20 may include transmission factors that, when applied, attenuate the energy of one or more of the HOA coefficients 11 communicated via the bitstream 21. In accordance with various aspects of this disclosure, the audio encoding device 20 may derive the transmission factors using object locations in video frames corresponding to the audio frames represented by the particular coefficients of the HOA coefficients 11. For instance, the audio encoding device 20 may determine that a silent object represented in the video data has a location that would interfere with the volume of certain foreground audio objects represented by the HOA coefficients 11, in a real-life scenario. In turn, the audio encoding device 20 may generate transmission factors that, when applied by the audio decoding device 24, would attenuate the energies of the HOA coefficients 11 to more accurately simulate the way the 3D soundfield would be heard by a listener in the corresponding video scene.

According to the techniques of this disclosure, the audio encoding device 20 may classify the audio objects 9, as expressed by the HOA coefficients 11, into foreground objects and background objects. For instance, the audio encoding device 20 may implement aspects of this disclosure to identify a silence object or silent object based on a determination that the object is represented in the video data, but does not correspond to a pre-identified audio object. Although described with respect to the audio encoding device 20 performing the video analysis, a video encoding device (not shown) or a dedicated visual analysis device or unit may perform the classification of the silent object, providing the classification and transmission factors to audio encoding device 20 for purposes of generating the metadata 23.

In the context of captured video and audio, the audio encoding device 20 may determine that an object does not correspond to a pre-identified audio object if the object is not equipped with a sensor. As used herein, the term "equipped with a sensor" may include scenarios where a sensor is attached (permanently or detachably) to an audio source, or placed within earshot (though not attached to) an audio source. If the sensor is not attached to the audio source but is positioned within earshot, then, in applicable scenarios, multiple audio sources that are within earshot of the sensor are considered to be "equipped" with the sensor. In a synthetic VR environment, the audio encoding device 20 may implement techniques of this disclosure to determine that an object does not correspond to a pre-identified audio object if the object in question does not map to any audio object in a predetermined list. In a combination recorded-synthesized VR or AR environment, the audio encoding device 20 may implement techniques of this disclosure to determine that an object does not correspond to a pre-identified audio object using one or both of the techniques described above.

Moreover, the audio encoding device 20 may determine relative foreground location information that reflects a relationship between the location of the listener and the respective locations of the foreground audio objects represented by the HOA coefficients 11 in the bitstream 21. For instance, the audio encoding device 20 may determine a relationship between the "first person" aspect of the video capture or video synthesis for the VR experience, and may determine the relationship between the location of the "first person" and the respective video object corresponding to each respective foreground audio object of the 3D soundfield.

In some examples, the audio encoding device 20 may also use the relative foreground location information to determine relative location information between the listener location and a silent object that attenuates the energy of the foreground object. For instance, the audio encoding device 20 may apply a scaling factor to the relative foreground location information, to derive the distance between the listener location and the silent object that attenuates the energy of the foreground audio object. The scaling factor may range in value from zero to one, with a zero value indicating that the silent object is co-located or substantially co-located with the listener location, and with the value of one indicating that the silent object is co-located or substantially co-located with the foreground audio object.

In some instances, the audio encoding device 20 may signal the relative foreground location information and/or the listener location-to-silent object distance information to the audio encoding device 24. In other examples, the audio encoding device 20 may signal the listener location information and the foreground audio object location information to the audio decoding device 24, thereby enabling the audio decoding device 24 to derive the relative foreground location information and/or the distance from the listener location to the silent object that attenuates the energy/directional data of the foreground audio object. While the metadata 23 and the bitstream 21 are illustrated in FIG. 2A as being signaled separately by the audio encoding device 20 as an example, it will be appreciated that, in some examples, the bitstream 21 may include portions or an entirety of the metadata 23. One or both of the audio encoding device 20 or the audio decoding device 24 may conform to a 3D audio standard, such as "Information technology—High efficiency coding and media delivery in heterogeneous environments" (ISO/IEC JTC 1/SC 29) or simply, the "MPEG-H" standard.

While shown in FIG. 2A as being directly transmitted to the content consumer device 14, the content creator device 12 may output the bitstream 21 to an intermediate device positioned between the content creator device 12 and the content consumer device 14. The intermediate device may store the bitstream 21 for later delivery to the content consumer device 14, which may request the bitstream. The intermediate device may comprise a file server, a web server, a desktop computer, a laptop computer, a tablet computer, a mobile phone, a smart phone, or any other device capable of storing the bitstream 21 for later retrieval by an audio decoder. The intermediate device may reside in a content delivery network capable of streaming the bitstream 21 (and possibly in conjunction with transmitting a corresponding video data bitstream) to subscribers, such as the content consumer device 14, requesting the bitstream 21.

Alternatively, the content creator device 12 may store the bitstream 21 to a storage medium, such as a compact disc, a digital video disc, a high definition video disc or other storage media, most of which are capable of being read by a computer and therefore may be referred to as computer-readable storage media or non-transitory computer-readable storage media. In this context, the transmission channel may refer to the channels by which content stored to the mediums are transmitted (and may include retail stores and other store-based delivery mechanism). In any event, the techniques of this disclosure should not therefore be limited in this respect to the example of FIG. 2A.

As further shown in the example of FIG. 2A, the content consumer device 14 includes the audio playback system 16. The audio playback system 16 may represent any audio playback system capable of playing back multi-channel audio data. The audio playback system 16 may include a number of different renderers 22. The renderers 22 may each provide for a different form of rendering, where the different forms of rendering may include one or more of the various ways of performing vector-base amplitude panning (VBAP), and/or one or more of the various ways of performing soundfield synthesis. As used herein, "A and/or B" means "A or B", or both "A and B".

The audio playback system 16 may further include an audio decoding device 24. The audio decoding device 24 may represent a device configured to decode HOA coefficients 11' from the bitstream 21, where the HOA coefficients 11' may be similar to the HOA coefficients 11 but differ due to lossy operations (e.g., quantization) and/or transmission via the transmission channel. The audio playback system 16 may, after decoding the bitstream 21 to obtain the HOA coefficients 11' and render the HOA coefficients 11' to output loudspeaker feeds 25. The loudspeaker feeds 25 may drive one or more loudspeakers (which are not shown in the example of FIG. 2A for ease of illustration purposes).

While described with respect to loudspeaker feeds 25, the audio playback system 16 may render headphone feeds from either the loudspeaker feeds 25 or directly from the HOA coefficients 11', outputting the headphone feeds to headphone speakers. The headphone feeds may represent binaural audio speaker feeds, which the audio playback system 16 renders using a binaural audio renderer.

To select the appropriate renderer or, in some instances, generate an appropriate renderer, the audio playback system 16 may obtain loudspeaker information 13 indicative of a number of loudspeakers and/or a spatial geometry of the loudspeakers. In some instances, the audio playback system 16 may obtain the loudspeaker information 13 using a reference microphone and driving the loudspeakers in such a manner as to dynamically determine the loudspeaker information 13. In other instances or in conjunction with the dynamic determination of the loudspeaker information 13, the audio playback system 16 may prompt a user to interface with the audio playback system 16 and input the loudspeaker information 13.

The audio playback system 16 may then select one of the audio renderers 22 based on the loudspeaker information 13. In some instances, the audio playback system 16 may, when none of the audio renderers 22 are within some threshold similarity measure (in terms of the loudspeaker geometry) to the loudspeaker geometry specified in the loudspeaker information 13, generate the one of audio renderers 22 based on the loudspeaker information 13. The audio playback system 16 may, in some instances, generate one of the audio renderers 22 based on the loudspeaker information 13 without first attempting to select an existing one of the audio renderers 22. One or more speakers 3 may then playback the rendered loudspeaker feeds 25.

The audio decoding device 24 may implement various techniques of this disclosure to perform parallax-based adjustments for the encoded representations of the audio objects received via the bitstream 21. For instance, the audio decoding device 24 may apply transmission factors included in the metadata 23 to one or more audio objects conveyed as encoded representations in the bitstream 21. In various examples, the audio decoding device 24 may attenuate the energies and/or adjust directional information with respect to the foreground audio objects, based on the transmission factors. In some examples, the audio decoding device 24 may also use the metadata 23 to obtain silence object location information and/or relative foreground location information that relates a listener's location to the foreground audio objects' respective locations. By attenuating the energy of the foreground audio objects and/or adjusting the directional information of the foreground audio objects using the transmission factors, the audio decoding device 24 may enable the content consumer device 14 to render audio data over the speakers 3 that provides a more realistic auditory experience as part of a VR experience that also provides video data and, optionally, other sensory data as well.

In some examples, the audio decoding device 24 may locally derive the relative foreground location information using information included in the metadata 23. For instance, the audio decoding device 24 may receive listener location information and foreground audio object locations in the metadata 23. In turn, the audio decoding device 24 may derive the relative foreground location information, such as by calculating a displacement between the listener location and the foreground audio location.

For example, the audio decoding device 24 may use a coordinate system to calculate the relative foreground location information, by using the coordinates of the listener location and the foreground audio locations as operands in a distance calculation function. In some examples, the audio decoding device 24 may also receive, as part of the metadata 23, a scaling factor that is applicable to the relative foreground location information. In some such examples, the audio decoding device 24 may apply the scaling factor to the relative foreground location information to calculate the distance between the listener location and a silence object that attenuates the energy or alters the directional information of the foreground audio object(s). While the metadata 23 and the bitstream 21 are illustrated in FIG. 2A as being received separately at the audio decoding device 24 as an example, it will be appreciated that, in some examples, the bitstream 21 may include portions or an entirety of the metadata 23.

Figure 2B:
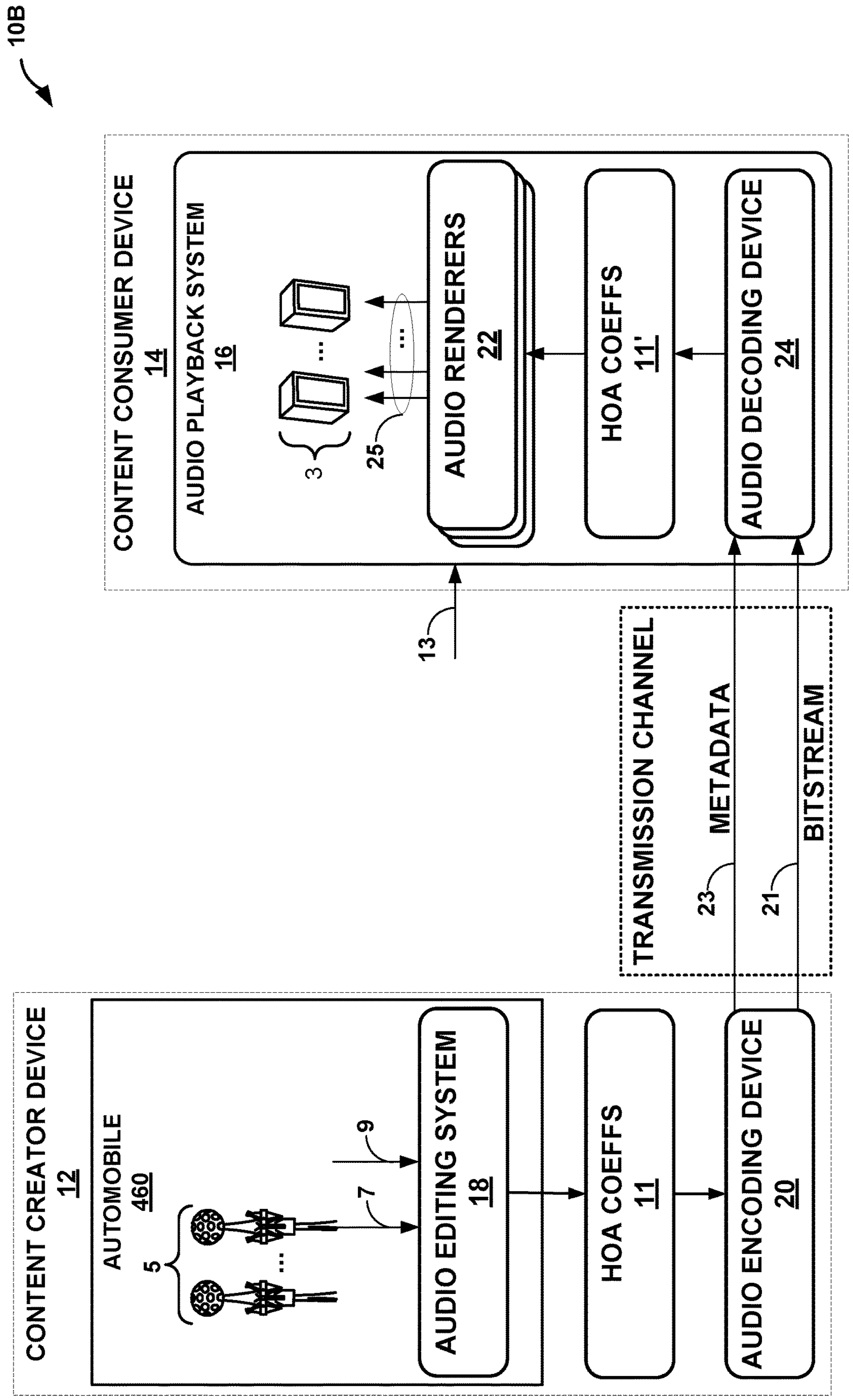
FIGS. 2B-2D are diagrams illustrating different examples of the system shown in the example of FIG. 2A.

The system 10B shown in FIG. 2B is similar to the system 10A shown in FIG. 2A, except that an automobile 460 includes the microphones 5. As such, some of the techniques set forth in this disclosure may be performed in the context of automobiles.

Figure 2C:
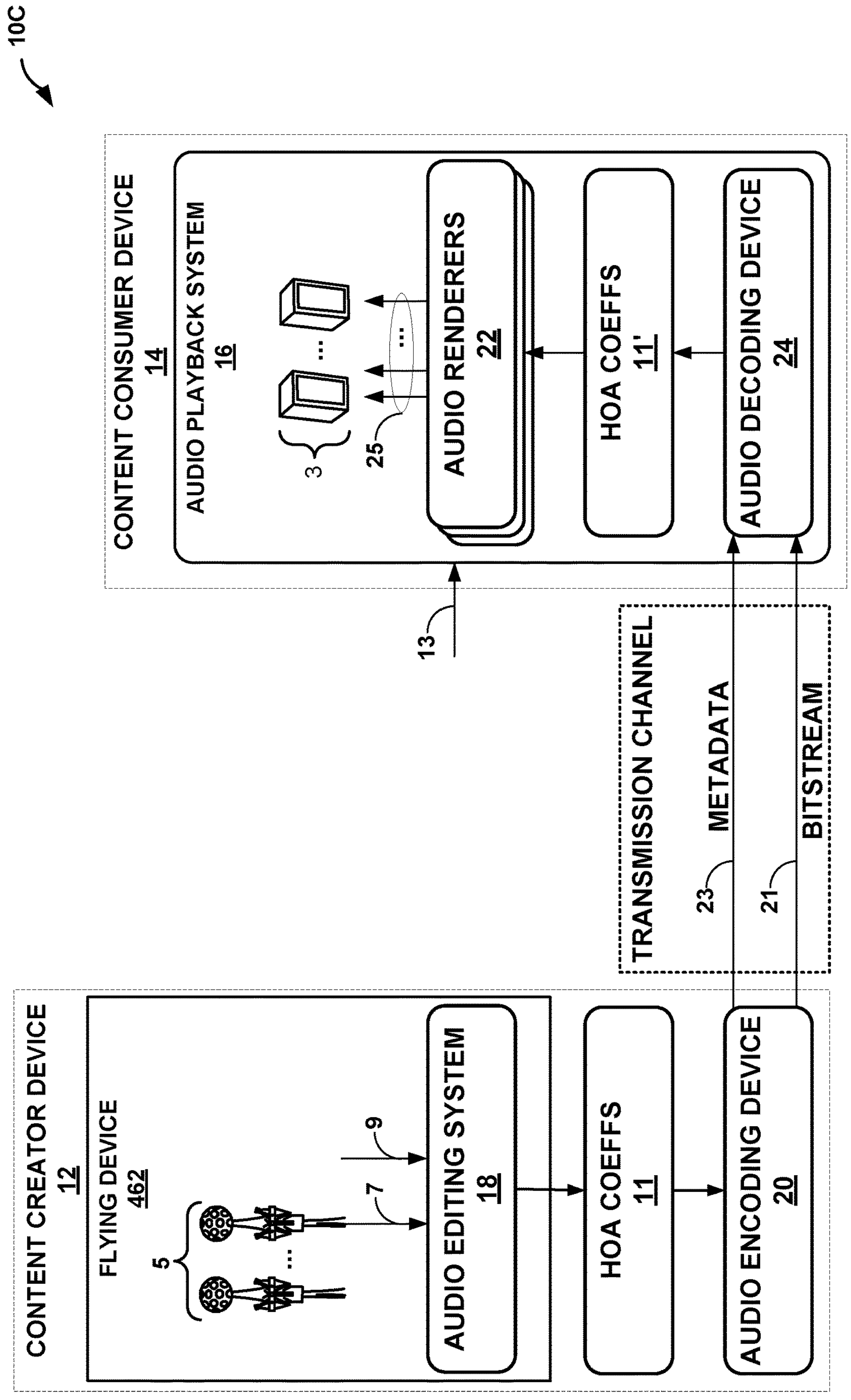

The system 10C shown in FIG. 2C is similar to the system 10A shown in FIG. 2A, except that a remotely-piloted and/or autonomous controlled flying device 462 includes the microphones 5. The flying device 462 may for example represent a quadcopter, a helicopter, or any other type of drone. As such, the techniques set forth in this disclosure may be performed in the context of drones.

Figure 2D:
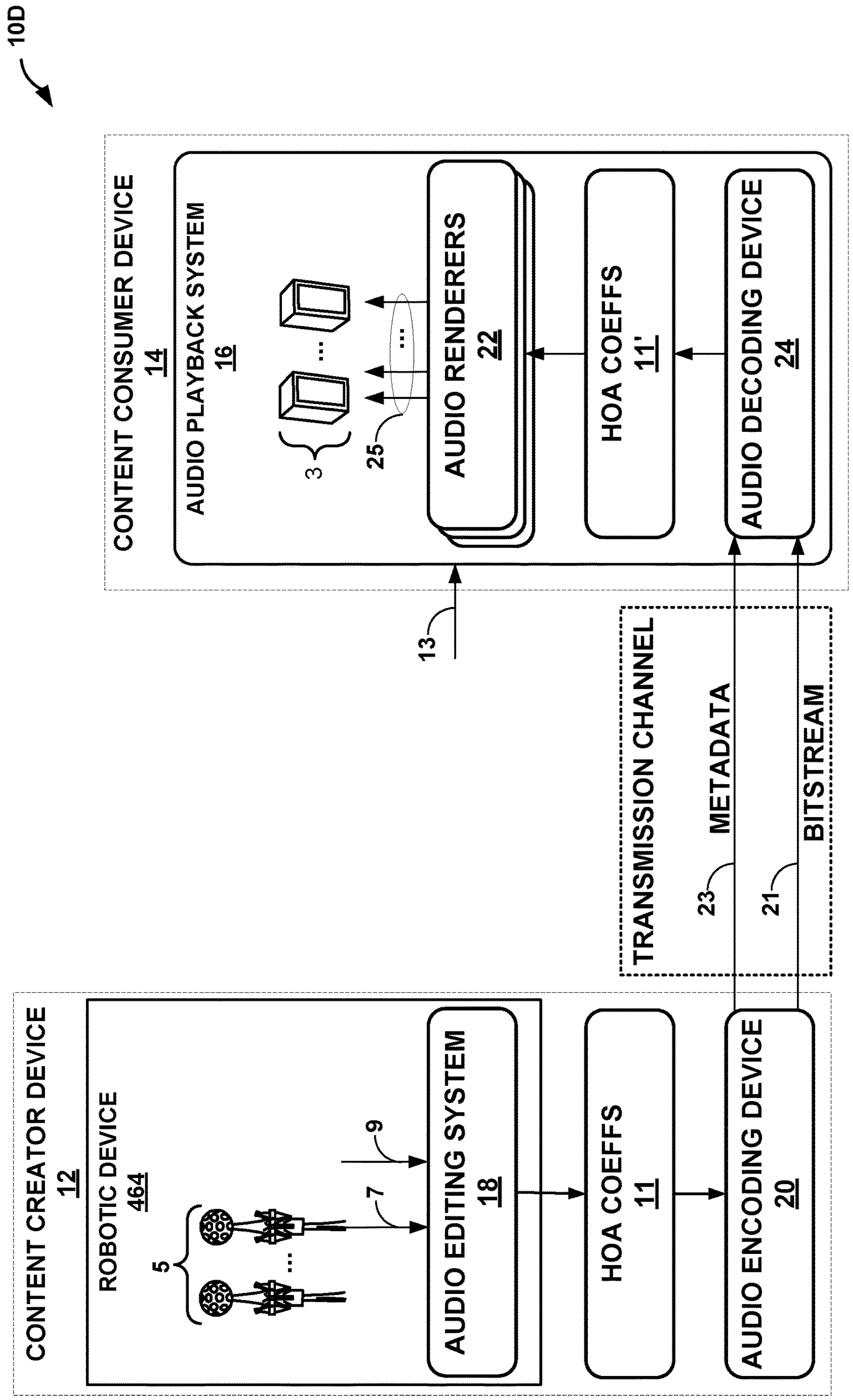

The system 10D shown in FIG. 2D is similar to the system 10A shown in FIG. 2A, except that a robotic device 464 includes the microphones 5. The robotic device 464 may for example represent a device that operates using artificial intelligence, or other types of robots. In some examples, the robotic device 464 may represent a flying device, such as a drone. In other examples, the robotic device 464 may represent other types of devices, including those that do not necessarily fly. As such, the techniques set forth in this disclosure may be performed in the context of robots.

Figure 3:
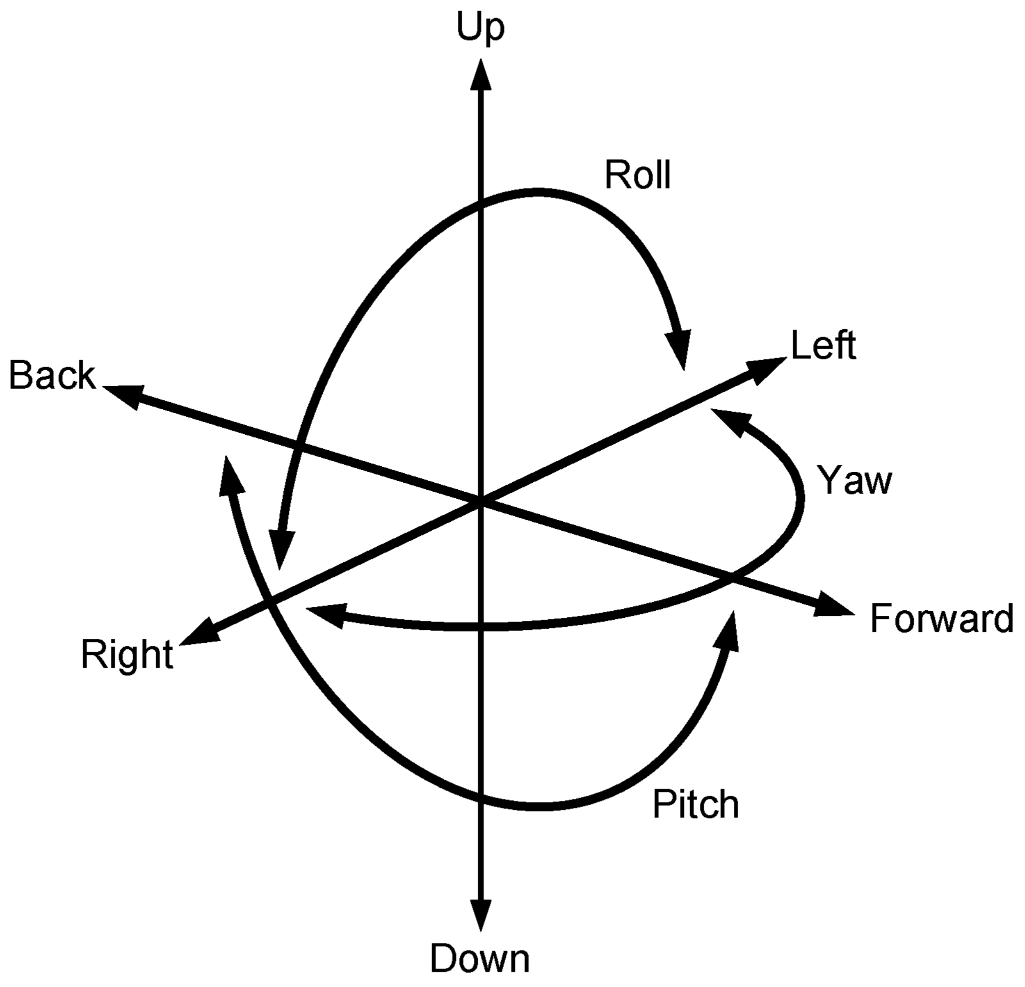
FIG. 3 is a diagram illustrating a six degree-of-freedom (6-DOF) head movement scheme for AVR and/or AR applications.

FIG. 3 is a diagram illustrating a six degree-of-freedom (6-DOF) head movement scheme for AVR and/or AR applications. Aspects of this disclosure address the rendering of 3D audio content in scenarios in which a listener receives 3D audio content, and if the listener moves within the 6-DOF confines illustrated in FIG. 3. In various examples, the listener may receive the 3D audio content by way of a device, such as in situations where the 3D audio content has been recorded and/or transmitted to a VR headset or AR HDM worn by the listener. In the example of FIG. 3, the listener may move his/her head according to rotation (e.g., as expressed by the pitch, yaw, and roll axes). The audio decoding device 24 illustrated in FIG. 2A may implement conventional HOA rendering to address head rotation along the pitch, yaw, and roll axes.

As shown in FIG. 3 however, the 6-DOF scheme includes three additional movement lines. More specifically, the 6-DOF scheme of FIG. 3 includes, in addition to the rotation axes discussed above, three lines along which the user's head position may translationally move, or actuate. The three translational directions are left-right (L/R), up-down (U/D), and forward-backward (F/B). The audio encoding device 20 and/or the audio decoding device 24 may use various techniques of this disclosure to implement parallax handling, to address the three translational directions. For instance, the audio decoding device 24 may apply one or more transmission factors to adjust the energies and/or directional information of various foreground audio objects to implement parallax adjustments based on the 6-DOF range of motion of a VR/AR user.

FIGS. 4A-4D are diagrams illustrating an example of parallax issues that may be presented in a VR scene 30. In the example of VR scene 30A of FIG. 4A, the listener's virtual position moves according to the first person account captured at or synthesized with respect to positions A, B, and C. At each of virtual positions A, B, and C, the listener may hear foreground audio objects associated with sounds emanating from the lion depicted at the right of FIG. 4A. Additionally, at each of virtual positions A, B, and C, the listener may hear foreground audio objects associated with sounds emanating from the running person depicted in the middle of FIG. 4A. Moreover, in a corresponding real-life situation, each of virtual positions A, B, and C, the listener may hear a different soundfield, due to different directional information and different occlusion or masking characteristics.

Figure 4A:
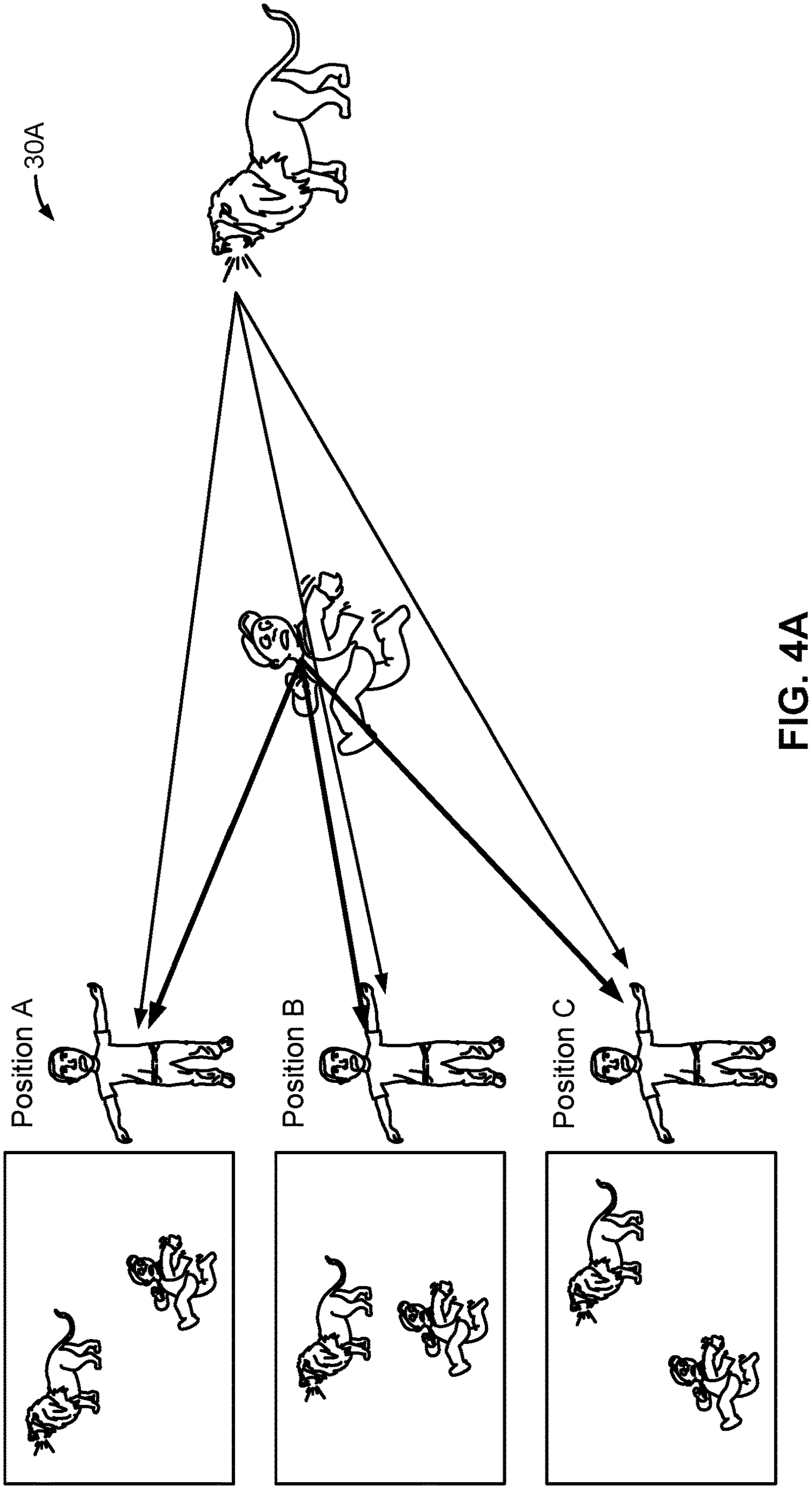
FIGS. 4A-4D are diagrams illustrating an example of parallax issues that may be presented in a VR scene.

The different occlusion/masking characteristics at each of virtual positions A, B, and C is illustrated in the left column of FIG. 4A. At virtual position A, the lion is roaring (e.g. producing foreground audio objects) behind and to the left of the running person. The audio encoding device 20 may perform beamforming to encode the aspects of the 3D soundfield experienced at virtual position A due to the interference of foreground audio objects (e.g., yelling) emanating from the position of the running person with the foreground audio objects (e.g., roaring) emanating from the position of the lion.

At virtual position B, the lion is roaring directly behind the running person. That is, the foreground audio objects related to the lion's roar are masked, to some degree, by the occlusion caused by the running person as well as by the masking caused by the yelling of the running person. The audio encoding device 20 may perform the masking based on the relative position of the listener (at the virtual position B) and the lion, as well as the distance between the running person and the listener (at the virtual position B).

For instance, the closer the running person is to the lion, the lesser the masking that the audio encoding device 20 may apply to the foreground audio objects of the lion's roar. The closer the running person is to the virtual position B where the listener is positioned, the greater the masking that the audio encoding device 20 may apply to the foreground audio objects of the lion's roar. The audio encoding device 20 may cease the masking to allow for some predetermined minimum energy with respect to the foreground audio objects of the lion's roar. That is, techniques of this disclosure enable the audio encoding device 20 to assign at least a minimum energy to the foreground audio objects of the lion's roar, regardless of how close the running person is to virtual position B, to accommodate some level of the lion's roar that will be heard at virtual position B.

Figure 4B:
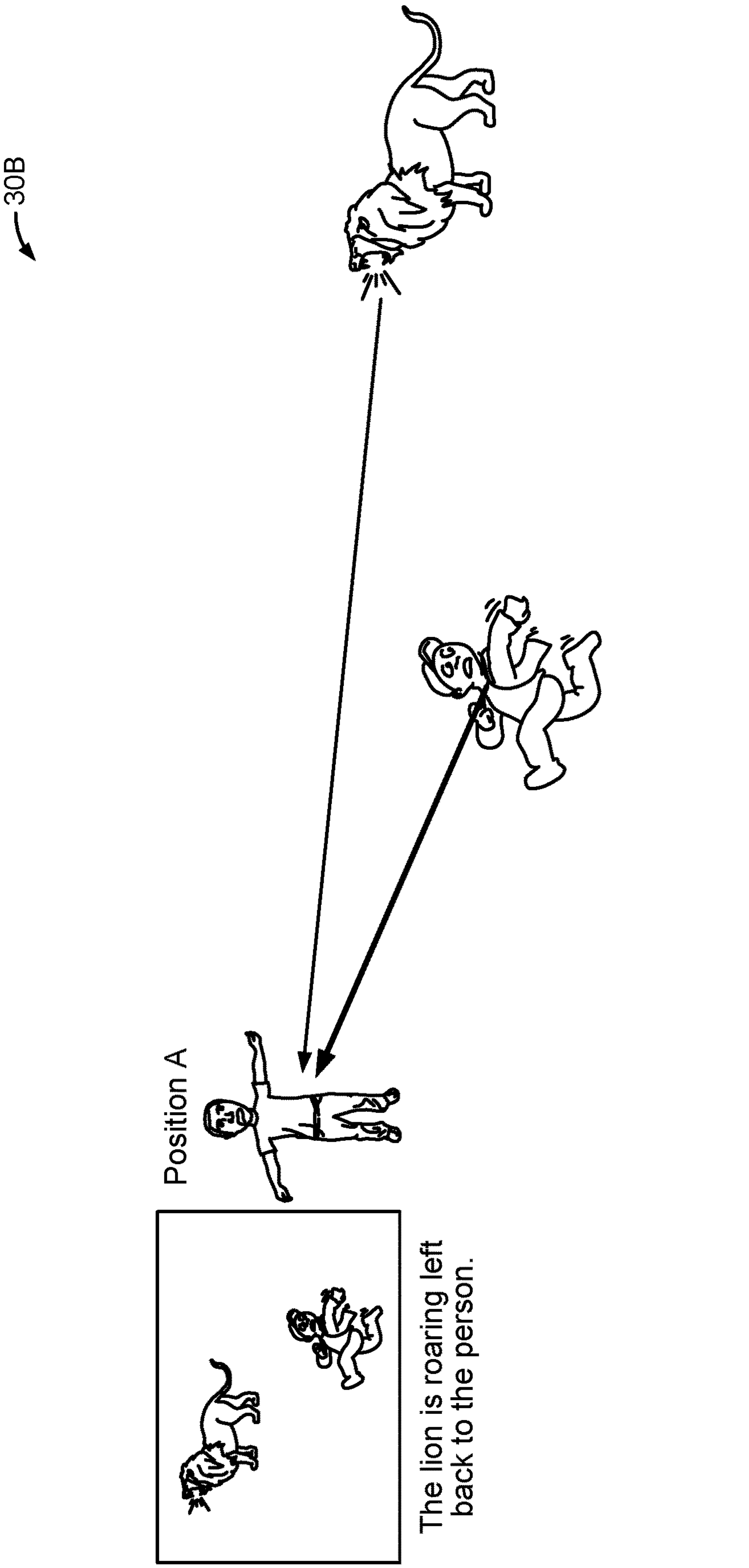

FIG. 4B illustrates the foreground audio objects' paths from the respective sources to virtual position A. Virtual scene 30B of FIG. 4B illustrates that the listener, at virtual position A, hears the lion's roar coming from behind and to the left of the running person.

Figure 4C:
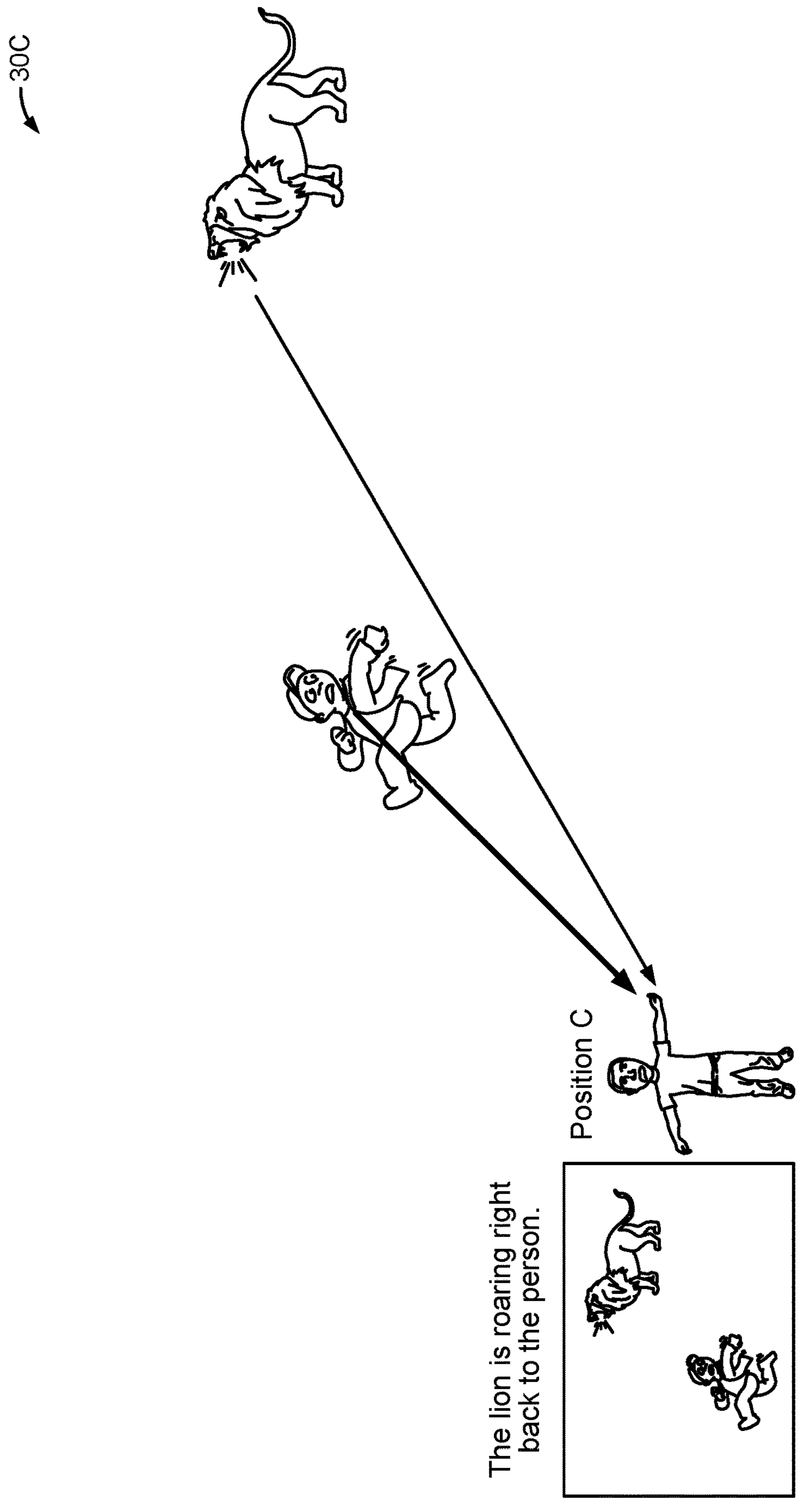

FIG. 4C illustrates the foreground audio objects' paths from the respective sources to virtual position C. Virtual scene 30C of FIG. 4C illustrates that the listener, at virtual position C, hears the lion's roar coming from behind and to the right of the running person.

Figure 4D:
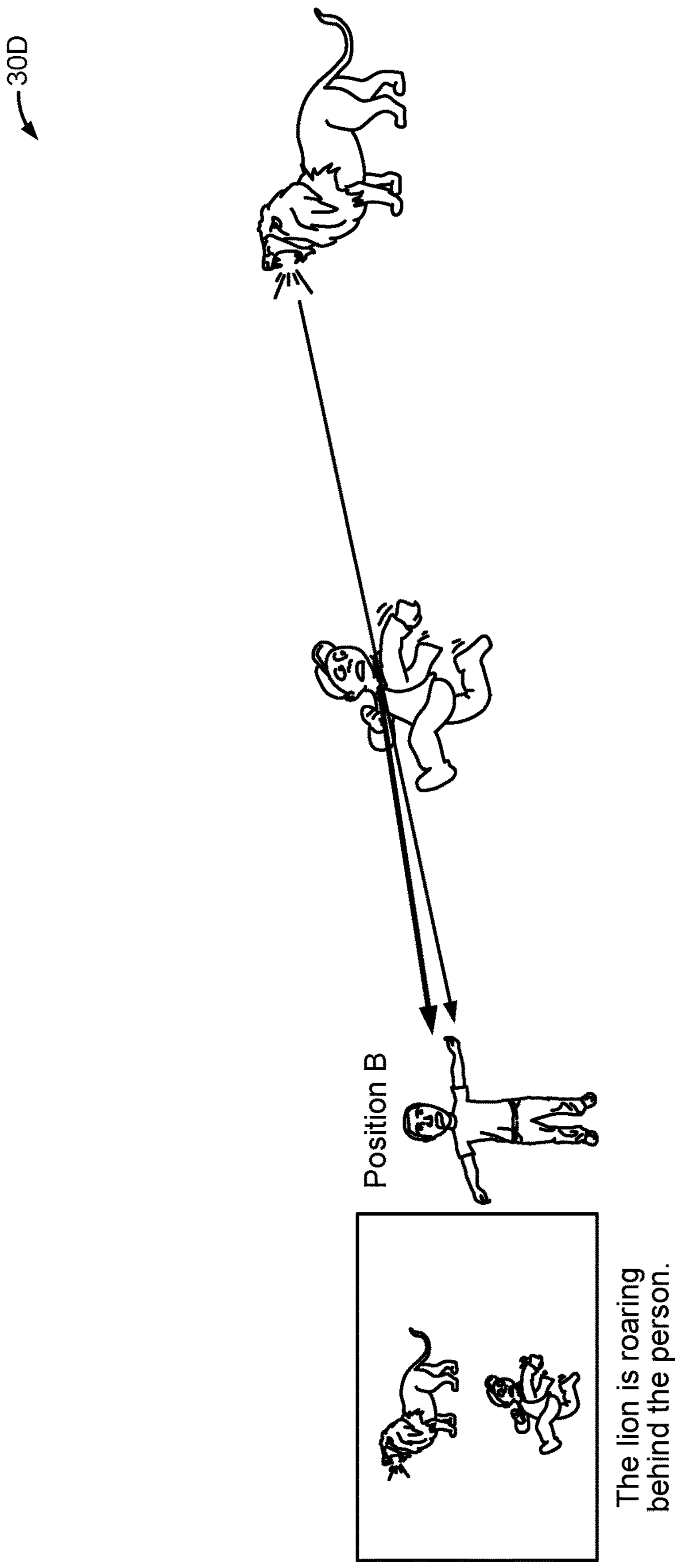

FIG. 4D illustrates the foreground audio objects' paths from the respective sources to virtual position B. Virtual scene 30D of FIG. 4D illustrates that the listener, at virtual position B, hears the lion's roar coming from directly behind the running person. In the case of virtual scene 30D illustrated in FIG. 4D, the audio encoding device 20 may implement masking based on all three of the listener's virtual position, the running person's position, and the lion's position being co-linear. For instance, the audio encoding device may adjust the loudness of the running person's yelling as well as the lion's roar based on the respective distances between every two of the three illustrated objects. For instance, the lion's roar may be masked by the sound of the running person's yell, as well as by the occlusion or physical blocking of the running person's body. The audio encoding device 20 may form various transmission factors based on the criteria discussed above, and may signal the transmission factors to the audio decoding device 24 within the metadata 23.

In turn, the audio decoding device 24 may apply the transmission factors in rendering the foreground audio objects associated with the lion's roar, to attenuate the loudness of the lion's roar based on the audio masking and physical occlusion caused by the running person. Additionally, the audio decoding device 24 may adjust the directional data of the foreground audio objects of the lion's roar, to account for the occlusion. For instance, the audio decoding device 24 may adjust the foreground audio objects of the lion's roar to simulate an experience at virtual position B in which the lion's roar is heard, at an attenuated loudness, from above and around the position of the running person's body.

Figure 5A:
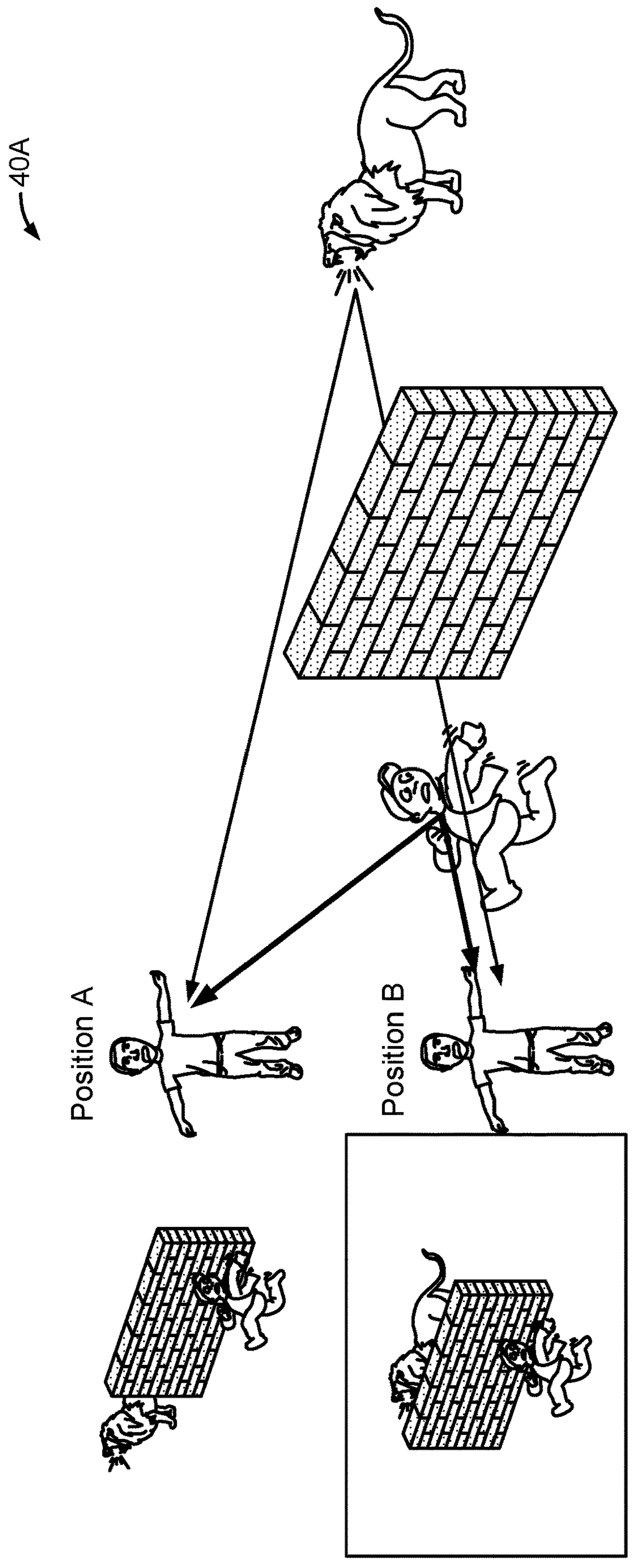
FIGS. 5A and 5B are diagrams illustrating another example of parallax issues that may be presented in a VR scene.
Figure 5B:
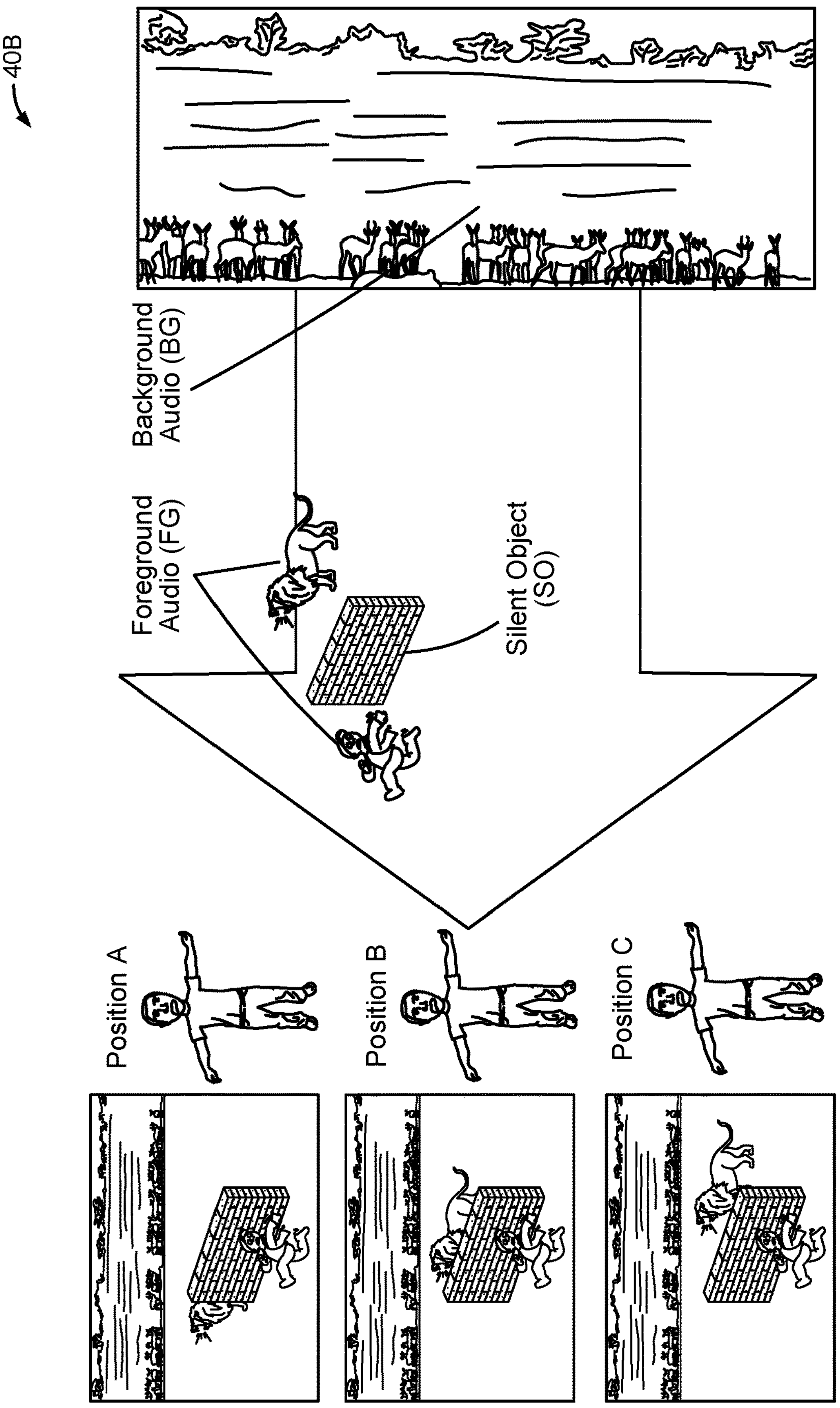

FIGS. 5A and 5B are diagrams illustrating another example of parallax issues that may be presented in a VR scene 40. In the example of VR scene 40A of FIG. 5A, the foreground audio objects of the lion's roar are, at some virtual positions, further occluded by the presence of a wall. In the example of FIG. 5A, the dimensions (e.g., width) of the wall prevent the wall from occluding the foreground audio objects of the lion's roar at virtual position A. However, the dimensions of the wall cause occlusion of the foreground audio objects of the lion's roar at virtual position B. In the left panel of FIG. 5A, the 3D soundfield effect at virtual position B is illustrated with a minimal display of the lion, to illustrate that some minimum energy is assigned to the foreground audio objects of the lion's roar, because some volume of the lion's roar can be heard at virtual position B, due to sound waves traveling over and (in some cases) around the wall.

The wall represents a "silent object" in the context of the techniques of this disclosure. As such, the presence of the wall is not directly indicated by audio objects captured by the microphones 5. Instead, the audio encoding device 20 may infer the locations of occlusion caused by the wall by leveraging video data captured by one or more cameras of (or coupled to) the content creator device 12. For instance, the audio encoding device 20 may translate the video scene position of the wall to audio position data, to represent the silent object ("SO") using HOA coefficients. Using the positional information of the SO derived in this fashion, the audio encoding device may form transmission factors with respect to the foreground audio objects of the lion's roar, with respect to the virtual position B.

Moreover, based on the relative positioning of the running person to the virtual position B and the SO, the audio encoding device 20 may not form transmission factors with respect to foreground audio objects of the yell of the running person. As shown, the SO is not positioned in such a way as to occlude the foreground audio objects of the running person with respect to the virtual position B. The audio encoding device 20 may signal the transmission factors (with respect to the foreground audio objects of the lion's roar) in the metadata 23 to the audio decoding device 24.

In turn, the audio decoding device 24 may apply the transmission factors received in the metadata 23 to the foreground audio objects associated with the lion's roar, with respect to a "sweet spot" position at virtual position B. By applying the transmission factors to the foreground audio objects of the lion's roar at the virtual position B, the audio decoding device 24 may attenuate the energy assigned to the foreground audio objects of the lion's roar, thereby simulating the occlusion caused by the presence of the SO. In this manner, the audio decoding device 24 may implement the techniques of this disclosure to apply transmission factors to render the 3D soundfield to provide a more accurate VR experience to a user of the content consumer device 14.

FIG. 5B illustrates virtual scene 40B, which includes the various features discussed with respect to the virtual scene 40A with respect to FIG. 5A, with additional details. For instance, the virtual scene 40B of FIG. 5B includes a source of background audio objects. In the example illustrated in FIG. 5B, the audio encoding device 20 may classify audio objects into SOs, foreground (FG) audio objects, and background (BG) audio objects. For instance, the audio encoding device 20 may identify a SO as an object that is represented in a video scene, but is not associated with any pre-identified audio object.

The audio encoding device 20 may identify a FG object as an audio object that is represented by an audio object in an audio frame, and is also associated with a pre-identified audio object. The audio encoding device 20 may identify a BG object as an audio object that is represented by an audio object in an audio frame, but is not associated with any pre-identified audio object. As used herein, an audio object may be associated with a pre-identified audio object if the audio object is associated with an object that is equipped with a sensor (in case of captured audio/video) or maps to an object in a predetermined list (e.g., in case of synthetic audio/video). The BG audio objects may not change or translate based on listener moving between virtual positions A-C. As discussed above, the SO may not generate audio objects of its own, but is used by the audio encoding device 20 to determine transmission factors for the attenuation of the FG objects. As such, the audio encoding device 20 may represent the FG and BG objects separately in the bitstream 21. As discussed above, the audio encoding device 20 may represent the transmission factors derived from the SO in the metadata 23.

Figure 6A:
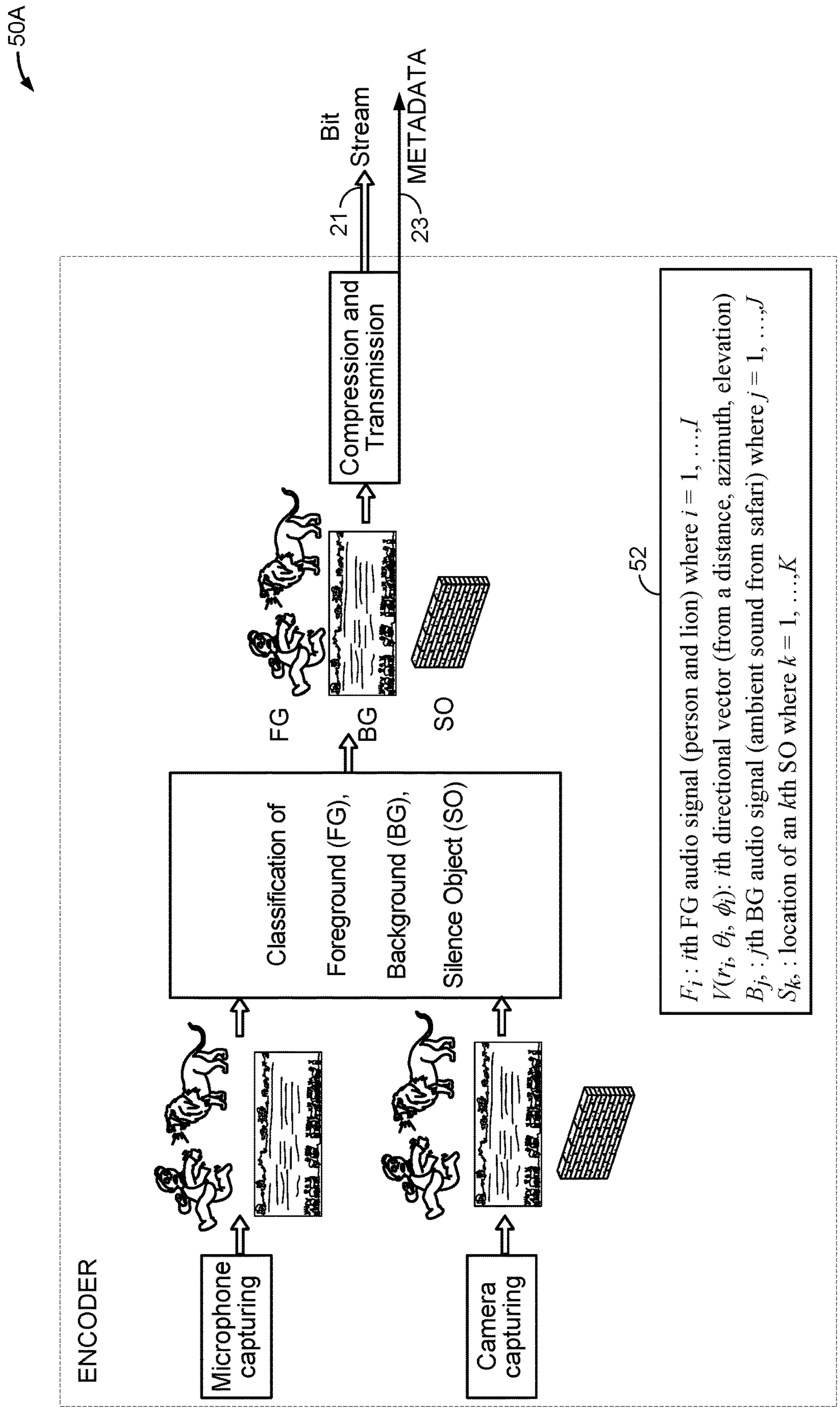
FIGS. 6A-6D are flow diagrams illustrating various encoder-side techniques of this disclosure.

FIGS. 6A-6D are flow diagrams illustrating various encoder-side techniques of this disclosure. FIG. 6A illustrates an encoding process 50A that the audio encoding device 20 may perform in an instance where the audio encoding device 20 processes a live recording, and in which the audio encoding device 20 performs compression and transmission functions. In the example of process 50A, the audio encoding device may process audio data captured via the microphones 5, and may also leverage data extracted from video data captured via one or more cameras. In turn, the audio encoding device 20 may classify the audio objects represented by the HOA coefficients 11 into FG objects, BG objects, and SOs. In turn, the audio encoding device 20 may compress the audio objects (e.g., by removing redundancies from the HOA coefficients 11), and transmit the bitstream 21 to represent the FG objects and BG objects. The audio encoding device 20 may also transmit the metadata 23 to represent transmission factors that the audio encoding device derives using the SOs.

As shown in the legend 52 of FIG. 6A, the audio encoding device may transmit the following data:

$F_i$: ith FG audio signal (person and lion) where i=1,Λ,I $V(r_i,\theta_i,\phi_i)$: ith directional vector (from a distance, azimuth, elevation)

$B_j$: jth BG audio signal (ambient sound from safari) where j=1,Λ,J $S_k$: location of an kth SO where k=1,Λ,K In various examples, the audio encoding device 20 may transmit one or more of the V vector calculation (with its parameters/arguments), and the $S_k$ value in the metadata 23. The audio encoding device may transmit the values of $F_i$ and $B_j$ in the bitstream 21.

Figure 6B:
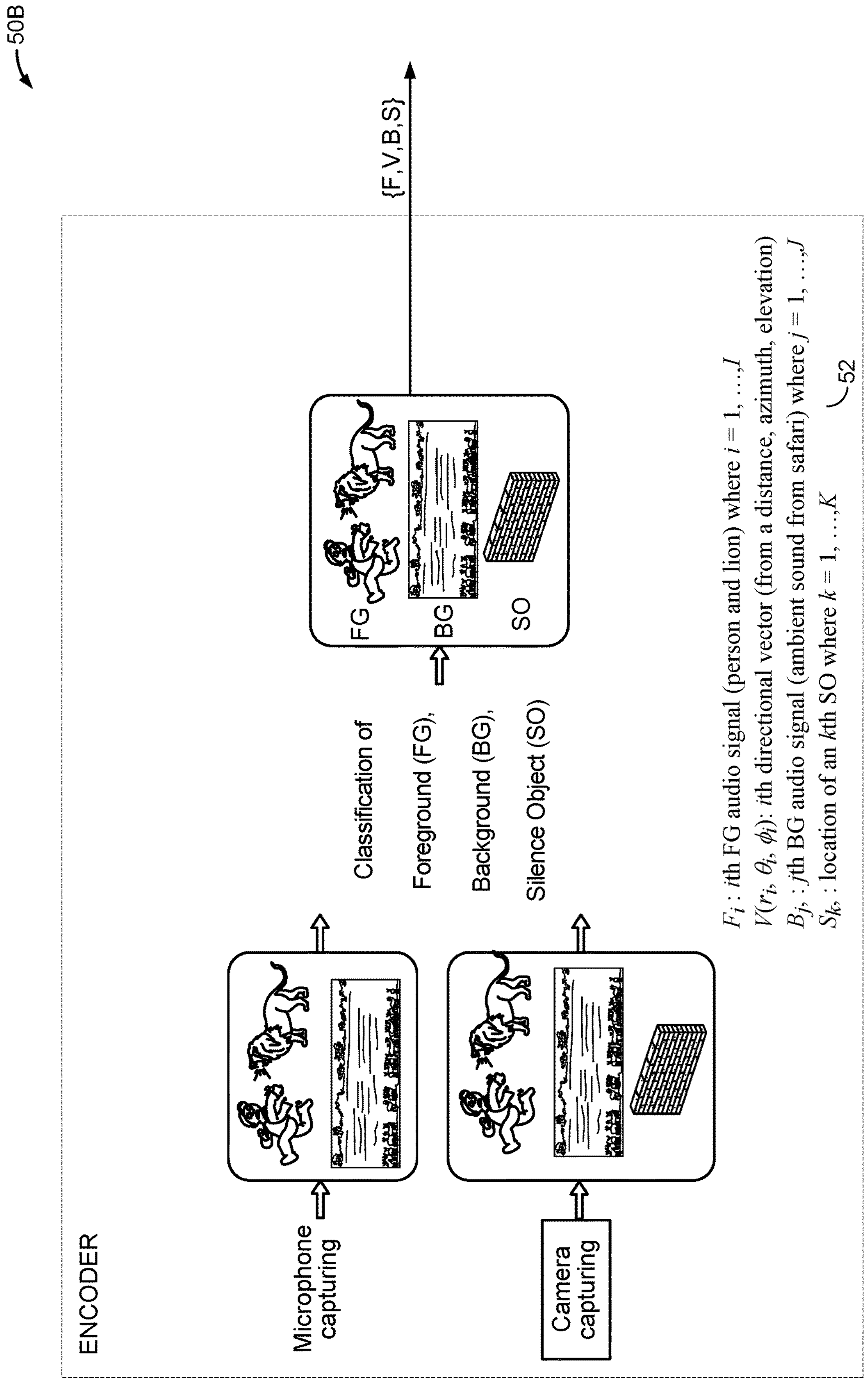

FIG. 6B is a flowchart illustrating an encoding process 50B that the audio encoding device 20 may perform. As in the case of process 50A of FIG. 6A, process 50B represents a process in which the audio encoding device 20 encodes the bitstream 21 and the metadata 23 using live capture data from the microphones 5 and one or more cameras. In contrast to process 50A of FIG. 6A, process 50B represents a process in which the audio encoding device 20 does not perform compression operations before transmitting the bitstream 21 and the metadata 23. Alternatively, process 50B may also represent an example in which the audio encoding device does not perform transmission, but instead, communicates the bitstream 21 and the metadata 23 to decoding components within an integrated VR device that also includes the audio encoding device 20.

Figure 6C:
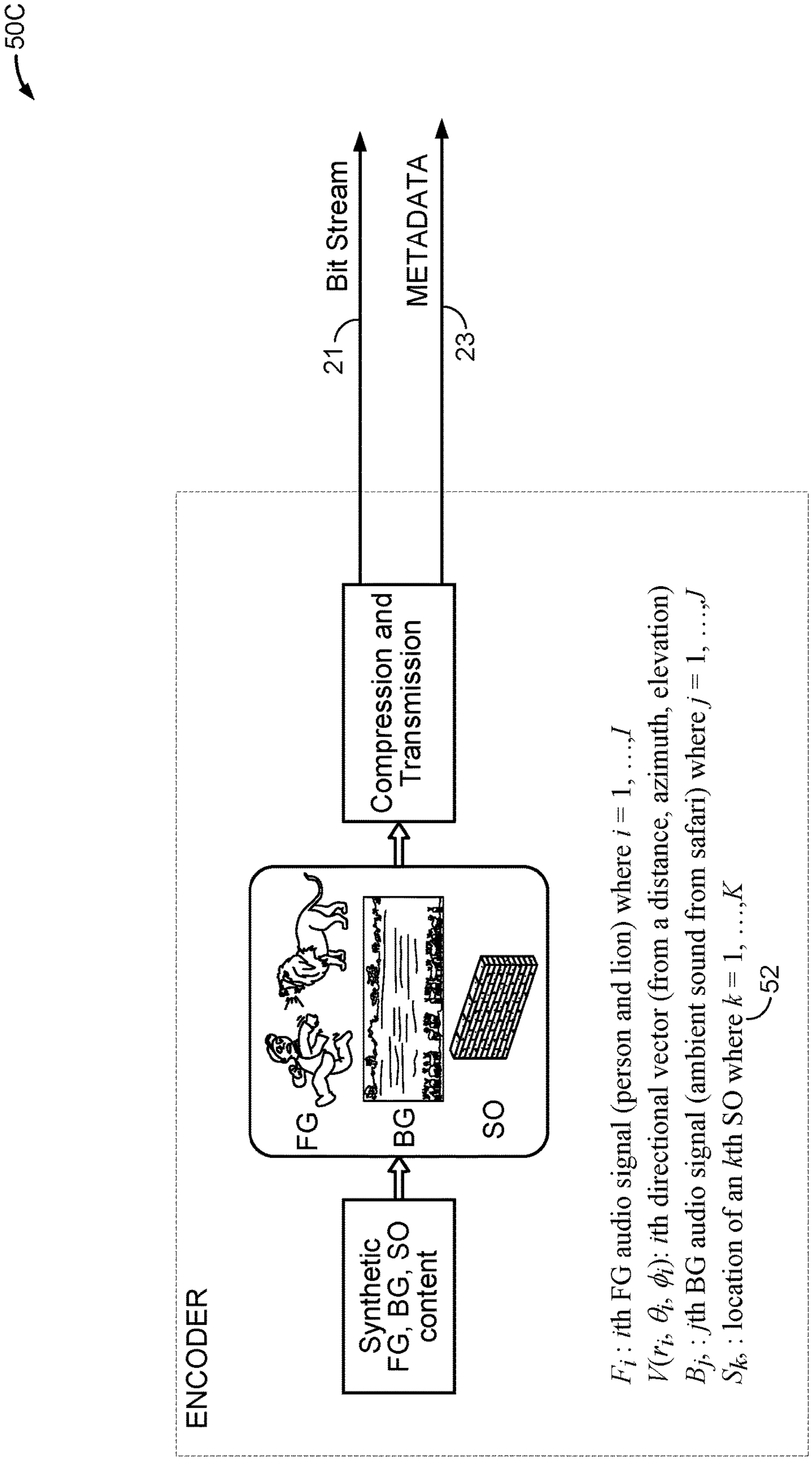

FIG. 6C is a flowchart illustrating an encoding process 50C that the audio encoding device 20 may perform. In contrast to of processes 50A & 50B of FIGS. 6A & 6B, process 50*c* represents a process in which the audio encoding device 20 uses synthetic audio and video data, instead of live-capture data.

Figure 6D:
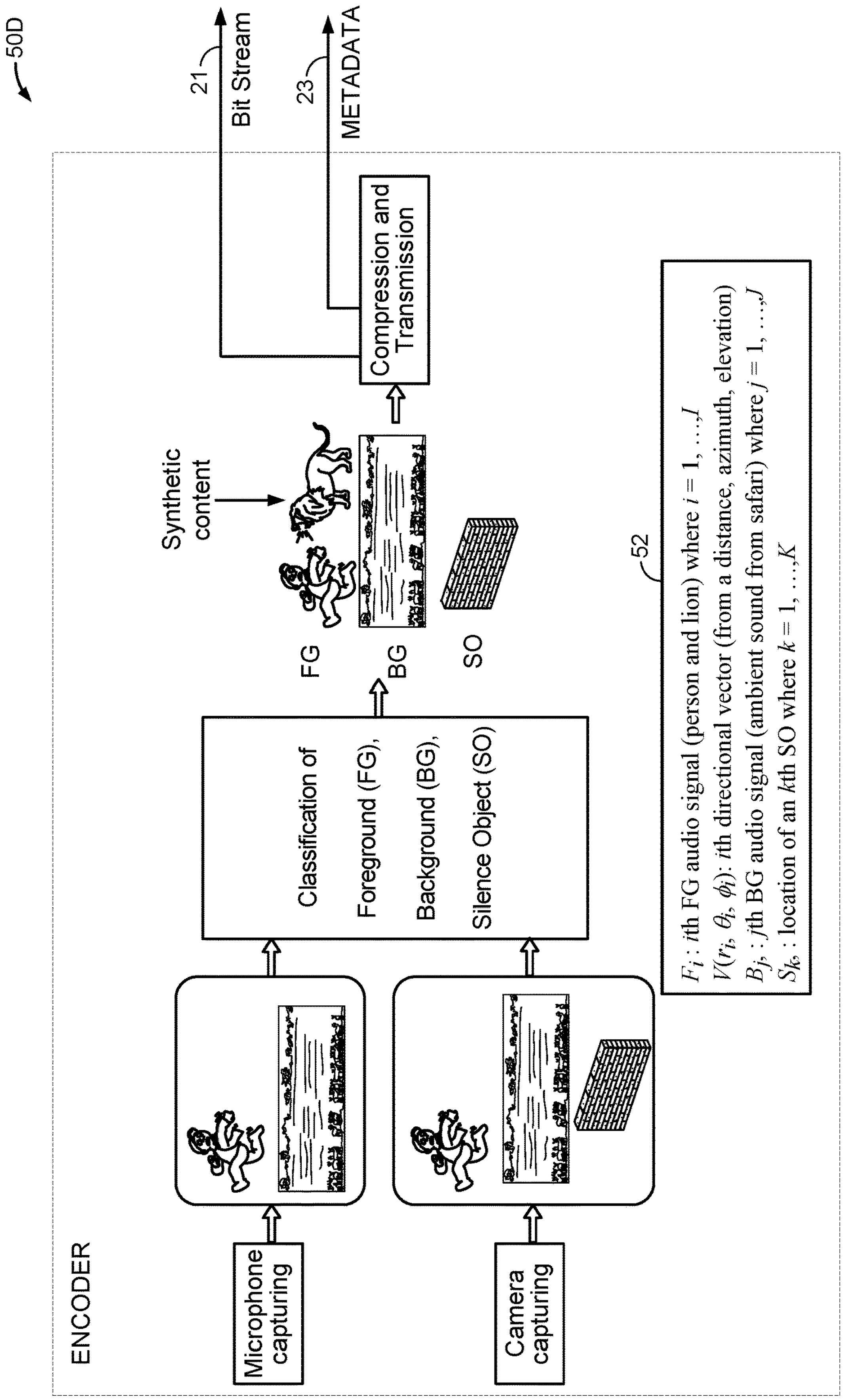

FIG. 6D is a flowchart illustrating an encoding process 50C that the audio encoding device 20 may perform. Process 50D represents a process in which the audio encoding device 20 uses a combination of live-captured and synthetic audio and video data.

Figure 7:
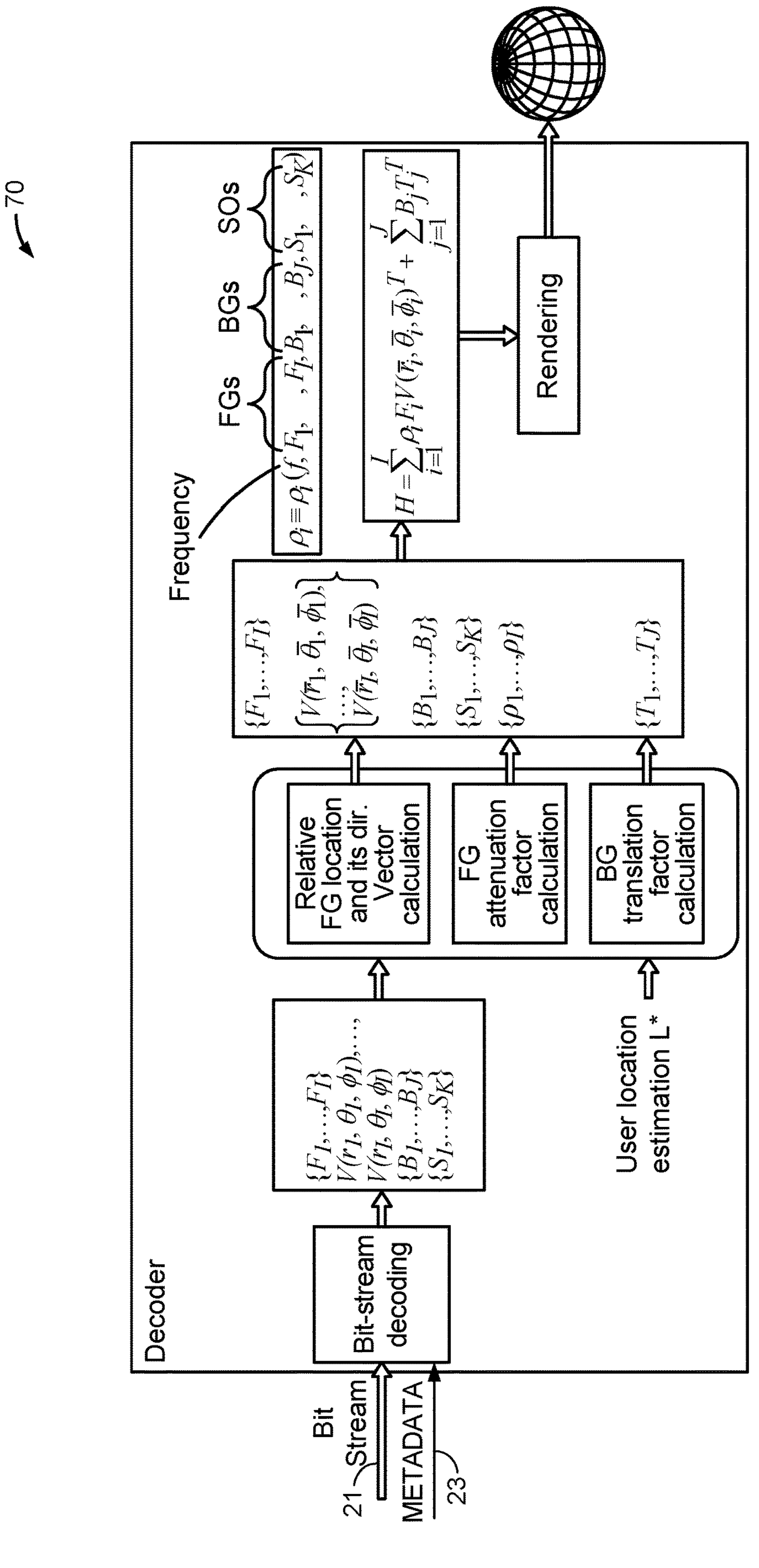
FIG. 7 is a flowchart illustrating a decoding process that an audio decoding device may perform, in accordance with aspects of this disclosure.

FIG. 7 is a flowchart illustrating a decoding process 70 that the audio decoding device 24 may perform, in accordance with aspects of this disclosure. The audio decoding device 24 may receive the bitstream 21 and the metadata 23 from the audio encoding device 20. In various examples, the audio decoding device 24 may receive the bitstream 21 and the metadata 23 via transmission, or via internal communication if the audio encoding device 20 is included within an integrated VR device that also includes the audio decoding device 24. The audio decoding device 24 may decode the bitstream 21 and the metadata 23 to reconstruct the following data, which are described above with respect to the legend 52 of FIGS. 6A-6D:

$\{F_1,\Lambda,F_1\}$ $\{V(r_1,\theta_1,\phi_1),\Lambda,V(r_1,\theta_1,\phi_1)\}$ $\{B_1,\Lambda,B_J\}$ $\{S_1,\Lambda,S_K\}$ In turn, the audio decoding device 24 may combine data indicating the user location estimation with the FG object location and directional vector calculations, the FG object attenuation (via application of the transmission factors), and the BG object translation calculations. In FIG. 7, the formula $\rho_i \equiv \rho_i(f,F_1,\Lambda,F_I,B_1,\Lambda,B_J,S_1,\Lambda,S_K)$ represents the attenuation of an $i^{th}$ FG object, using the transmission factors received in the metadata 23. In turn, the audio decoding device 24 may render an audio scene of the 3D soundfield by solving the following equation:

$$H = \sum_{i=1}^{I} \rho_i F_i V(\bar{r}_i, \bar{\theta}_i, \bar{\phi}_i)^T + \sum_{j=1}^{J} B_j T_j^T$$

As shown, the audio decoding device 24 may calculate one summation with respect to FG objects, and a second summation with respect to BG objects. With respect to the FG object summation, the audio decoding device 24 may apply the transmission factor ρ for an $i^{th}$ object to a product of the FG audio signal for the $i^{th}$ object and the directional vector calculation for the $i^{th}$ object. In turn, the audio decoding device 24 may perform a summation of the resulting product values for a series of values of i.

With respect to the BG objects, the audio decoding device 24 may calculate a product of the $j^{th}$ BG audio signal and the corresponding translation factor for the $j^{th}$ BG audio signal. In turn, the audio decoding device 24 may add the FG object-related summation value and the BG object-related summation value to calculate H, for rendering of the 3D soundfield.

Figure 8:
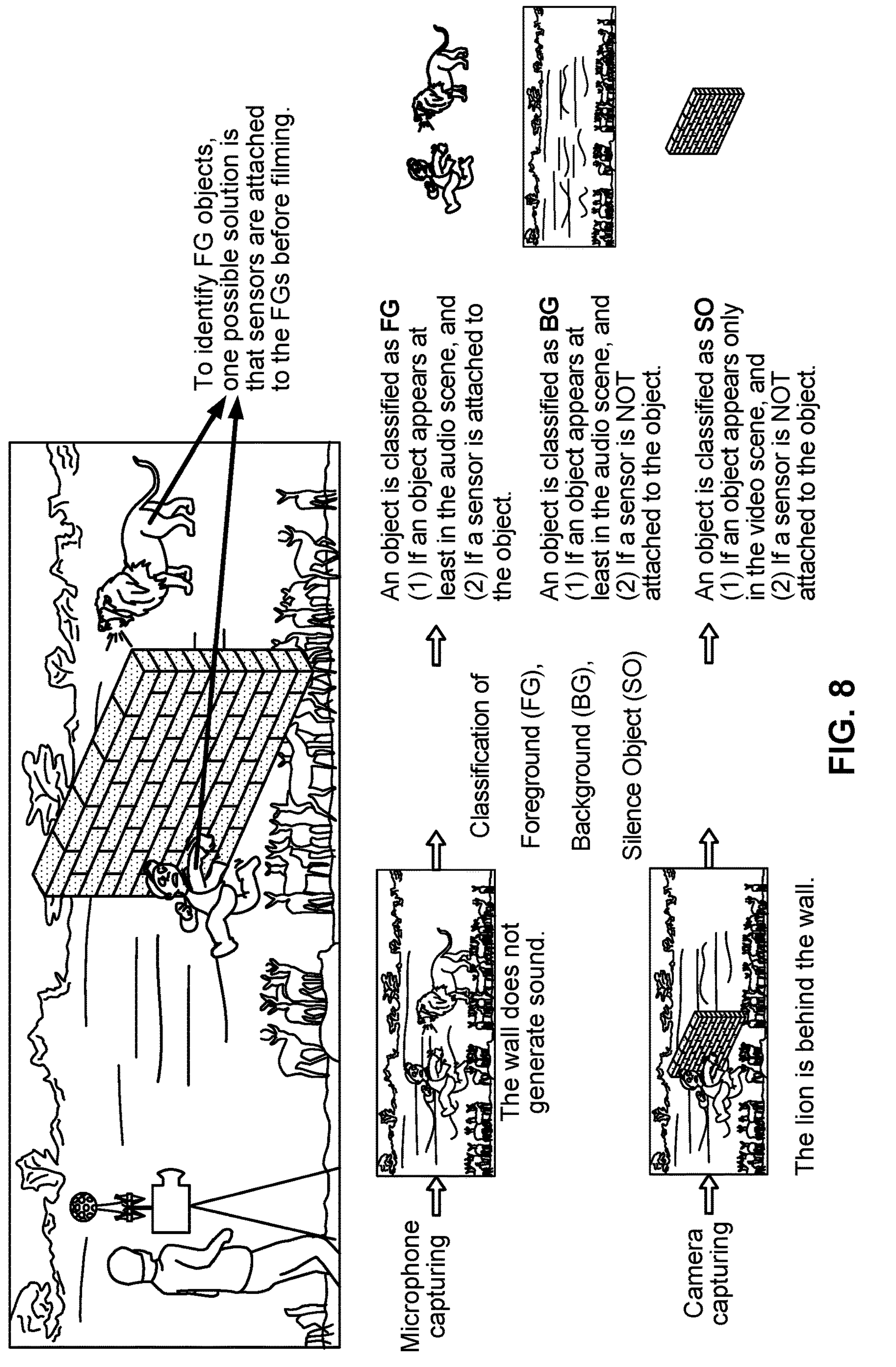
FIG. 8 is a diagram illustrating an object classification mechanism that an audio encoding device may implement to categorize silent objects, foreground objects, and background objects, in accordance with aspects of this disclosure.

FIG. 8 is a diagram illustrating an object classification mechanism that the audio encoding device 20 may implement to categorize SOs, FG objects, and BG objects, in accordance with aspects of this disclosure. The particular example of FIG. 8 is directed to an example in which the video data and the audio data are captured live, using the microphones 5 and various cameras. The audio encoding device 20 may classify an object as a SO if the object satisfies two conditions, namely, (i) the object appears only a video scene (i.e., is not represented in the corresponding audio scene), and (ii) no sensor is attached to the object. In the example illustrated in FIG. 8, the wall is a SO. In the example of FIG. 8, the audio encoding device 20 may classify an object as a FG object if the object satisfies two conditions, namely, (i) the object appears in an audio scene, and (ii) a sensor is attached to the object. In the example of FIG. 8, the audio encoding device 20 may classify an object as a FG object if the object satisfies two conditions, namely, (i) the object appears in an audio scene, and (ii) no sensor is attached to the object.

Again, the specific example of FIG. 8 is directed to scenarios in which SOs, FG objects, and BG objects are identified using information on whether a sensor is attached to the object. That is, FIG. 8 may be an example of object classification techniques that the audio encoding device 20 may use in cases of live capture of video data and audio data for a VR/MR/AR experience. In other examples, such as if the video and/or audio data are synthetic, as in some aspects of VR/MR/AR experiences, the audio encoding device 20 may classify the SOs, FG objects, and the BG objects based on whether or not the audio objects map to a pre-identified audio object in a list.

Figure 9A:
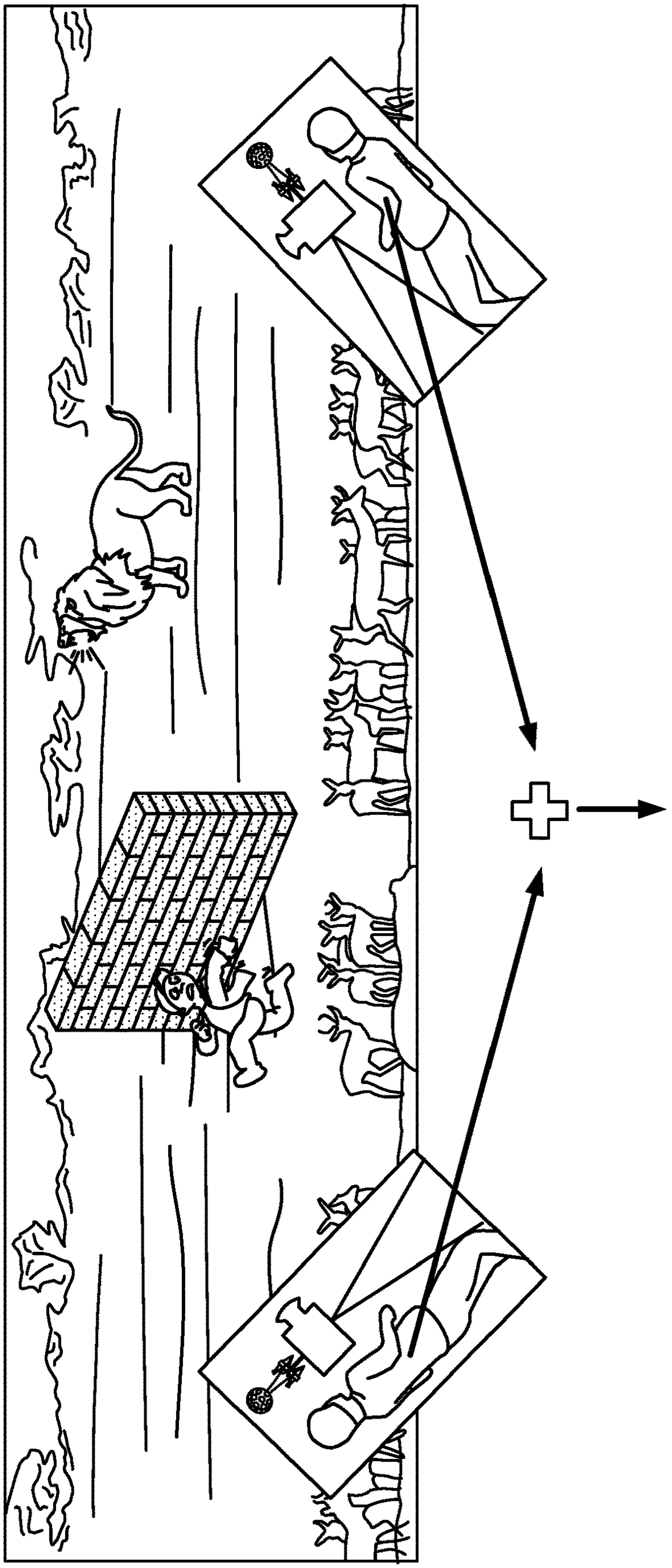
FIG. 9A is a diagram illustrating an example of stitching of audio/video capture data from multiple microphones and cameras, in accordance with aspects of this disclosure.

FIG. 9A is a diagram illustrating an example of stitching of audio/video capture data from multiple microphones and cameras, in accordance with aspects of this disclosure.

Figure 9B:
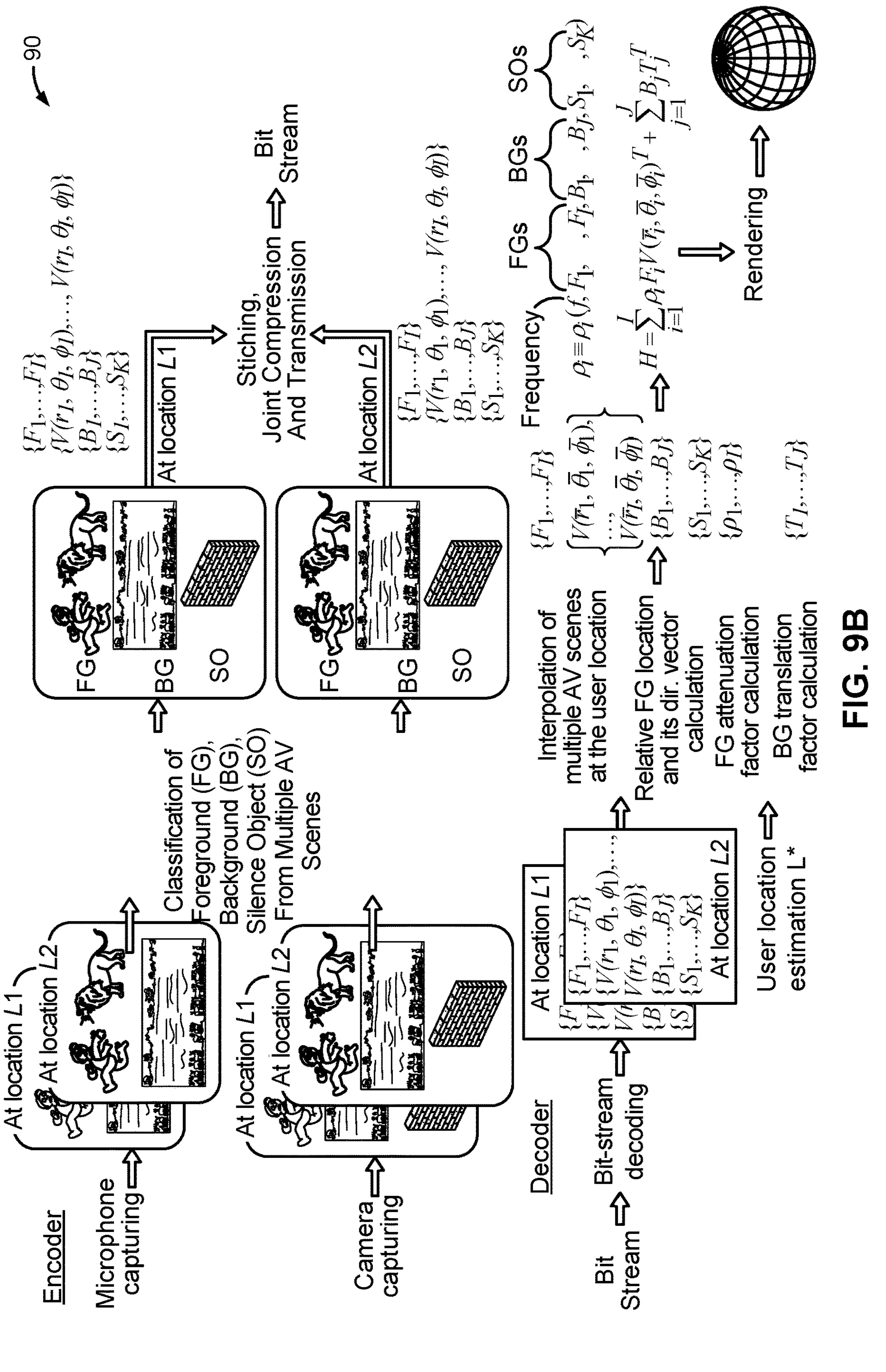
FIG. 9B is a flowchart illustrating a process that includes encoder- and decoder-side operations of parallax adjustments with stitching and interpolation, in accordance with aspects of this disclosure.

FIG. 9B is a flowchart illustrating a process 90 that includes encoder- and decoder-side operations of parallax adjustments with stitching and interpolation, in accordance with aspects of this disclosure. The process 90 may generally correspond to a combination of the process 50A of FIG. 6A with respect to the operations of the audio encoding device 20 and the process 70 of FIG. 7 with respect to the operations of the audio decoding device 24. However, as shown in FIG. 9B, the process 90 includes data from multiple locations, such as locations L1 and L2. Moreover, the audio encoding device 20 performs stitching along with joint compression and transmission, and the audio decoding device 24 performs interpolation of multiple audio/video scenes at the listener or user location. For instance, to perform the interpolation, the audio decoding device 24 may use point clouds. In various examples, the audio decoding device 24 may use the point clouds to interpolate the listener location between multiple candidate listener locations. For instance, the audio decoding device 24 may receive various listener location candidates in the bitstream 21.

Figure 9C:
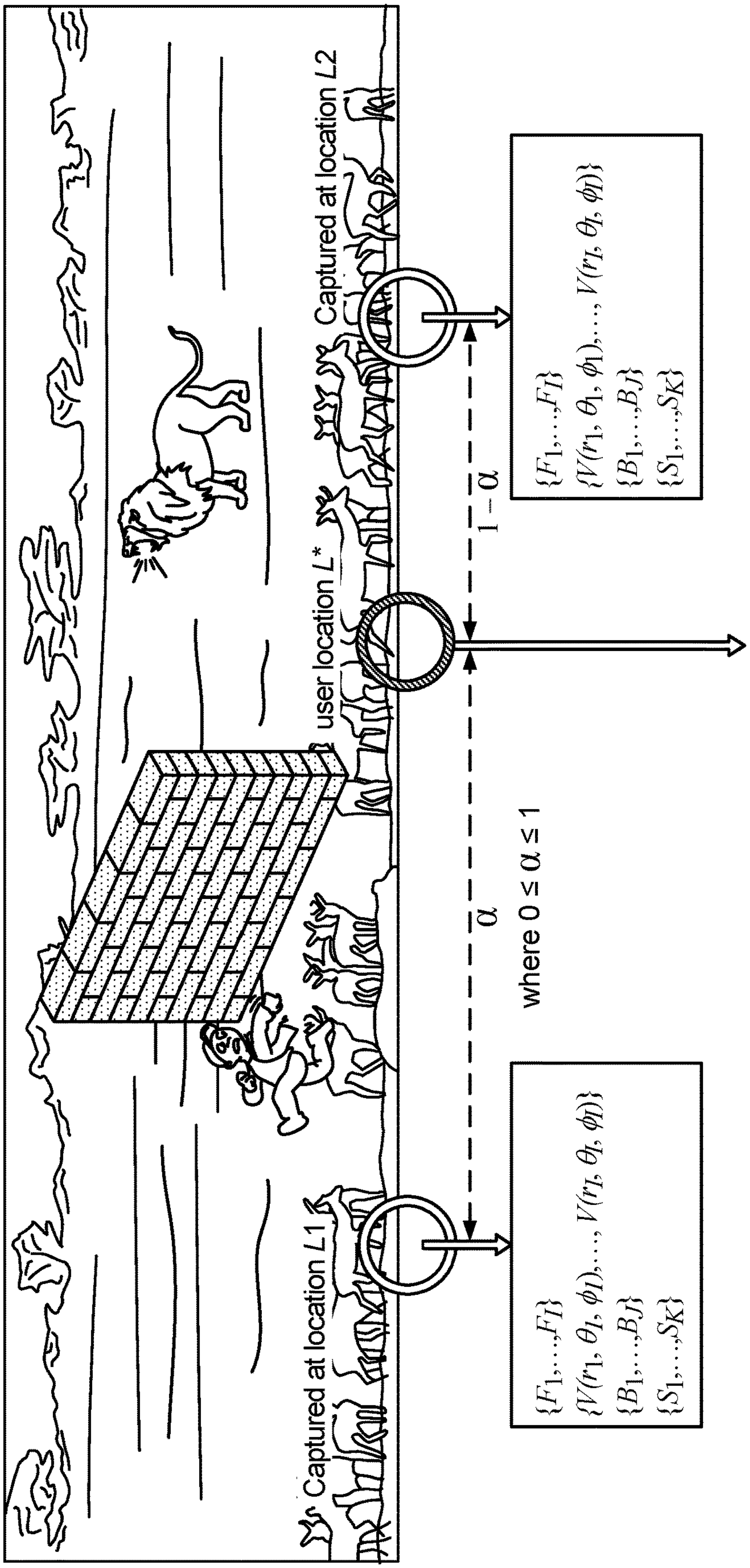
FIG. 9C is a diagram illustrating the capture of foreground objects and background objects at multiple locations.

FIG. 9C is a diagram illustrating the capture of FG objects and BG objects at multiple locations.

Figure 9D:
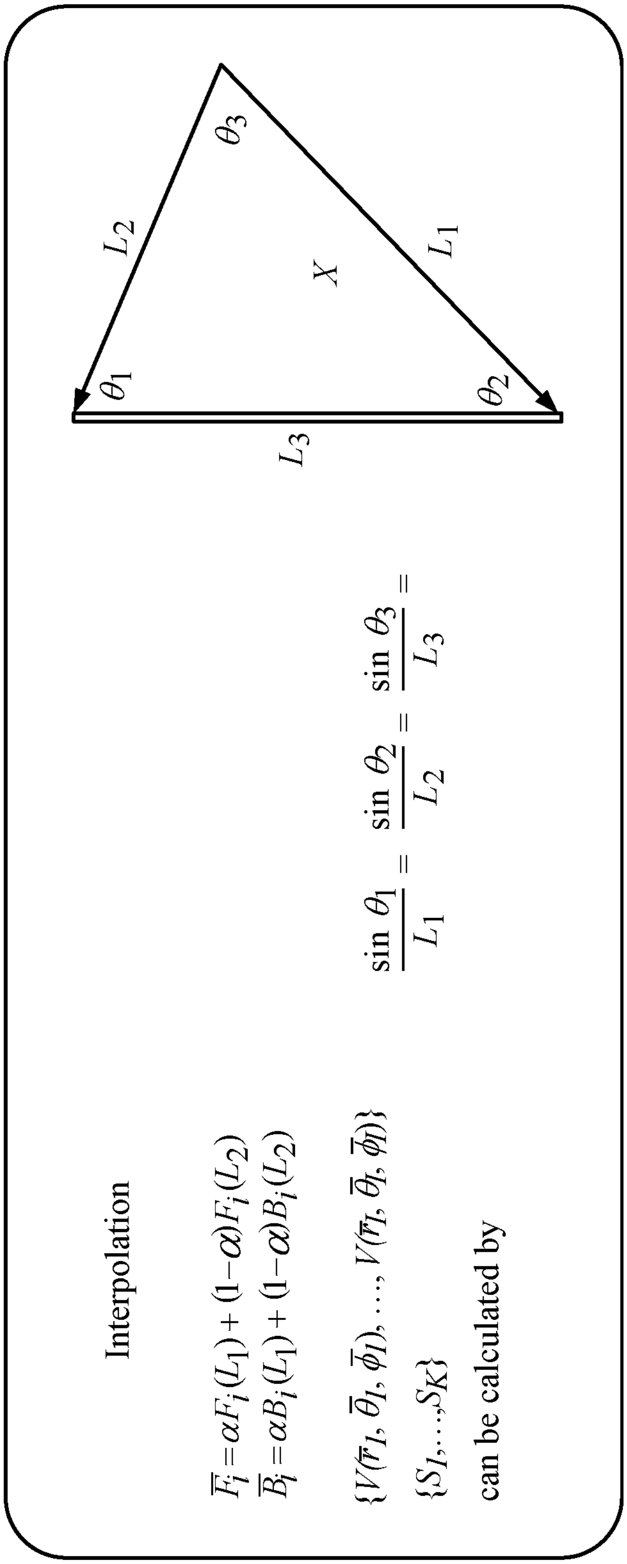
FIG. 9D illustrates a mathematical expression of an interpolation technique that an audio decoding device may perform, in accordance with aspects of this disclosure.

FIG. 9D illustrates a mathematical expression of an interpolation technique that the audio decoding device 24 may perform, in accordance with aspects of this disclosure. The audio decoding device 24 may perform the interpolation operations of FIG. 9D as a reciprocal operation to stitching operations performed by the audio encoding device 20. For instance, to perform stitching operations of this disclosure, the audio encoding device 20 may rearrange FG objects of the 3D soundfield in such a way that a foreground signal $F_i$ at a location $L_1$ and a foreground signal $F_j$ at a location $L_2$ both originate from the same FG object, if i=j. The audio encoding device 20 may implement one or more sound identification and/or image identification algorithms to check or verify the identity of each FG object. Moreover, the audio encoding device 20 may perform the stitching operations not only with respect to the FG objects, but with respect to other parameters, as well.

As shown in FIG. 9D, the audio decoding device may perform the interpolation operations of this disclosure according to the following equations:

$$\overline{F}_i=\alpha F_i(L_1)+(1-\alpha)F_i(L_2)$$

$$\overline{B}_i=\alpha B_i(L_1)+(1-\alpha)B_i(L_2)$$

That is, the equations presented above are applicable to FG and BG object-based calculations, such as the foreground and background signals applicable for a particular location i. In terms of the directional vectors and the silent objects at various locations, the audio decoding device 24 may perform the interpolation operations of this disclosure according to the following equations:

$$\{V(\overline{r}_1,\overline{\theta}_1,\overline{\phi}_1),\Lambda,V(\overline{r}_I,\overline{\theta}_I,\overline{\phi}_I)\}$$

$$\{S_1,\Lambda,S_K\}$$

Aspects of the silent object interpolation may be calculated by the following operations, as illustrated in FIG. 9D:

$$[(\sin\theta_1)/L_1]=[(\sin\theta_2)/L_2]=[(\sin\theta_3)/L_3]$$

Figure 9E:
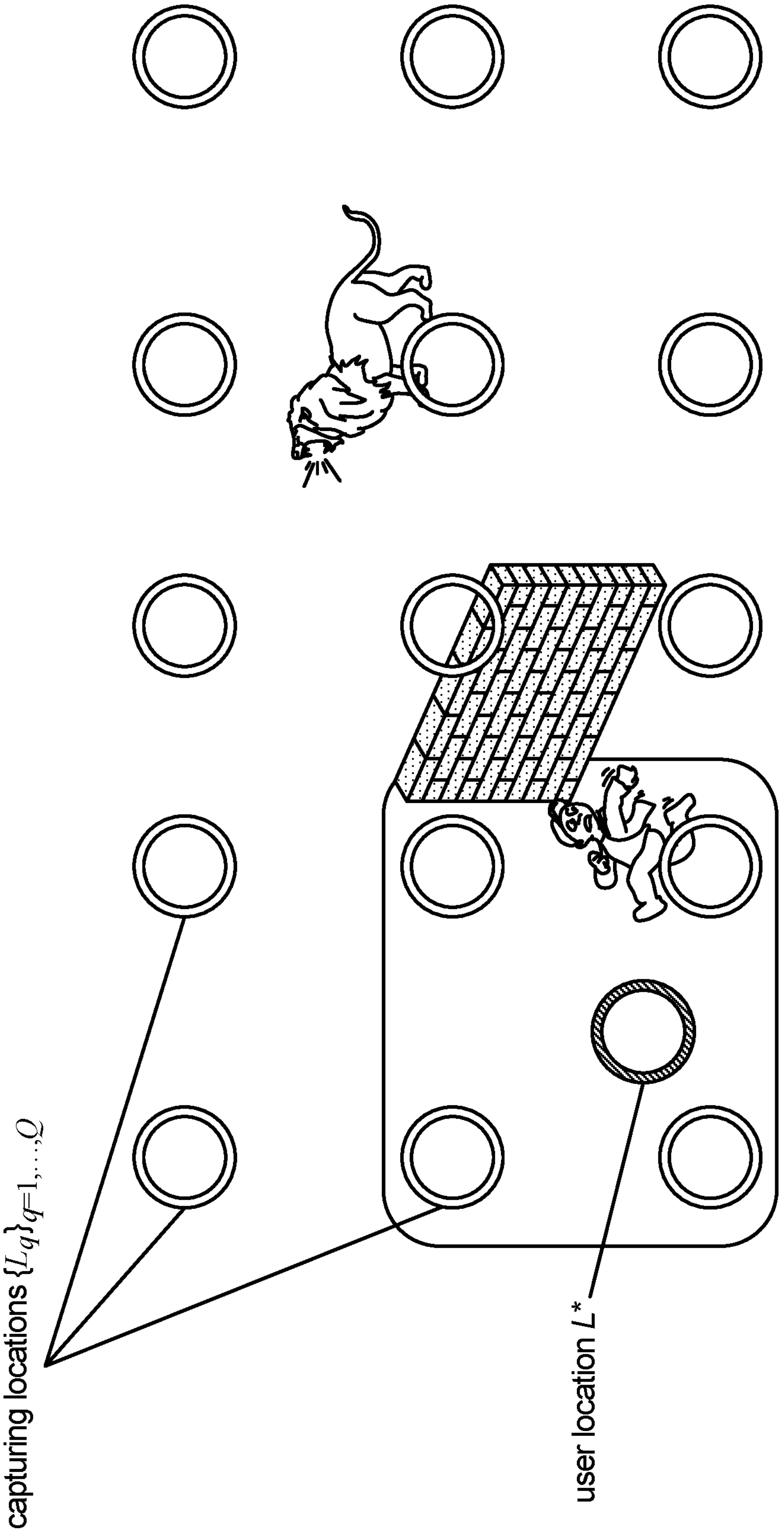
FIG. 9E is a diagram illustrating an application of point cloud-based interpolation that an audio decoding device may implement, in accordance with aspects of this disclosure.

FIG. 9E is a diagram illustrating an application of point cloud-based interpolation that the audio decoding device 24 may implement, in accordance with aspects of this disclosure. The audio decoding device 24 may use the point clouds (denoted by rings in FIG. 9E) to obtain a sampling (e.g. a dense sampling) of 3D space with audio and video signals. For instance, the received bitstream 21 may represent audio and video data captured from multiple locations $\{L_q\}_{q=1,\Lambda,Q}$ where the audio encoding device 20 has stitched and performed joint compression and interpolation with adjacent data from the user location L*. in the example illustrated in FIG. 9E, the audio decoding device 24 may use data of four capture locations (positioned within the rectangle with rounded corners), to generate or reconstruct the virtually captured data at the user location L*.

Figure 10:
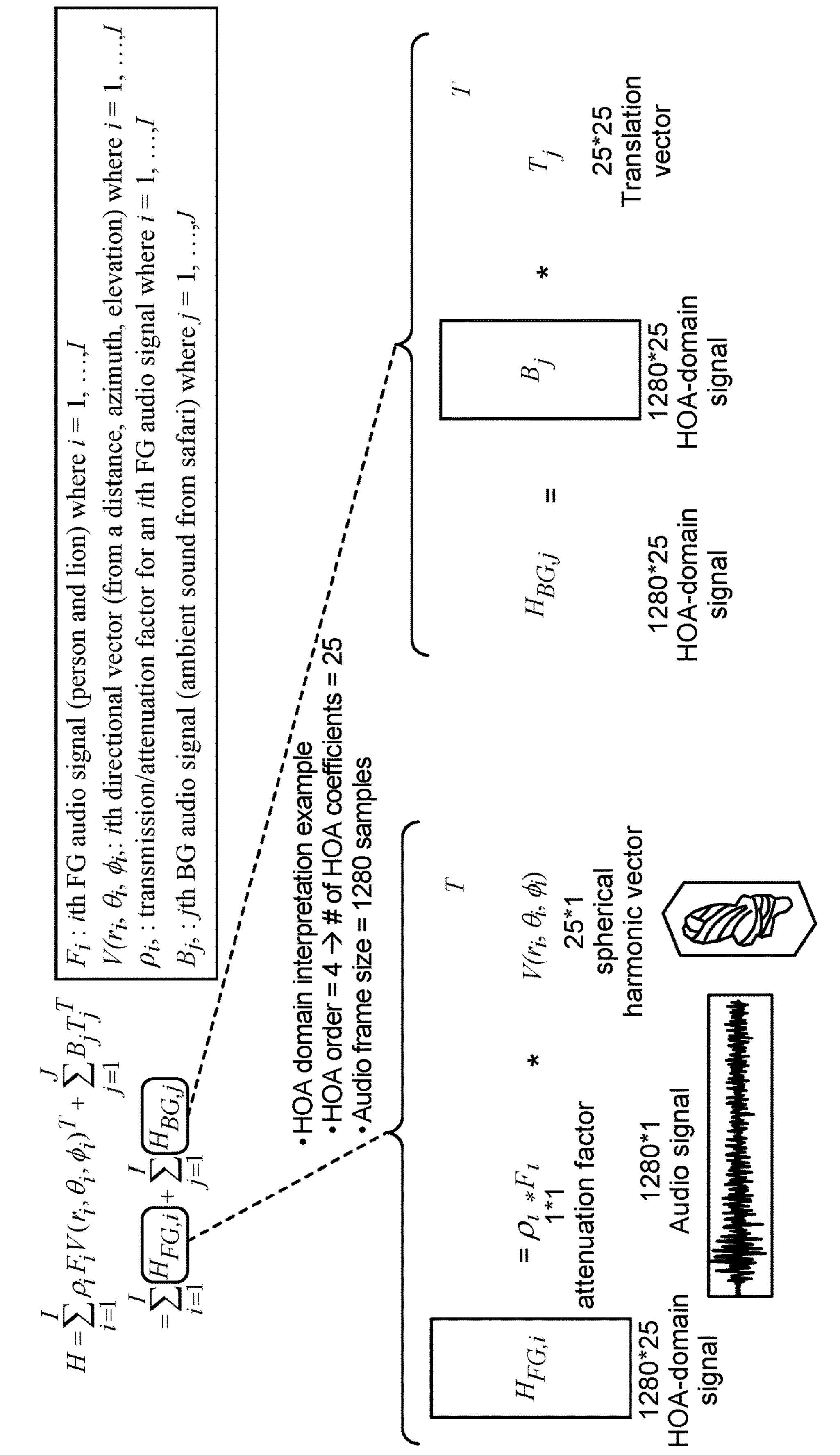
FIG. 10 is a diagram illustrating aspects of an HOA domain calculation of attenuation of foreground audio objects that an audio decoding device may perform, in accordance with aspects of this disclosure.

FIG. 10 is a diagram illustrating aspects of an HOA domain calculation of attenuation of foreground audio objects that the audio decoding device 24 may perform, in accordance with aspects of this disclosure. In the example of FIG. 10, the audio decoding device 24 may use an HOA order of four (4), thereby using a total of twenty-five (25) HOA coefficients. As illustrated in FIG. 10, the audio decoding device 24 may use an audio frame size of 1,280 samples.

FIG. 11 is a diagram illustrating aspects of transmission factor calculations that the audio encoding device 20 may perform, in accordance with one or more techniques of this disclosure.

Figure 12:
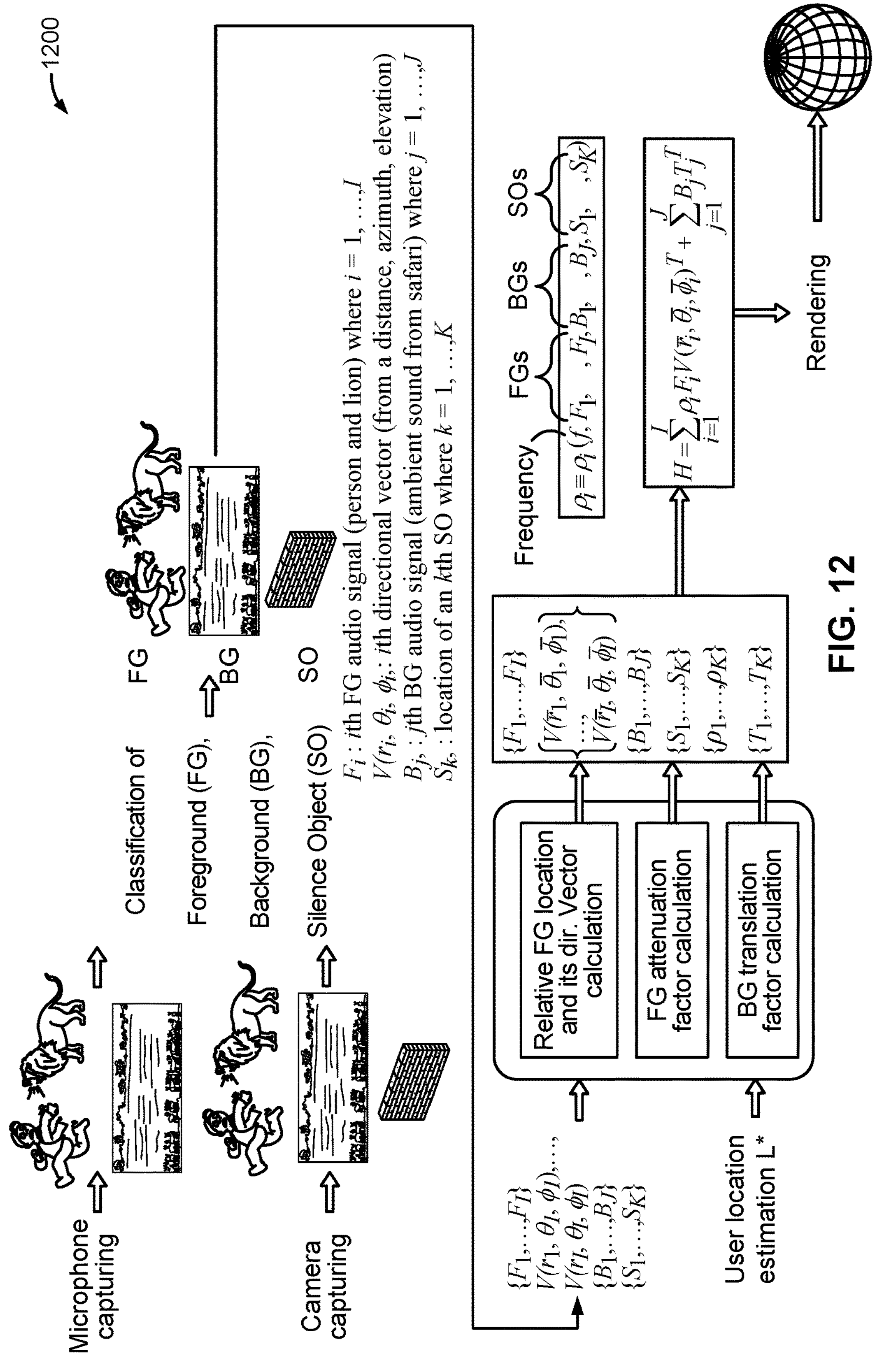
FIG. 12 is a diagram illustrating a process that may be performed by an integrated encoding/rendering device, in accordance with aspects of this disclosure.

FIG. 12 is a diagram illustrating a process 1200 that may be performed by an integrated encoding/rendering device, in accordance with aspects of this disclosure. As such, according to the process 1200, the integrated device may include both of the audio encoding device 20 and the audio decoding device 24, and optionally, other components and/or devices discussed herein. As such, the process 1200 of FIG. 12 does not include compression or transmission steps, because the audio encoding device 20 may communicate the bitstream 21 and the metadata 23 to the audio decoding device 24 using internal communication channels within the integrated device, such as communication bus architecture of the integrated device.

Figure 13:
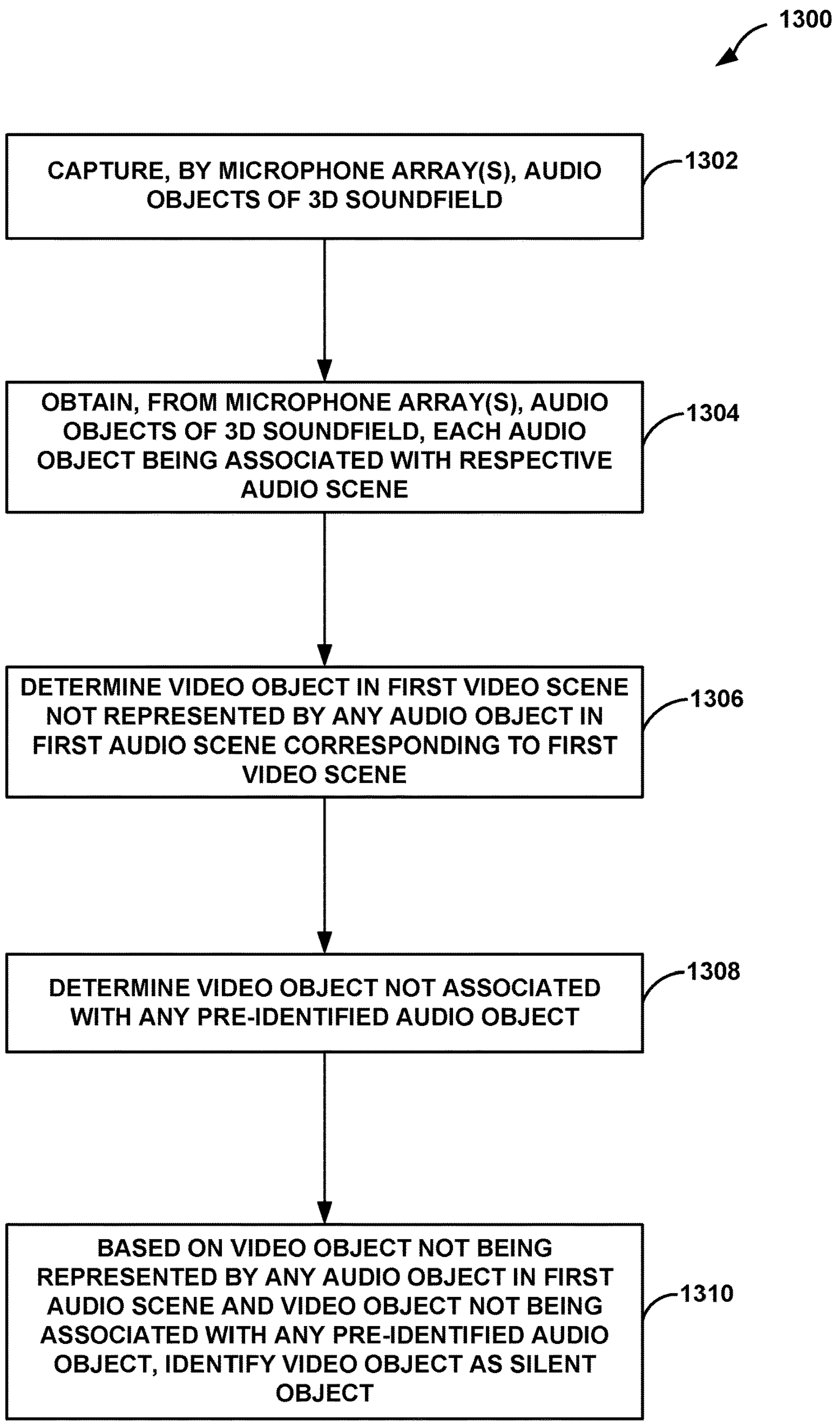
FIG. 13 is a flowchart illustrating a process that an audio encoding device or an integrated encoding/rendering device may perform, in accordance with aspects of this disclosure.

FIG. 13 is a flowchart illustrating a process 1300 that an audio encoding device or an integrated encoding/rendering device may perform, in accordance with aspects of this disclosure. Process 1300 may begin when one or more microphone arrays capture audio objects of a 3D soundfield (1302). In turn, processing circuitry of the audio encoding device may obtain, from the microphone array(s), the audio objects of the 3D soundfield, where each audio object is associated with a respective audio scene of the audio data captured by the microphone array(s) (1304). The processing circuitry of the audio encoding device may determine that a video object included in a first video scene is not represented by any corresponding audio object in a first audio scene that corresponds to the first video scene (1306).

The processing circuitry of the audio encoding device may determine that the video object is not associated with any pre-identified audio object (1308). In turn, responsive to the determinations that the video object is not represented by any corresponding audio object in the first audio scene and that the video object is not associated with any pre-identified audio object, the processing circuitry of the audio encoding device may identify the video object as a silent object (1310).

As such, in some examples of this disclosure, an audio encoding device of this disclosure includes a memory device configured to store audio objects obtained from one or more microphone arrays with respect to a three-dimensional (3D) soundfield, wherein each obtained audio object is associated with a respective audio scene, and to store video data obtained from one or more video capture devices, the video data comprising one or more video scenes, each respective video scene being associated with a respective audio scene of the obtained audio data. The device further includes processing circuitry coupled to the memory device, the processing circuitry being configured to determine that a video object included in a first video scene is not represented by any corresponding audio object in a first audio scene that corresponds to the first video scene, to determine that the video object is not associated with any pre-identified audio object, and to identify, responsive to the determinations that the video object is not represented by any corresponding audio object in the first audio scene and that the video object is not associated with any pre-identified audio object, the video object as a silent object.

In some examples, the processing circuitry is further configured to determine that a first audio object included in obtained audio data is associated with a pre-identified audio object, and to identify, responsive to the determination that the audio object is associated with the pre-identified audio object, the first audio object as a foreground audio object. In some examples, the processing circuitry is further configured to determine that a second audio object included in obtained audio data is not associated with any pre-identified audio object, and to identify, responsive to the determination that the second audio object is not associated with any pre-identified audio object, the second audio object as a background audio object.

In some examples, the processing circuitry being is configured to determine that the first audio object is associated with a pre-identified audio object by determining that the first audio object is associated with an audio source that is equipped with one or more sensors. In some examples, the audio encoding device further includes the one or more microphone arrays coupled to the processing circuitry, the one or more microphone arrays being configured to capture the audio objects associated with the 3D soundfield. In some examples, the audio encoding device further includes the one or more video capture devices coupled to the processing circuitry, the one or more video capture devices being configured to capture the video data. The video capture devices may include, be, or be part of, the cameras illustrated in the drawings and described above with respect to the drawings. For example, the video capture devices may represent multiple (e.g., dual) cameras positioned such that the cameras capture video data or images of a scene from different perspectives. In some examples, the foreground audio object is included in the first audio scene that corresponds to the first video scene, and the processing circuitry being further configured to determine whether positional information of the silent object with respect to the first video scene causes attenuation of the foreground audio object.

In some examples, the processing circuitry is further configured to generate, responsive to determining that the silent object causes the attenuation of the foreground audio object, one or more transmission factors with respect to the foreground audio object, wherein the generated transmission factors represent adjustments with respect to the foreground audio object. In some examples, the generated transmission factors represent adjustments with respect to an energy of the foreground audio object. In some examples, the generated transmission factors represent adjustments with respect to directional characteristics of the foreground audio object. In some examples, the processing circuitry is further configured to transmit the transmission factors out of band with respect to a bitstream that includes the foreground audio object. In some examples, the generated transmission factors represent metadata with respect to the bitstream.

Figure 14:
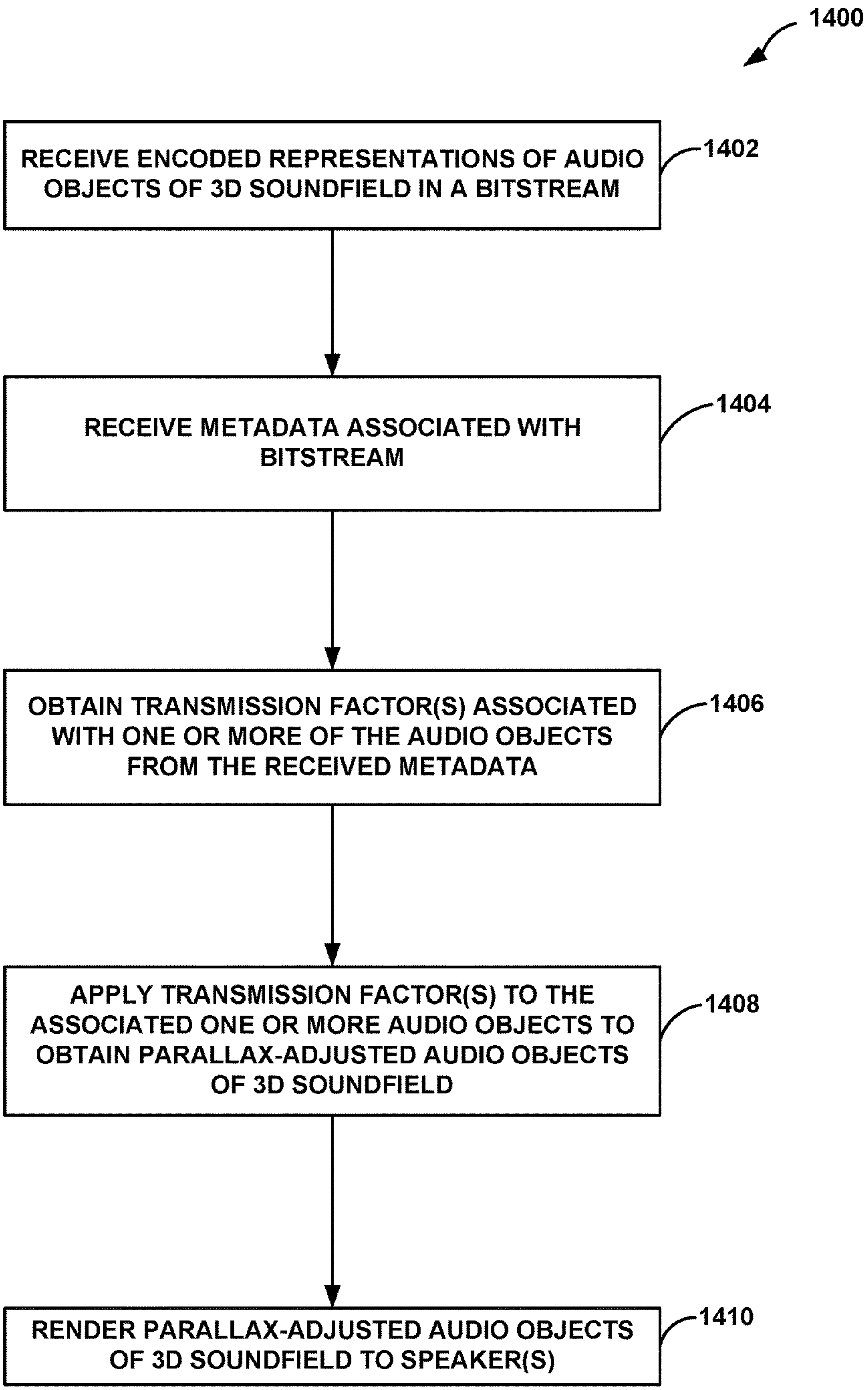
FIG. 14 is a flowchart illustrating an example process that an audio decoding device or an integrated encoding/decoding/rendering device may perform, in accordance with aspects of this disclosure.

FIG. 14 is a flowchart illustrating an example process 1400 that an audio decoding device or an integrated encoding/decoding/rendering device may perform, in accordance with aspects of this disclosure. Process 1400 may begin when processing circuitry of the audio decoding device receives, in a bitstream, encoded representations of audio objects of a 3D soundfield (1402). Additionally, the processing circuitry of the audio decoding device may receive metadata associated with the bitstream (1404). It will be appreciated that the sequence illustrated in FIG. 14 is a non-limiting example, and that the processing circuitry of the audio decoding device may receive the bitstream and the metadata in any order, or in parallel, or partly in parallel.

The processing circuitry of the audio decoding device may obtain, from the received metadata, one or more transmission factors associated with one or more of the audio objects (1406). In addition, the processing circuitry of the audio decoding device may apply the transmission factors to the one or more audio objects to obtain parallax-adjusted audio objects of the 3D soundfield (1408). The audio decoding device may further comprise a memory coupled to the processing circuitry. The memory device may store at least a portion of the received bitstream, the received metadata, or the parallax-adjusted audio objects of the 3D soundfield. The processing circuitry of the audio decoding device may render the parallax-adjusted audio objects of the 3D soundfield to one or more speakers (1410). For instance, the processing circuitry of the audio decoding device may render the parallax-adjusted audio objects of the 3D soundfield into one or more speaker feeds that drive the one or more speakers.

In some examples of this disclosure, an audio decoding device includes processing circuitry configured to receive, in a bitstream, encoded representations of audio objects of a three-dimensional (3D) soundfield, to receive metadata associated with the bitstream, to obtain, from the received metadata, one or more transmission factors associated with one or more of the audio objects, and to apply the transmission factors to the one or more audio objects to obtain parallax-adjusted audio objects of the 3D soundfield. The device further includes a memory device coupled to the processing circuitry, the memory device being configured to store at least a portion of the received bitstream, the received metadata, or the parallax-adjusted audio objects of the 3D soundfield. In some examples, the processing circuitry is further configured to determine listener location information, and to apply the listener location information in addition to applying the transmission factors to the one or more audio objects. In some examples, the processing circuitry is further configured to apply relative foreground location information between the listener location information and respective locations associated with foreground audio objects of the one or more audio objects. In some examples, the processing circuitry is further configured to apply background translation factors that are calculated using respective locations associated with background audio objects of the one or more audio objects.

In some examples, the processing circuitry is further configured to apply foreground attenuation factors to respective foreground audio objects of the one or more audio objects. In some examples, the processing circuitry is further configured to determine a minimum transmission value for the respective foreground audio objects, to determine whether applying the transmission factors to the respective foreground audio objects produces an adjusted transmission value that is lower than the minimum transmission value, and to render, responsive to determining that the adjusted transmission value that is lower than the minimum transmission value, the respective foreground audio objects using the minimum transmission value. In some examples, the processing circuitry is further configured to adjust an energy of the respective foreground audio objects. In some examples, the processing circuitry being further configured to attenuate respective energies of the respective foreground audio objects. In some examples, the processing circuitry is further configured to adjust directional characteristics of the respective foreground audio objects. In some examples, the processing circuitry is further configured to adjust parallax information of the respective foreground audio objects. In some examples, the processing circuitry is further configured to adjust the parallax information to account for one or more silent objects represented in a video stream associated with the 3D soundfield. In some examples, the processing circuitry is further configured to receive the metadata within the bitstream.

In some examples, the processing circuitry is further configured to receive the metadata out of band with respect to the bitstream. In some examples, the processing circuitry is further configured to output video data associated with the 3d soundfield to one or more displays. In some examples, the device further includes the one or more displays, the one or more displays being configured to receive the video data from the processing circuitry, and to output the received video data in visual form.

Figure 15:
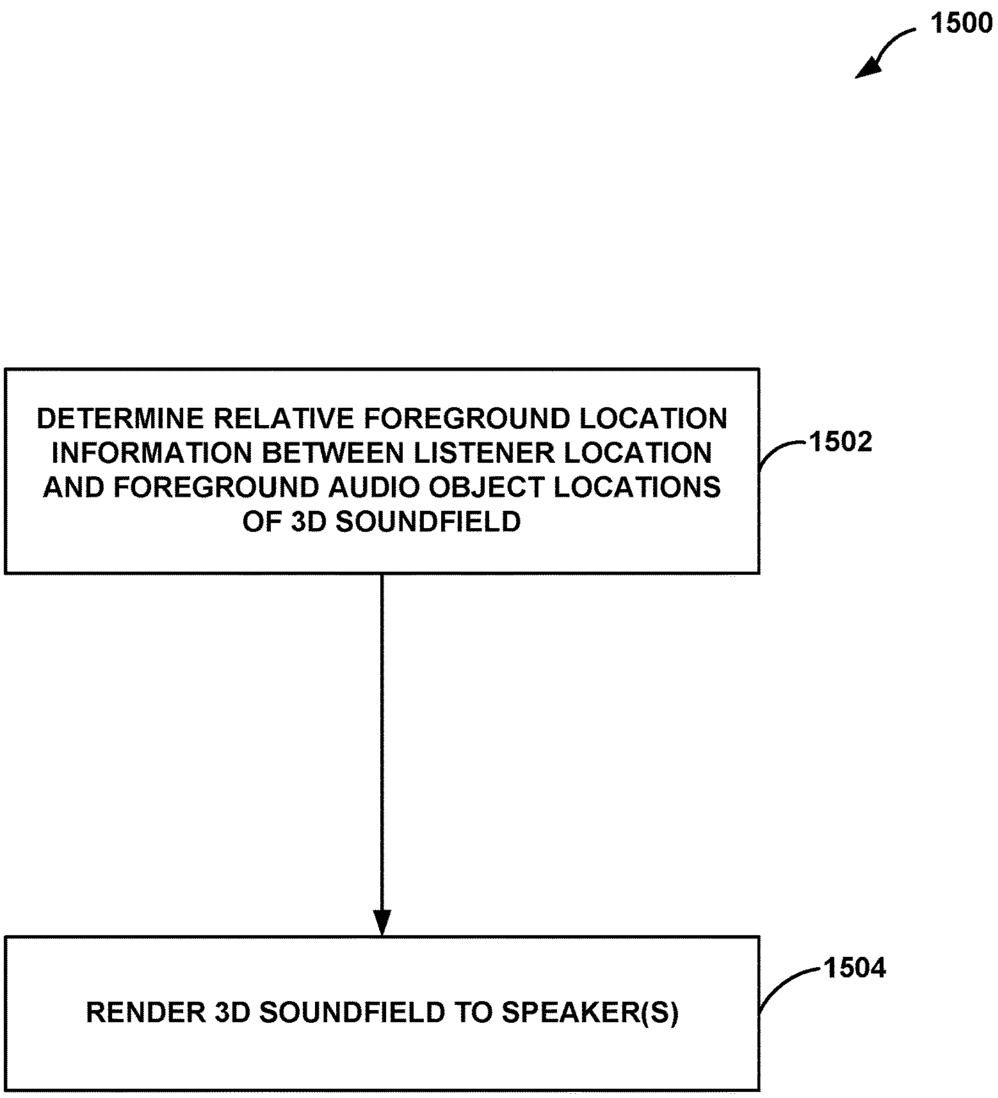
FIG. 15 is a flowchart illustrating an example process that an audio decoding device or an integrated encoding/decoding/rendering device may perform, in accordance with aspects of this disclosure.

FIG. 15 is a flowchart illustrating an example process 1500 that an audio decoding device or an integrated encoding/decoding/rendering device may perform, in accordance with aspects of this disclosure. Process 1500 may begin when processing circuitry of the audio decoding device determines relative foreground location information between a listener location and respective locations associated with one or more foreground audio objects of a 3D soundfield (1502). For instance, the processing circuitry of the audio decoding device may be coupled or otherwise in communication with a memory of the audio decoding device.

The memory, in turn, may be configured to store the listener location and respective locations associated with the one or more foreground audio objects of the 3D soundfield. The respective locations associated with the one or more foreground audio objects may be obtained from video data associated with the 3D soundfield. In turn, the processing circuitry of the audio decoding device may render the 3D soundfield to one or more speakers (1504). For instance, the processing circuitry of the audio decoding device may render the 3D soundfield into one or more speaker feeds that drive one or more loudspeakers, headphones, etc. that are communicatively coupled to the audio decoding device.

In some examples of this disclosure, an audio decoding device includes a memory device configured to store a listener location and respective locations associated with one or more foreground audio objects of a three-dimensional (3D) soundfield, the respective locations associated with the one or more foreground audio objects being obtained from video data associated with the 3D soundfield, and also includes processing circuitry coupled to the memory device the processing circuitry being configured to determine relative foreground location information between the listener location and the respective locations associated with the one or more foreground audio objects of the 3D soundfield. In some examples, the processing circuitry is further configured to apply a coordinate system to determine the relative foreground location information. In some examples, the processing circuitry is further configured to determine the listener location information by detecting a device. In some examples, the detected device includes a virtual reality (VR) headset. In some examples, the processing circuitry is further configured to determine the listener location information by detecting a person. In some examples, the processing circuitry is further configured to determine the listener location using a point cloud based interpolation process. In some examples, the processing circuitry is further configured to obtain a plurality of listener location candidates, and to interpolate the listener location between at least two listener location candidates of the obtained plurality of listener location candidates.

Figure 16:
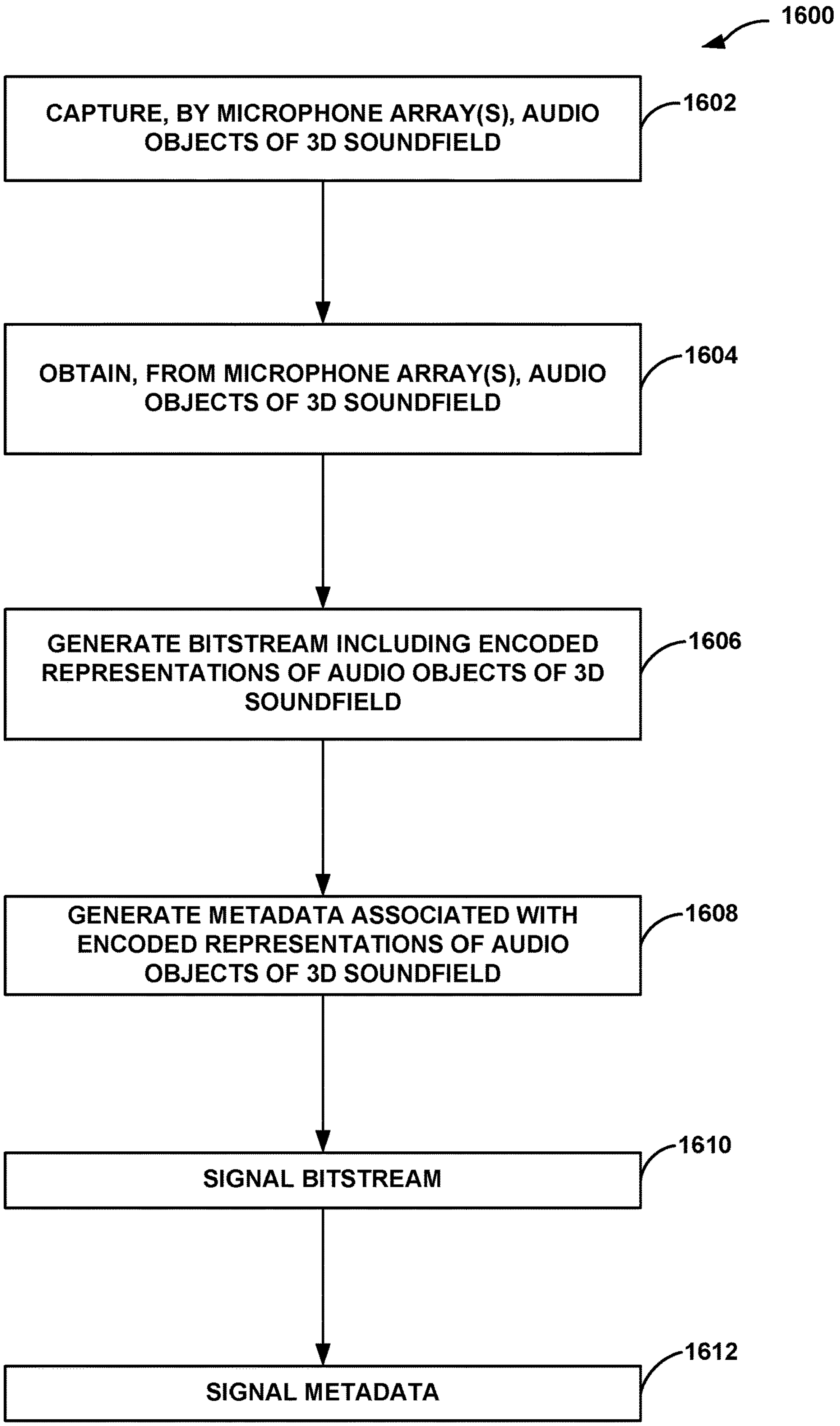
FIG. 16 is a flowchart illustrating a process that an audio encoding device or an integrated encoding/rendering device may perform, in accordance with aspects of this disclosure.

FIG. 16 is a flowchart illustrating a process 1600 that an audio encoding device or an integrated encoding/rendering device may perform, in accordance with aspects of this disclosure. Process 1600 may begin when one or more microphone arrays capture audio objects of a 3D soundfield (1602). In turn, processing circuitry of the audio encoding device may obtain, from the microphone array(s), the audio objects of the 3D soundfield captured by the microphone array(s) (1604). For instance, a memory device of the audio encoding device may store data representing (e.g., encoded representations of) the audio objects captured by the microphone array(s), and the processing circuitry may be in communication with the memory device. In this example, the processing circuitry may retrieve the encoded representations of the audio objects from the memory device.

The processing circuitry of the audio encoding device may generate a bitstream that includes the encoded representations of the audio objects of the 3D soundfield (1606). The processing circuitry of the audio encoding device may generate metadata associated with the bitstream that includes the encoded representations of the audio objects of the 3D soundfield (1608). The metadata may include one or more of transmission factors with respect to the audio objects, relative foreground location information between listener location information and respective locations associated with foreground audio objects of the audio objects, or location information for one or more silent objects of the audio objects. Although steps 1606 and 1608 of process 1600 are illustrated in a particular order for ease of illustration and discussion, it will be appreciated that the processing circuitry of the audio encoding device may generate the bitstream and the metadata in any order, including the reverse order of the order illustrated in FIG. 16, or in parallel (whether partially or completely).

The processing circuitry of the audio encoding device may signal the bitstream (1610). The processing circuitry of the audio encoding device may signal the metadata associated with the bitstream (1612). For instance, the processing circuitry may use a communication unit or other communication interface hardware of the audio encoding device to signal the bitstream and/or the metadata. Although the signaling operations (steps 1610 and 1612) of process 1600 are illustrated in a particular order for ease of illustration and discussion, it will be appreciated that the processing circuitry of the audio encoding device may signal the bitstream and the metadata in any order, including the reverse order of the order illustrated in FIG. 16, or in parallel (whether partially or completely).

In some examples of this disclosure, an audio encoding device includes a memory device configured to store encoded representations of audio objects of a three-dimensional (3D) soundfield, and further includes processing circuitry coupled to the memory device and configured to generate metadata associated with a bitstream that includes the encoded representations of the audio objects of the 3D soundfield, the metadata including one or more of transmission factors with respect to the audio objects, relative foreground location information between listener location information and respective locations associated with foreground audio objects of the audio objects, or location information for one or more silent objects of the audio objects. In some examples, the processing circuitry is configured to generate the transmission factors based on attenuation information associated with the silent objects and the foreground audio objects.

In some examples, the transmission factors represent energy attenuation information with respect to the foreground audio objects based on the location information for the silent objects. In some examples, the transmission factors represent directional attenuation information with respect to the foreground audio objects based on the location information for the silent objects. In some examples, the processing circuitry is further configured to determine the transmission factors based on the listener location information and the location information for the silent objects. In some examples, the processing circuitry is further configured to determine the transmission factors based on the listener location information and location information for the foreground audio objects. In some examples, the processing circuitry is further configured to generate the bitstream that includes the encoded representations of the audio objects of the 3D soundfield, and to signal the bitstream. In some examples, the processing circuitry being configured to signal the metadata within the bitstream. In some examples, the processing circuitry being configured to signal the metadata out-of-band with respect to the bitstream.

In some examples of this disclosure, an audio decoding device includes a memory device configured to store one or more audio objects of a three-dimensional (3D) soundfield, and also includes processing circuitry coupled to the memory device. The processing circuitry is configured to obtain metadata that includes transmission factors with respect to the one or more audio objects of the 3D soundfield, and to apply the transmission factors to audio signals associated with the one or more audio objects of the 3D soundfield. In some examples, the processing circuitry is further configured to attenuate energy information for the one or more audio signals. In some examples the one or more audio objects include foreground audio objects of the 3D soundfield.

Figure 17:
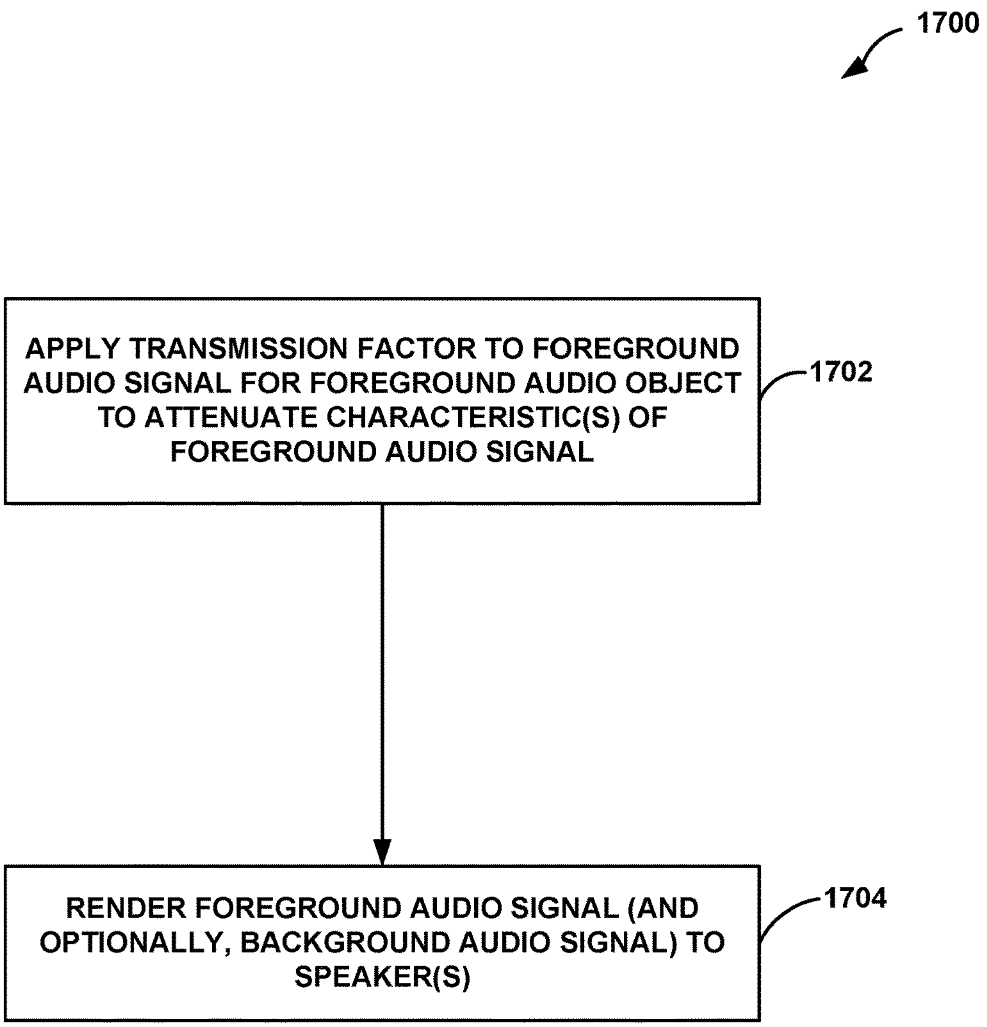
FIG. 17 is a flowchart illustrating an example process that an audio decoding device or an integrated encoding/decoding/rendering device may perform, in accordance with aspects of this disclosure.

FIG. 17 is a flowchart illustrating an example process 1700 that an audio decoding device or an integrated encoding/decoding/rendering device may perform, in accordance with aspects of this disclosure. Process 1700 may begin when processing circuitry of the audio decoding device applies a transmission factor to a foreground audio signal for a foreground audio object, to attenuate one or more characteristics of the foreground audio signal (1702). For instance, the processing circuitry of the audio decoding device may be coupled or otherwise in communication with a memory of the audio decoding device. The memory, in turn, may be configured to store the foreground audio object (which may be part of a 3D soundfield).

The processing circuitry of the audio decoding device may render the foreground audio signal to one or more speakers (1704). In some instances, the processing circuitry of the audio decoding device may also render a background audio signal (associated with a background audio object of the 3D soundfield) to the one or more speakers (1704). For instance, the processing circuitry of the audio decoding device may render the foreground audio signal (and optionally, the background audio signal) into one or more speaker feeds that drive one or more loudspeakers, headphones, etc. that are communicatively coupled to the audio decoding device.

Figure 18:
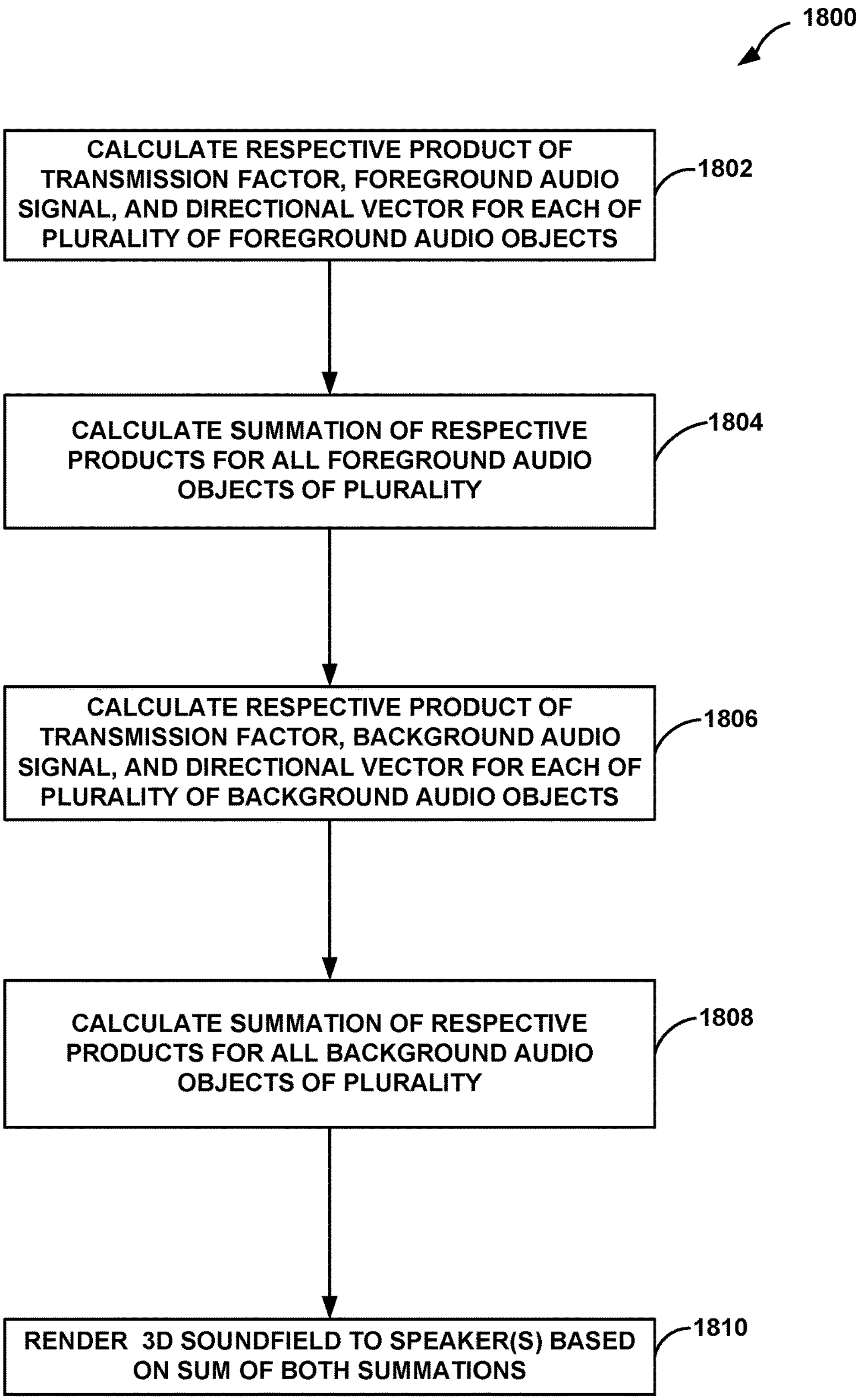
FIG. 18 is a flowchart illustrating an example process that an audio decoding device or an integrated encoding/decoding/rendering device may perform, in accordance with aspects of this disclosure.

FIG. 18 is a flowchart illustrating an example process 1800 that an audio decoding device or an integrated encoding/decoding/rendering device may perform, in accordance with aspects of this disclosure. Process 1800 may begin when processing circuitry of the audio decoding device calculates for each respective foreground audio object of a plurality of foreground audio objects, a respective product of a respective set of a transmission factor, a foreground audio signal, and a directional vector (1802). For instance, the processing circuitry of the audio decoding device may be coupled or otherwise in communication with a memory of the audio decoding device. The memory, in turn, may be configured to store the plurality of foreground audio objects (which may be part of a 3D soundfield). The processing circuitry of the audio decoding device may calculate a summation of the respective products calculated for all of the foreground audio objects of the plurality (1804).

Additionally, the processing circuitry of the audio decoding device may calculate a respective product of a respective set of a transmission factor, a background audio signal, and a directional vector (1806). The memory may be configured to store the plurality of background audio objects (which may be part of the same 3D soundfield as the plurality of foreground audio objects stored to the memory). The processing circuitry of the audio decoding device may calculate a summation of the respective products for all background audio objects of the plurality of background audio objects (1808). In turn, the processing circuitry of the audio decoding device may render the 3D soundfield to one or more speakers based on a sum of both calculated summations (1810).

That is, the processing circuitry of the audio decoding device may calculate a summation of (i) the calculated summation of the respective products calculated for all of the stored foreground audio objects, and (ii) the calculated summation of the respective products calculated for all of the stored background audio objects. In turn, the processing circuitry of the audio decoding device may render the 3D soundfield into one or more speaker feeds that drive one or more loudspeakers, headphones, etc. that are communicatively coupled to the audio decoding device.

In some examples of this disclosure, an audio decoding device includes a memory device configured to store a foreground audio object of a three-dimensional (3D) soundfield, and processing circuitry coupled to the memory device. The processing circuitry is configured to apply a transmission factor to a foreground audio signal for a foreground audio object to attenuate one or more characteristics of the foreground audio signal. In some examples, the processing circuitry is configured to attenuate an energy of the foreground audio signal. In some examples, the processing circuitry is configured to apply a translation factor to a background audio object.

In some examples of this disclosure, an audio decoding device includes a memory device configured to store a plurality of foreground audio objects of a three-dimensional (3D) soundfield. The device also includes processing circuitry coupled to the memory device, and being configured to calculate, for each respective foreground audio object of the plurality of foreground audio objects, a respective product of a respective set of a transmission factor, a foreground audio signal, and a directional vector, and to calculate a summation of the respective products for all foreground audio objects of the plurality of foreground audio objects. In some examples, the memory device is further configured to store and a plurality of background audio objects, and the processing circuitry is further configured to calculate, for each respective background audio object of a plurality of background audio objects, a respective product of a respective background audio signal and a respective translation factor, and to calculate a summation of the respective products for all background audio objects of the plurality of background audio objects. In some examples, the processing circuitry is further configured to add the summation of the products for the foreground audio objects to the summation of the products for the background audio objects. In some examples, the processing circuitry is further configured to perform all calculations in a higher order ambisonics (HOA) domain.

In some instances, a non-transitory computer-readable storage medium having stored thereon instructions that, when executed, cause one or more processors to obtain an audio object, obtain a video object, associate the audio object and the video object, compare the audio object to the associated video object and render the audio object based on the comparison between the audio object and the associated video object.

Various aspects of the techniques described in this disclosure may also be performed by a device that generates an audio output signal. The device may comprise means for identifying a first audio object associated with a first video object counterpart based on a first comparison of a data component of the first audio object and a data component of the first video object, and means for identifying a second audio object not associated with a second video object counterpart based on a second comparison of a data component of the second audio object and a data component of the second video object. The device may additionally comprise means for rendering the first audio object in a first zone, means for rendering the second audio object in a second zone, and means for generating the audio output signal based on combining the rendered first audio object in the first zone and the rendered second audio object in the second zone. The various means described herein may comprise one or more processors configured to perform the functions described with respect to each of the means.

In some instances, the data component of the first audio object comprises one of a location and a size. In some instances, the data component of the first video object data comprises one of a location and a size. In some instances, the data component of the second audio object comprises one of a location and a size. In some instances, the data component of the second video object comprises one of a location and a size.

In some instances, the first zone and second zone are different zones within an audio foreground or different zones within an audio background. In some instances, the first zone and second zone are a same zone within an audio foreground or a same zone within an audio background. In some instances, the first zone is within an audio foreground and the second zone is within an audio background. In some instances, the first zone is within an audio background and the second zone is within an audio foreground.

In some instances, the data component of the first audio object, the data component of the second audio object, the data component of the first video object, and the data component of the second video object each comprises metadata.

In some instances, the device further comprises means for determining whether the first comparison is outside a confidence interval, and means for weighting the data component of the first audio object and the data component of first video object based on the determination of whether the first comparison is outside the confidence interval. In some instances, the means for weighting comprises means for averaging the data component of the first audio object data and the data component of the first video object. In some instances, the device may also include means for allocating a different number of bits based on one or more of the first comparison and the second comparison.

In some instances, the techniques may provide for a non-transitory computer-readable storage medium having stored thereon instructions that, when executed, cause one or more processors to identify a first audio object associated with a first video object counterpart based on a first comparison of a data component of the first audio object and a data component of the first video object, identify a second audio object not associated with a second video object counterpart based on a second comparison of a data component of the second audio object and a data component of the second video object, render the first audio object in a first zone, means for rendering the second audio object in a second zone, and generate the audio output signal based on combining the rendered first audio object in the first zone and the rendered second audio object in the second zone.

Various examples of this disclosure are described below. In accordance with some of the examples described below, a "device" such as an audio encoding device may include, be, or be part of one or more of a flying device, a robotic device, or an automobile. In accordance with some of the examples described below, the operation of "rendering" or a configuration causing processing circuitry to "render" may include rendering to loudspeaker feeds, or rendering to headphone feeds to headphone speakers, such as by using binaural audio speaker feeds. For instance, an audio decoding device of this disclosure may render binaural audio speaker feeds by invoking or otherwise using a binaural audio renderer.

Example 1a

A method comprising: obtaining, from one or more microphone arrays, audio objects of a three-dimensional (3D) soundfield, wherein each obtained audio object is associated with a respective audio scene; obtaining, from one or more video capture devices, video data comprising one or more video scenes, each respective video scene being associated with a respective audio scene of the obtained audio data; determining that a video object included in a first video scene is not represented by any corresponding audio object in a first audio scene that corresponds to the first video scene; determining that the video object is not associated with any pre-identified audio object; and responsive to the determinations that the video object is not represented by any corresponding audio object in the first audio scene and that the video object is not associated with any pre-identified audio object, identifying the video object as a silent object.

Example 2a

The method of example 1a, further comprising: determining that a first audio object included in obtained audio data is associated with a pre-identified audio object; and responsive to the determination that the audio object is associated with the pre-identified audio object, identifying the first audio object as a foreground audio object.

Example 3a

The method of any of examples 1a or 2a, further comprising: determining that a second audio object included in obtained audio data is not associated with any pre-identified audio object; and responsive to the determination that the second audio object is not associated with any pre-identified audio object, identifying the second audio object as a background audio object.

Example 4a

The method of any of examples 2a or 3a, wherein determining that the first audio object is associated with a pre-identified audio object comprises determining that the first audio object is associated with an audio source that is equipped with one or more sensors.

Example 5a

The method of any of examples 1a-4a, wherein the foreground audio object is included in the first audio scene that corresponds to the first video scene, the method further comprising: determining whether positional information of the silent object with respect to the first video scene causes attenuation of the foreground audio object.

Example 6a

The method of example 5a, further comprising: responsive to determining that the silent object causes the attenuation of the foreground audio object, generating one or more transmission factors with respect to the foreground audio object, wherein the generated transmission factors represent adjustments with respect to the foreground audio object.

Example 7a

The method of example 6a, wherein the generated transmission factors represent adjustments with respect to an energy of the foreground audio object.

Example 8a

The method of any of examples 6a or 7a, wherein the generated transmission factors represent adjustments with respect to directional characteristics of the foreground audio object.

Example 9a

The method of any of examples 6a-8a, further comprising transmitting the transmission factors out of band with respect to a bitstream that includes the foreground audio object.

Example 10a

The method of example 9a, wherein the generated transmission factors represent metadata with respect to the bitstream.

Example 11a

An audio encoding device comprising: a memory device configured to: store audio objects obtained from one or more microphone arrays with respect to a three-dimensional (3D) soundfield, wherein each obtained audio object is associated with a respective audio scene; and store video data obtained from one or more video capture devices, the video data comprising one or more video scenes, each respective video scene being associated with a respective audio scene of the obtained audio data. The audio encoding device further comprises processing circuitry coupled to the memory device, the processing circuitry being configured to: determine that a video object included in a first video scene is not represented by any corresponding audio object in a first audio scene that corresponds to the first video scene; determine that the video object is not associated with any pre-identified audio object; and identify, responsive to the determinations that the video object is not represented by any corresponding audio object in the first audio scene and that the video object is not associated with any pre-identified audio object, the video object as a silent object.

Example 12a

The audio encoding device of example 11a, the processing circuitry being further configured to: determine that a first audio object included in obtained audio data is associated with a pre-identified audio object; and identify, responsive to the determination that the audio object is associated with the pre-identified audio object, the first audio object as a foreground audio object.

Example 13a

The audio encoding device of any of examples 11a or 12a, the processing circuitry being further configured to: determine that a second audio object included in obtained audio data is not associated with any pre-identified audio object; and identify, responsive to the determination that the second audio object is not associated with any pre-identified audio object, the second audio object as a background audio object.

Example 14a

The audio encoding device of any of examples 12a or 13a, the processing circuitry being further configured to: determine that the first audio object is associated with a pre-identified audio object by determining that the first audio object is associated with an audio source that is equipped with one or more sensors.

Example 14a(i)

The audio encoding device of example 14a, further comprising one or more microphone arrays coupled to the processing circuitry, the one or more microphone arrays being configured to capture the audio objects associated with the 3D soundfield.

Example 14a(ii)

The audio encoding device of any of examples 11a-14a(i), further comprising the one or more video capture devices coupled to the processing circuitry, the one or more video capture devices being configured to capture the video data.

Example 15a

The audio encoding device of any of examples 11 a-14a, wherein the foreground audio object is included in the first audio scene that corresponds to the first video scene, the processing circuitry being further configured to: determine whether positional information of the silent object with respect to the first video scene causes attenuation of the foreground audio object.

Example 16a

The audio encoding device of example 15a, the processing circuitry being further configured to: generate, responsive to determining that the silent object causes the attenuation of the foreground audio object, one or more transmission factors with respect to the foreground audio object, wherein the generated transmission factors represent adjustments with respect to the foreground audio object.

Example 17a

The audio encoding device of example 16a, wherein the generated transmission factors represent adjustments with respect to an energy of the foreground audio object.

Example 18a

The audio encoding device of any of examples 16a or 17a, wherein the generated transmission factors represent adjustments with respect to directional characteristics of the foreground audio object.

Example 19a

The audio encoding device of any of examples 16a-18a, the processing circuitry being further configured to transmit the transmission factors out of band with respect to a bitstream that includes the foreground audio object.

Example 20a

The audio encoding device of example 19a, wherein the generated transmission factors represent metadata with respect to the bitstream.

Example 21a

An audio encoding apparatus comprising: means for obtaining, from one or more microphone arrays, audio objects of a three-dimensional (3D) soundfield, wherein each obtained audio object is associated with a respective audio scene; means for obtaining, from one or more video capture devices, video data comprising one or more video scenes, each respective video scene being associated with a respective audio scene of the obtained audio data; means for determining that a video object included in a first video scene is not represented by any corresponding audio object in a first audio scene that corresponds to the first video scene; means for determining that the video object is not associated with any pre-identified audio object; and means for identifying, responsive to the determinations that the video object is not represented by any corresponding audio object in the first audio scene and that the video object is not associated with any pre-identified audio object, the video object as a silent object.

Example 22a

A non-transitory computer-readable storage medium encoded with instructions that, when executed, cause processing circuitry of an audio encoding device to: obtain, from one or more microphone arrays, audio objects of a three-dimensional (3D) soundfield, wherein each obtained audio object is associated with a respective audio scene; obtain, from one or more video capture devices, video data comprising one or more video scenes, each respective video scene being associated with a respective audio scene of the obtained audio data; determine that a video object included in a first video scene is not represented by any corresponding audio object in a first audio scene that corresponds to the first video scene; determine that the video object is not associated with any pre-identified audio object; and identify, responsive to the determinations that the video object is not represented by any corresponding audio object in the first audio scene and that the video object is not associated with any pre-identified audio object, the video object as a silent object.

Example 1b

An audio decoding device comprising: processing circuitry configured to: receive, in a bitstream, encoded representations of audio objects of a three-dimensional (3D) soundfield; receive metadata associated with the bitstream; obtain, from the received metadata, one or more transmission factors associated with one or more of the audio objects; and apply the transmission factors to the one or more audio objects to obtain parallax-adjusted audio objects of the 3D soundfield; and a memory device coupled to the processing circuitry, the memory device being configured to store at least a portion of the received bitstream, the received metadata, or the parallax-adjusted audio objects of the 3D soundfield.

Example 2b

The audio decoding device of example 1b, the processing circuitry being further configured to: determine listener location information; apply the listener location information in addition to applying the transmission factors to the one or more audio objects.

Example 3b

The audio decoding device of example 2b, the processing circuitry being further configured to apply relative foreground location information between the listener location information and respective locations associated with foreground audio objects of the one or more audio objects.

Example 4b

The audio decoding device of example 3b, the processing circuitry being further configured to apply a coordinate system to determine the relative foreground location information.

Example 5b

The audio decoding device of example 2b, the processing circuitry being further configured to the processing circuitry being further configured to determine the listener location information by detecting a device.

Example 6b

The audio decoding device of claim 5b, wherein the detected device comprises one or more of a virtual reality (VR) headset, a mixed reality (MR) headset, or an augmented reality (AR) headset.

Example 7b

The audio decoding device of example 2b, the processing circuitry being further configured to the processing circuitry being further configured to determine the listener location information by detecting a person.

Example 8b

The audio decoding device of example 2b, the processing circuitry being further configured to determine the listener location using a point cloud based interpolation process.

Example 9b

The audio decoding device of example 7b, the processing circuitry being further configured to: obtain a plurality of listener location candidates; and interpolate the listener location between at least two listener location candidates of the obtained plurality of listener location candidates.

Example 10b

The audio decoding device of example 1b, the processing circuitry being further configured to apply background translation factors that are calculated using respective locations associated with background audio objects of the one or more audio objects.

Example 11b

The audio decoding device of example 1b, the processing circuitry being further configured to apply foreground attenuation factors to respective foreground audio objects of the one or more audio objects.

Example 12b

The audio decoding device of example 1b, the processing circuitry being further configured to: determine a minimum transmission value for the respective foreground audio objects; determine whether applying the transmission factors to the respective foreground audio objects produces an adjusted transmission value that is lower than the minimum transmission value; and render, responsive to determining that the adjusted transmission value that is lower than the minimum transmission value, the respective foreground audio objects using the minimum transmission value.

Example 13b

The audio decoding device of example 1b, the processing circuitry being further configured to adjust an energy of the respective foreground audio objects.

Example 14b

The audio decoding device of example 12b, the processing circuitry being further configured to attenuate respective energies of the respective foreground audio objects.

Example 15b

The audio decoding device of example 12b, the processing circuitry being further configured to adjust directional characteristics of the respective foreground audio objects.

Example 16b

The audio decoding device of example 12b, the processing circuitry being further configured to adjust parallax information of the respective foreground audio objects.

Example 17b

The audio decoding device of example 16b, the processing circuitry being further configured to adjust the parallax information to account for one or more silent objects represented in a video stream associated with the 3D soundfield.

Example 18b

The audio decoding device of example 1b, the processing circuitry being further configured to receive the metadata within the bitstream.

Example 19b

The audio decoding device of example 1b, the processing circuitry being further configured to receive the metadata out of band with respect to the bitstream.

Example 20b

The audio decoding device of example 1b, the processing circuitry being further configured to output video data associated with the 3D soundfield to one or more displays.

Example 21b

The audio decoding device of example 20b, further comprising the one or more displays, the one or more displays being configured to: receive the video data from the processing circuitry; and output the received video data in visual form.

Example 22b

The audio decoding device of example 1b, the processing circuitry being further configured to attenuate an energy of a foreground audio object of the one or more audio objects.

Example 23b

The audio decoding device of example 1b, the processing circuitry being further configured to apply a translation factor to a background audio object.

Example 24b

The audio decoding device of example 1b, the processing circuitry being further configured to: calculate, for each respective background audio object of a plurality of background audio objects of the one or more audio objects, a respective product of a respective background audio signal and a respective translation factor; and calculate a summation of the respective products for all background audio objects of the plurality of background audio objects.

Example 25b

The audio decoding device of example 24b, the processing circuitry being further configured to add the summation of the products for the foreground audio objects to the summation of the products for the background audio objects.

Example 26b

A method comprising: receiving, in a bitstream, encoded representations of audio objects of a three-dimensional (3D) soundfield; receiving metadata associated with the bitstream; obtaining, from the received metadata, one or more transmission factors associated with one or more of the audio objects; and applying the transmission factors to the one or more audio objects to obtain parallax-adjusted audio objects of the 3D soundfield.

Example 27b

The method of example 26b, wherein applying the transmission factors comprises applying background translation factors that are calculated using respective locations associated with background audio objects of the one or more audio objects.

Example 28b

The method of example 26b, wherein applying the transmission factors comprises applying foreground attenuation factors to respective foreground audio objects of the one or more audio objects.

Example 29b

The method of example 26b, further comprising: determining a minimum transmission value for the respective foreground audio objects; determining whether applying the transmission factors to the respective foreground audio objects produces an adjusted transmission value that is lower than the minimum transmission value; and responsive to determining that the adjusted transmission value is lower than the minimum transmission value, rendering the respective foreground audio objects using the minimum transmission value.

Example 30b

The method of example 26b, wherein applying the transmission factors comprises adjusting an energy of the respective foreground audio objects.

Example 31b

The method of claim 30b, wherein adjusting the energy comprises attenuating respective energies of the respective foreground audio objects.

Example 32b

The method of example 26b, wherein applying the transmission factors comprises adjusting directional characteristics of the respective foreground audio objects.

Example 33b

The method of example 26b, wherein applying the transmission factors comprises adjusting parallax information of the respective foreground audio objects.

Example 34b

The method of claim 33b, wherein adjusting the parallax information comprises adjusting the parallax information to account for one or more silent objects represented in a video stream associated with the 3D soundfield.

Example 35b

The method of example 26b, wherein receiving the metadata comprises receiving the metadata within the bitstream.

Example 36b

The method of example 26b, wherein receiving the metadata comprises receiving the metadata out of band with respect to the bitstream.

Example 37b

A non-transitory computer-readable storage medium encoded with instructions that, when executed, cause processing circuitry of an audio encoding device to: receive, in a bitstream, encoded representations of audio objects of a three-dimensional (3D) soundfield; receive metadata associated with the bitstream; obtain, from the received metadata, one or more transmission factors associated with one or more of the audio objects; and apply the transmission factors to the one or more audio objects to obtain parallax-adjusted audio objects of the 3D soundfield.

Example 38b

An audio decoding apparatus comprising: means for receiving, in a bitstream, encoded representations of audio objects of a three-dimensional (3D) soundfield; means for receiving metadata associated with the bitstream; means for obtaining, from the received metadata, one or more transmission factors associated with one or more of the audio objects; and means for applying the transmission factors to the one or more audio objects to obtain parallax-adjusted audio objects of the 3D soundfield.

Example 1c. A method comprising: determining relative foreground location information between a listener location and respective locations associated with one or more foreground audio objects of a three-dimensional (3D) soundfield, the respective locations associated with the one or more foreground audio objects being obtained from video data associated with the 3D soundfield.

Example 2c

The method of example 1c, further comprising applying a coordinate system to determine the relative foreground location information.

Example 3c

The method of any of examples 1c or 2c, further comprising determining the listener location information by detecting a device.

Example 4c

The method of example 3c, wherein the device comprises a virtual reality (VR) headset.

Example 5c

The method of any of examples 1c or 2c, further comprising determining the listener location information by detecting a person.

Example 6c

The method of any of examples 1c or 2c, further comprising determining the listener location using a point cloud based interpolation process.

Example 7c

The method of example 6c, wherein using the point cloud based interpolation process comprises: obtaining a plurality of listener location candidates; and interpolating the listener location between at least two listener location candidates of the obtained plurality of listener location candidates.

Example 8c

An audio decoding device comprising: a memory device configured to store a listener location and respective locations associated with one or more foreground audio objects of a three-dimensional (3D) soundfield, the respective locations associated with the one or more foreground audio objects being obtained from video data associated with the 3D soundfield; and processing circuitry coupled to the memory device, the processing circuitry being configured to determine relative foreground location information between the listener location and the respective locations associated with the one or more foreground audio objects of the 3D soundfield.

Example 9c

The audio decoding device of example 8c, the processing circuitry being further configured to apply a coordinate system to determine the relative foreground location information.

Example 10c

The audio decoding device of any of examples 8c or 9c, the processing circuitry being further configured to determine the listener location information by detecting a device.

Example 11c

The audio decoding device of example 10c, wherein the detected device comprises one or more of a virtual reality (VR) headset, a mixed reality (MR) headset, or an augmented reality (AR) headset.

Example 12c

The audio decoding device of any of examples 8c or 9c, the processing circuitry being further configured to determine the listener location information by detecting a person.

Example 13c

The audio decoding device of any of examples 8c or 9c, the processing circuitry being further configured to determine the listener location using a point cloud based interpolation process.

Example 14c

The audio decoding device of example 13c, the processing circuitry being further configured to: obtain a plurality of listener location candidates; and interpolate the listener location between at least two listener location candidates of the obtained plurality of listener location candidates.

Example 15c

An audio decoding apparatus comprising: means for determining relative foreground location information between a listener location and respective locations associated with one or more foreground audio objects of a three-dimensional (3D) soundfield, the respective locations associated with the one or more foreground audio objects being obtained from video data associated with the 3D soundfield.

Example 16c

A non-transitory computer-readable storage medium encoded with instructions that, when executed, cause processing circuitry of an audio decoding device to: determine relative foreground location information between a listener location and respective locations associated with one or more foreground audio objects of a three-dimensional (3D) soundfield, the respective locations associated with the one or more foreground audio objects being obtained from video data associated with the 3D soundfield.

Example 1d

A method comprising: generating metadata associated with a bitstream that includes encoded representations of audio objects of a three-dimensional (3D) soundfield, the metadata including one or more of transmission factors with respect to the audio objects, relative foreground location information between listener location information and respective locations associated with foreground audio objects of the audio objects, or location information for one or more silent objects of the audio objects.

Example 2d

The method of example 1 d, wherein generating the metadata comprises generating the transmission factors based on attenuation information associated with the silent objects and the foreground audio objects.

Example 3d

The method claim 2d, wherein the transmission factors represent energy attenuation information with respect to the foreground audio objects based on the location information for the silent objects.

Example 4d

The method of any of examples 2d or 3d, wherein the transmission factors represent directional attenuation information with respect to the foreground audio objects based on the location information for the silent objects.

Example 5d

The method of any of examples 2d-4d, further comprising determining the transmission factors based on the listener location information and the location information for the silent objects.

Example 6d

The method of any of examples 2d-5d, further comprising determining the transmission factors based on the listener location information and location information for the foreground audio objects.

Example 7d

The method of any of examples 1d-6d, further comprising: generating the bitstream that includes the encoded representations of the audio objects of the 3D soundfield; and signaling the bitstream.

Example 8d

The method of example 7d, further comprising signaling the metadata within the bitstream.

Example 9d

The method of example 7d, further comprising signaling the metadata out-of-band with respect to the bitstream.

Example 10d

A method comprising: obtaining metadata that includes transmission factors with respect to one or more audio objects of a three-dimensional (3D) soundfield; and applying the transmission factors to audio signals associated with the one or more audio objects of the 3D soundfield.

Example 11d

The method of example 10d, wherein applying the transmission factors to the audio signals comprises attenuating energy information for the one or more audio signals.

Example 12d

The method of any of examples 10d or 11d, wherein the one or more audio objects comprise foreground audio objects of the 3D soundfield.

Example 13d

An audio encoding device comprising: a memory device configured to store encoded representations of audio objects of a three-dimensional (3D) soundfield; and processing circuitry coupled to the memory device and configured to generate metadata associated with a bitstream that includes the encoded representations of the audio objects of the 3D soundfield, the metadata including one or more of transmission factors with respect to the audio objects, relative foreground location information between listener location information and respective locations associated with foreground audio objects of the audio objects, or location information for one or more silent objects of the audio objects.

Example 14d

The audio encoding device of example 13d, the processing circuitry being configured to generate the transmission factors based on attenuation information associated with the silent objects and the foreground audio objects.

Example 15d

The audio encoding device of example 14d, wherein the transmission factors represent energy attenuation information with respect to the foreground audio objects based on the location information for the silent objects.

Example 16d

The audio encoding device of any of examples 14d or 15d, wherein the transmission factors represent directional attenuation information with respect to the foreground audio objects based on the location information for the silent objects.

Example 17d

The audio encoding device of any of examples 14d-16d, the processing circuitry being further configured to determine the transmission factors based on the listener location information and the location information for the silent objects.

Example 18d

The audio encoding device of any of examples 14d-17d, the processing circuitry being further configured to determine the transmission factors based on the listener location information and location information for the foreground audio objects.

Example 19d

The audio encoding device of any of examples 13d-18d, the processing circuitry being further configured to: generate the bitstream that includes the encoded representations of the audio objects of the 3D soundfield; and signal the bitstream.

Example 20d

The audio encoding device of example 19d, the processing circuitry being configured to signal the metadata within the bitstream.

Example 21d

The audio encoding device of example 19d, the processing circuitry being configured to signal the metadata out-of-band with respect to the bitstream.

Example 22d

An audio decoding device comprising: a memory device configured to store one or more audio objects of a three-dimensional (3D) soundfield; and processing circuitry coupled to the memory device, and configured to: obtain metadata that includes transmission factors with respect to the one or more audio objects of the 3D soundfield; and apply the transmission factors to audio signals associated with the one or more audio objects of the 3D soundfield.

Example 23d

The audio decoding device of example 22d, the processing circuitry being further configured to attenuate energy information for the one or more audio signals.

Example 24d

The audio decoding device of any of examples 22d or 23d, wherein the one or more audio objects comprise foreground audio objects of the 3D soundfield.

Example 25d

An audio encoding apparatus comprising: means for generating metadata associated with a bitstream that includes encoded representations of audio objects of a three-dimensional (3D) soundfield, the metadata including one or more of transmission factors with respect to the audio objects, relative foreground location information between listener location information and respective locations associated with foreground audio objects of the audio objects, or location information for one or more silent objects of the audio objects.

Example 26d

An audio decoding apparatus comprising: means for obtaining metadata that includes transmission factors with respect to one or more audio objects of a three-dimensional (3D) soundfield; and means for applying the transmission factors to audio signals associated with the one or more audio objects of the 3D soundfield.

Example 27d

An integrated device comprising: the audio encoding device of example 13d; and the audio decoding device of example 14d.

Example 1e

A method of rendering a three-dimensional (3D) soundfield, the method comprising: applying a transmission factor to a foreground audio signal for a foreground audio object to attenuate one or more characteristics of the foreground audio signal.

Example 2e

The method of example 1e, wherein attenuating the characteristics of the foreground audio signal comprises attenuating an energy of the foreground audio signal.

Example 3e

The method of any of examples 1e or 2e, further comprising applying a translation factor to a background audio object.

Example 4e

An audio decoding device comprising: a memory device configured to store a foreground audio object of a three-dimensional (3D) soundfield; and processing circuitry coupled to the memory device and configured to apply a transmission factor to a foreground audio signal for a foreground audio object to attenuate one or more characteristics of the foreground audio signal.

Example 5e

The audio decoding device of example 4e, the processing circuitry being configured to attenuate an energy of the foreground audio signal.

Example 6e

The audio decoding device of any of examples 4e or 5e, the processing circuitry being configured to apply a translation factor to a background audio object.

Example 7e

An audio decoding apparatus comprising: means for applying a transmission factor to a foreground audio signal for a foreground audio object of a three-dimensional (3d) soundfield to attenuate one or more characteristics of the foreground audio signal.

Example 1f

A method of rendering a three-dimensional (3D) soundfield, the method comprising: calculating, for each respective foreground audio object of a plurality of foreground audio objects, a respective product of a respective of a transmission factor, a foreground audio signal, and a directional vector; and calculating a summation of the respective products for all foreground audio objects of the plurality of foreground audio objects.

Example 2f

The method of example 1f, further comprising: calculating, for each respective background audio object of a plurality of background audio objects, a respective product of a respective background audio signal and a respective translation factor; and calculating a summation of the respective products for all background audio objects of the plurality of background audio objects.

Example 3f

The method of example 2f, further comprising adding the summation of the products for the foreground audio objects to the summation of the products for the background audio objects.

Example 4f

The method of any of examples 1f-3f, further comprising performing all calculations in a higher order ambisonics (HOA) domain.

Example 5f

An audio decoding device comprising: a memory device configured to store a plurality of foreground audio objects of a three-dimensional (3D) soundfield; and processing circuitry coupled to the memory device, and being configured to: calculate, for each respective foreground audio object of the plurality of foreground audio objects, a respective product of a respective set of a transmission factor, a foreground audio signal, and a directional vector; and calculate a summation of the respective products for all foreground audio objects of the plurality of foreground audio objects.

Example 6f

The audio decoding device of example 5f, the memory device being further configured to store and a plurality of background audio objects, the processing circuitry being further configured to: calculate, for each respective background audio object of a plurality of background audio objects, a respective product of a respective background audio signal and a respective translation factor; and calculate a summation of the respective products for all background audio objects of the plurality of background audio objects.

Example 7f

The audio decoding device of example 6f, the processing circuitry being further configured to add the summation of the products for the foreground audio objects to the summation of the products for the background audio objects.

Example 8f

The audio decoding device of any of examples 5f-7f, the processing circuitry being further configured to perform all calculations in a higher order ambisonics (HOA) domain.

Example 9f

An audio decoding apparatus comprising: means for calculating, for each respective foreground audio object of a plurality of foreground audio objects of a three-dimensional (3D) soundfield, a respective product of a respective of a transmission factor, a foreground audio signal, and a directional vector; and means for calculating a summation of the respective products for all foreground audio objects of the plurality of foreground audio objects.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single module or unit for purposes of clarity, it should be understood that the techniques of this disclosure may be performed by a combination of units or modules associated with a video coder.

In one or more examples, the functions described may be implemented in hardware, software, firmware, or any combination thereof. If implemented in software, the functions may be stored on or transmitted over as one or more instructions or code on a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol.

In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium.

It should be understood, however, that computer-readable storage media and data storage media do not include connections, carrier waves, signals, or other transient media, but are instead directed to non-transient, tangible storage media. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. The term "processor" may be formed in one or more microprocessors, application specific integrated circuits (ASICs), field programmable gate arrays (FPGAs), digital signal processors (DSPs), processing circuitry (including fixed function circuitry and/or programmable processing circuitry), or other equivalent integrated or discrete logic circuitry. In addition, in some aspects, the functionality described herein may be provided within dedicated hardware and/or software modules configured for encoding and decoding, or incorporated in a combined codec. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a codec hardware unit or provided by a collection of interoperative hardware units, including one or more processors as described above, in conjunction with suitable software and/or firmware Various embodiments of the techniques have been described. These and other embodiments are within the scope of the following claims.

What is claimed is:

1. An audio decoding device comprising:

processing circuitry configured to:

receive, in a bitstream, encoded representations of audio objects of a three-dimensional (3D) soundfield;

receive metadata associated with the bitstream;

obtain, from the received metadata, one or more transmission factors associated with one or more of the audio objects; and apply the transmission factors to the one or more audio objects to obtain parallax-adjusted audio objects of the 3D soundfield; and a memory device coupled to the processing circuitry, the memory device being configured to store at least a portion of the received bitstream, the received metadata, or the parallax-adjusted audio objects of the 3D soundfield.

2. The audio decoding device of claim 1, the processing circuitry being further configured to:

determine listener location information;

apply the listener location information in addition to applying the transmission factors to the one or more audio objects.

3. The audio decoding device of claim 2, the processing circuitry being further configured to apply relative foreground location information between the listener location information and respective locations associated with foreground audio objects of the one or more audio objects.

4. The audio decoding device of claim 3, the processing circuitry being further configured to apply a coordinate system to determine the relative foreground location information.

5. The audio decoding device of claim 2, the processing circuitry being further configured to determine the listener location information by detecting a device.

6. The audio decoding device of claim 5, wherein the detected device comprises one or more of a virtual reality (VR) headset, a mixed reality (MR) headset, or an augmented reality (AR) headset.

7. The audio decoding device of claim 2, the processing circuitry being further configured to determine the listener location information by detecting a person.

8. The audio decoding device of claim 2, the processing circuitry being further configured to determine the listener location using a point cloud based interpolation process.

9. The audio decoding device of claim 8, the processing circuitry being further configured to:

obtain a plurality of listener location candidates; and interpolate the listener location between at least two listener location candidates of the obtained plurality of listener location candidates.

10. The audio decoding device of claim 1, the processing circuitry being further configured to apply background translation factors that are calculated using respective locations associated with background audio objects of the one or more audio objects.

11. The audio decoding device of claim 1, the processing circuitry being further configured to:

determine a minimum transmission value for the respective foreground audio objects;

determine whether applying the transmission factors to the respective foreground audio objects produces an adjusted transmission value that is lower than the minimum transmission value; and render, responsive to determining that the adjusted transmission value that is lower than the minimum transmission value, the respective foreground audio objects using the minimum transmission value.

12. The audio decoding device of claim 1, the processing circuitry being further configured to apply foreground attenuation factors to respective foreground audio objects of the one or more audio objects.

13. The audio decoding device of claim 12, the processing circuitry being further configured to adjust an energy of the respective foreground audio objects.

14. The audio decoding device of claim 12, the processing circuitry being further configured to attenuate respective energies of the respective foreground audio objects.

15. The audio decoding device of claim 12, the processing circuitry being further configured to adjust directional characteristics of the respective foreground audio objects.

16. The audio decoding device of claim 12, the processing circuitry being further configured to adjust parallax information of the respective foreground audio objects.

17. The audio decoding device of claim 16, the processing circuitry being further configured to adjust the parallax information to account for one or more silent objects represented in a video stream associated with the 3D soundfield.

18. The audio decoding device of claim 1, the processing circuitry being further configured to receive the metadata within the bitstream.

19. The audio decoding device of claim 1, the processing circuitry being further configured to receive the metadata out of band with respect to the bitstream.

20. The audio decoding device of claim 1, the processing circuitry being further configured to output video data associated with the 3D soundfield to one or more displays.

21. The audio decoding device of claim 20, further comprising the one or more displays, the one or more displays being configured to:

receive the video data from the processing circuitry; and output the received video data in visual form.

22. The audio decoding device of claim 1, the processing circuitry being further configured to attenuate an energy of a foreground audio object of the one or more audio objects.

23. The audio decoding device of claim 1, the processing circuitry being further configured to apply a translation factor to a background audio object.

24. The audio decoding device of claim 1, the processing circuitry being further configured to:

calculate, for each respective background audio object of a plurality of background audio objects of the one or more audio objects, a respective product of a respective background audio signal and a respective translation factor; and calculate a summation of the respective products for all background audio objects of the plurality of background audio objects.

25. The audio decoding device of claim 24, the processing circuitry being further configured to add the summation of the products for the foreground audio objects to the summation of the products for the background audio objects.

26. A method comprising:

receiving, in a bitstream, encoded representations of audio objects of a three-dimensional (3D) soundfield;

receiving metadata associated with the bitstream;

obtaining, from the received metadata, one or more transmission factors associated with one or more of the audio objects; and applying the transmission factors to the one or more audio objects to obtain parallax-adjusted audio objects of the 3D soundfield.

27. The method of claim 26, further comprising:

determining listener location information; and applying the listener location information in addition to applying the transmission factors to the one or more audio objects.

28. The method of claim 27, wherein applying the transmission factors and the listener location information comprises applying relative foreground location information between the listener location information and respective locations associated with foreground audio objects of the one or more audio objects.

29. An audio decoding apparatus comprising:

means for receiving, in a bitstream, encoded representations of audio objects of a three-dimensional (3D) soundfield;

means for receiving metadata associated with the bitstream;

means for obtaining, from the received metadata, one or more transmission factors associated with one or more of the audio objects; and means for applying the transmission factors to the one or more audio objects to obtain parallax-adjusted audio objects of the 3D soundfield.

30. A non-transitory computer-readable storage medium encoded with instructions that, when executed, cause processing circuitry of an audio decoding device to:

receive, in a bitstream, encoded representations of audio objects of a three-dimensional (3D) soundfield;

receive metadata associated with the bitstream;

obtain, from the received metadata, one or more transmission factors associated with one or more of the audio objects; and apply the transmission factors to the one or more audio objects to obtain parallax-adjusted audio objects of the 3D soundfield.

* * * * *